United States Patent
Slukvin et al.

(10) Patent No.: US 11,345,895 B2
(45) Date of Patent: May 31, 2022

(54) INDUCTION OF ARTERIAL-TYPE OF HEMOGENIC ENDOTHELIUM (AHE) AND ENHANCEMENT OF T CELL PRODUCTION FROM PSCS THROUGH OVEREXPRESSION OF ETS FACTORS OR MODULATING MAPK/ERK SIGNALLING PATHWAYS

(71) Applicant: Wisconsin Alumni Research Foundation, Madison, WI (US)

(72) Inventors: Igor I. Slukvin, Verona, WI (US); Mi Ae Park, Madison, WI (US); Akhilesh Kumar, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 936 days.

(21) Appl. No.: 15/816,914

(22) Filed: Nov. 17, 2017

(65) Prior Publication Data
US 2018/0142207 A1 May 24, 2018

Related U.S. Application Data

(60) Provisional application No. 62/572,066, filed on Oct. 13, 2017, provisional application No. 62/424,144, filed on Nov. 18, 2016.

(51) Int. Cl.
| | |
|---|---|
| *A61K 35/17* | (2015.01) |
| *C12N 5/071* | (2010.01) |
| *C07K 14/705* | (2006.01) |
| *C12N 5/0789* | (2010.01) |
| *C12N 5/0783* | (2010.01) |
| *C07K 14/47* | (2006.01) |
| *A61K 35/12* | (2015.01) |

(52) U.S. Cl.
CPC .............. *C12N 5/069* (2013.01); *A61K 35/17* (2013.01); *C07K 14/4702* (2013.01); *C07K 14/70503* (2013.01); *C12N 5/0636* (2013.01); *C12N 5/0647* (2013.01); *A61K 2035/124* (2013.01); *C12N 2501/42* (2013.01); *C12N 2501/60* (2013.01); *C12N 2501/602* (2013.01); *C12N 2501/727* (2013.01); *C12N 2506/02* (2013.01); *C12N 2506/28* (2013.01); *C12N 2506/45* (2013.01); *C12N 2510/00* (2013.01)

(58) Field of Classification Search
None
See application file for complete search history.

(56) References Cited

PUBLICATIONS

Park, M. et al., Cell Reports, 2018, vol. 23: pp. 2467-2481.*
Sizemore, G. et al., Nature Rev. Cancer, 2017, vol. 17: pp. 337-351.*
Uenishi, G. et al., Nat. Communications, 2018, vol. 9, pp. 1-14.*
Ayllon, V. et al. The Notch ligand DLL4 specifically marks human hematoendothelial progenitors and regulates their hematopoietic fate. Leukemia 29, 1741-1753 (2015).
Bertrand, J.Y. et al. Characterization of purified intraembryonic hematopoietic stem cells as a tool to define their site of origin. Proc Natl Acad Sci U S A 102, 134-139. Epub Dec. 2004 2027. (2005).
Bigas, A., et al. (2012). The Notch pathway in hematopoietic stem cells. CurrTop Microbiol Immunol 360, 1-18.
Bigas, A., et al. (2012). Hematopoietic stem cells: to be or Notch to be. Blood 119, 3226-3235.
Bovolenta, L.A., Acencio, M.L. & Lemke, N. HTRIdb: an open-access database for experimentally verified human transcriptional regulation interactions. BMC Genomics 13, 405 (2012).
Burns, C.E. et al. A genetic screen in zebrafish defines a hierarchical network of pathways required for hematopoietic stem cell emergence. Blood 113, 5776-5782 (2009).
Butko, E., et al. (2016). Complex regulation of HSC emergence by the Notch signaling pathway. Dev Biol 409, 129-138.
Cahan, P. et al. CellNet: network biology applied to stem cell engineering. Cell 158, 903-915 (2014).
Choi, K. et al. Hematopoietic and endothelial differentiation of human induced pluripotent stem cells. Stem Cells 27, 559-567 (2009).
Choi, K, et al. "Hematopoietic differentiation and production of mature myeloid cells from human pluripotent stem cells." Nature protocols 6.3 (2011): 296-313.
Choi, K.-D. et al. Identification of the Hemogenic Endothelial Progenitor and Its Direct Precursor in Human Pluripotent Stem Cell Differentiation Cultures Cell Rep 2, 553-567 (2012).
Chong, D.C., et al. Stepwise arteriovenous fate acquisition during mammalian vasculogenesis. Dev Dyn 240, 2153-2165 (2011).
Corada, M. et al. Sox17 is indispensable for acquisition and maintenance of arterial identity. Nat Commun 4, 2609 (2013).
De Bruijn, M.F., et al. Definitive hematopoietic stem cells first develop within the major arterial regions of the mouse embryo. The EMBO journal 19, 2465-2474 (2000).
Dias, J. et al. Generation of red blood cells from human induced pluripotent stem cells. Stem Cells Dev 20, 1639-1647 (2011).
Ditadi, A. et al. Human definitive haemogenic endothelium and arterial vascular endothelium represent distinct lineages. Nat Cell Biol 17, 580-591 (2015).
Dou, D.R. et al. Medial HOXA genes demarcate haematopoietic stem cell fate during human development. Nat Cell Biol 18, 595-606 (2016).
Duarte, A. et al. Dosage-sensitive requirement for mouse DII4 in artery development. Genes Dev 18, 2474-2478 (2004).
Espin-Palazon, R. et al. Proinflammatory signaling regulates hematopoietic stem cell emergence. Cell 159, 1070-1085 (2014).
Frame, J.M., et al. Definitive Hematopoiesis in the Yolk Sac Emerges from Wnt-Responsive Hemogenic Endothelium Independently of Circulation and Arterial Identity. Stem Cells 34, 431-444 (2016).

(Continued)

*Primary Examiner* — Michael D Burkhart
(74) *Attorney, Agent, or Firm* — Quarles & Brady LLP

(57) ABSTRACT

The present invention is a method of creating a population of hemogenic endothelial cells with arterial specification and enhanced T cell potential. In one embodiment, the method uses ETS transgene induction at the mesodermal stage of differentiation. In another embodiment, the method activates ERK and NOTCH signaling at the mesodermal stage of differentiation.

9 Claims, 35 Drawing Sheets
(28 of 35 Drawing Sheet(s) Filed in Color)
Specification includes a Sequence Listing.

(56) References Cited

PUBLICATIONS

Gale, N.W. et al. Haploinsufficiency of delta-like 4 ligand results in embryonic lethality due to major defects in arterial and vascular development. Proc Natl Acad Sci U S A 101, 15949-15954 (2004).
Gering, M. et al. Hedgehog signaling is required for adult blood stem cell formation in zebrafish embryos. Dev Cell 8, 389-400 (2005).
Goldie, L.C., et al. Cell signaling directing the formation and function of hemogenic endothelium during murine embryogenesis Blood 112, 3194-3204 (2008).
Gordon-Keylock, S., et al. Mouse extraembryonic arterial vessels harbor precursors capable of maturing into definitive HSCs. Blood 122, 2338-2345 (2013).
Hadland et al., Endothelium and NOTCH specify and amplify aorta-gonad-mesonephros-derived hematopoietic stem cells, J Clin Invest, 2015, 125(5):2032-2045.
Hadland, B.K. et al. A Common Origin for B-1a and B-2 Lymphocytes in Clonal Pre-Hematopoietic Stem Cells. Stem cell reports 8, 1563-1572 (2017).
Herbert, S.P. et al. Arterial-venous segregation by selective cell sprouting: an alternative mode of blood vessel formation. Science 326, 294-298 (2009).
Hong, C.C., et al. Artery/vein specification is governed by opposing phosphatidylinositol-3 kinase and MAP kinase/ERK signaling. Curr Biol 16, 1366-1372 (2006).
Hou, Z. et al. A cost-effective RNA sequencing protocol for large-scale gene expression studies. Sci Rep 5, 9570 (2015).
Hu, Y. & Smyth, G.K. Elda: extreme limiting dilution analysis for comparing depleted and enriched populations in stem cell and other assays. J Immunol Methods 347, 70-78 (2009).
Kennedy, M., et al. Development of the hemangioblast defines the onset of hematopoiesis in human ES cell differentiation cultures Blood 109, 2679-2687. (2007).
Kennedy, M. et al. T lymphocyte potential marks the emergence of definitive hematopoietic progenitors in human pluripotent stem cell differentiation cultures. Cell Rep 2, 1722-1735 (2012).
Kim, P.G. et al. Signaling axis involving Hedgehog, Notch, and Scl promotes the embryonic endothelial-to-hematopoietic transition. Proc Natl Acad Sci U S A 110, E141-150 (2013).
Kim, I., et al. Sox17 dependence distinguishes the transcriptional regulation of fetal from adult hematopoietic stem cells. Cell 130, 470-483 Epub Jul. 2007 2026. (2007).
Kumar, A., et al. NOTCH activation at the definitive mesoderm stage facilitates efficient generation of T cells with high proliferation potential from Human Pluripotent Stem Cells. American Society of Hematology 59th Annual Meeting, 2017, Poster Abstract.
Langmead B, et al. Ultrafast and memory-efficient alignment of short DNA sequences to the human genome. Genome Biology. 2009;10(3):R25. doi:10.1186/gb-2009-10-3-r25.
Lawson, N.D., et al. sonic hedgehog and vascular endothelial growth factor act upstream of the Notch pathway during arterial endothelial differentiation. Dev Cell 3, 127-136 (2002).
Lawson, N.D. et al. Notch signaling is required for arterial-venous differentiation during embryonic vascular development. Development 128, 3675-3683 (2001).
Ledran, M.H. et al. Efficient hematopoietic differentiation of human embryonic stem cells on stromal cells derived from hematopoietic niches. Cell Stem Cell 3, 85-98. (2008).
Leng, N. et al. EBSeq: an empirical Bayes hierarchical model for inference in RNA-seq experiments. Bioinformatics 29, 1035-1043 (2013).
Li, W., et al. Endothelial cells in the early murine yolk sac give rise to CD41-expressing hematopoietic cells. Stem Cells Dev 14, 44-54. (2005).
Li B, Dewey CN. RSEM: accurate transcript quantification from RNA-Seq data with or without a reference genome. BMC Bioinformatics. 2011;12:323. doi:10.1186/1471-2105-12-323.
Li, Y. et al. Inflammatory signaling regulates embryonic hematopoietic stem and progenitor cell production. Genes Dev 28, 2597-2612 (2014).
Lin, Y., et al. Lymphoid progenitor emergence in the murine embryo and yolk sac precedes stem cell detection. Stem Dells Dev 23, 1168-1177 (2014).
Lu, YF., et al. (2016) Engineered Murine HSCs Reconstitute Multi-lineage Hematopoiesis and Adaptive Immunity. Cell Report 17, 3178-3192.
McKinney-Freeman, S. et al. The transcriptional landscape of hematopoietic stem cell ontogeny. Cell Stem Cell 11, 701-714 (2012).
Medvinsky, A., et al. Embryonic origin of the adult hematopoietic system: advances and questions. Development 138, 1017-1031 (2011).
Monteiro, R. et al. Transforming Growth Factor beta Drives Hemogenic Endothelium Programming and the Transition to Hematopoietic Stem Cells. Dev Cell (2016).
Ng, E.S. et al. Differentiation of human embryonic stem cells to HOXA+ hemogenic vasculature that resembles the aorta-gonad-mesonephros. Nat Biotechnol (2016).
North, T. et al. Cbfa2 is required for the formation of intra-aortic hematopoietic clusters. Development 126, 2563-2575 (1999).
Ohishi et al., Delta-1 enhances marrow and thymus repopulating ability of human CD34+ CD38- cord blood cells, J Clin Invest. 2002;110(8):1165-1174.
Ohishi et al., The NOTCH pathway: Modulation of cell fate decisions in hematopoiesis, Int. J. Hema, 75(5):449-459.
Rahman, N. et al. Engineering the haemogenic niche mitigates endogenous inhibitory signals and controls pluripotent stem cell-derived blood emergence. Nat Commun 8, 15380 (2017).
Richard, C. et al. Endothelio-mesenchymal interaction controls runx1 expression and modulates the notch pathway to initiate aortic hematopoiesis. Dev Cell 24, 600-611 (2013).
Robert-Moreno, A. et al. Impaired embryonic haematopoiesis yet normal arterial development in the absence of the Notch ligand Jagged1. EMBO J 27, 1886-1895 (2008).
Rybtsov, S., et al. Concealed expansion of immature precursors underpins acute burst of adult HSC activity in foetal liver. Development 143, 1284-1289 (2016).
Sacilotto, N. et al. Analysis of Dll4 regulation reveals a combinatorial role for Sox and Notch in arterial development. Proc Natl Acad Sci U S A 110, 11893-11898 (2013).
Salvagiotto, G. et al. Molecular profiling reveals similarities and differences between primitive subsets of hematopoietic cells generated in vitro from human embryonic stem cells and in vivo during embryogenesis. Experimental Hematology 36, 1377-1389 (2008).
Sankaran, V.G. et al. Human fetal hemoglobin expression is regulated by the developmental stage-specific repressor BCL11A. Science 322, 1839-1842 (2008).
Shannon, P. et al. Cytoscape: a software environment for integrated models of biomolecular interaction networks. Genome Res 13, 2498-2504 (2003).
Slukvin, II (2013). Hematopoietic specification from human pluripotent stem cells: current advances and challenges toward de novo generation of hematopoietic stem cells. Blood 122, 4035-4046.
Slukvin, II (2016). Generating human hematopoietic stem cells in vitro—exploring endothelial to hematopoietic transition as a portal for stemness acquisition. FEBS Lett.
Sugimura, R. et al. Haematopoietic stem and progenitor cells from human pluripotent stem cells. Nature 545, 432-438 (2017).
Tober, J., et al. Taking the Leap: Runx1 in the Formation of Blood from Endothelium. Curr Top Dev Biol 118, 113-162 (2016).
Uenishi, G. et al. Tenascin C promotes hematoendothelial development and T lymphoid commitment from human pluripotent stem cells in chemically defined conditions. Stem cell reports 3, 1073-1084 (2014).
Villa, N. et al. Vascular expression of Notch pathway receptors and ligands is restricted to arterial vessels. Mech Dev 108, 161-164 (2001).
Vizcardo, R. et al. Regeneration of human tumor antigen-specific T cells from iPSCs derived from mature CD8(+) T cells. Cell Stem Cell 12, 31-36 (2013).
Vo, L.T.,et al (2015). De novo generation of HSCs from somatic and pluripotent stem cell sources. Blood 125, 2641-2648.

(56) References Cited

PUBLICATIONS

Vodyanik, Maxim A., et al. "Human embryonic stem cell-derived CD34+ cells: efficient production in the coculture with OP9 stromal cells and analysis of lymphohematopoietic potential." Blood 105.2 (2005): 617-626.

Vodyanik, M.A., et al. Leukosialin (CD43) defines hematopoietic progenitors in human embryonic stem cell differentiation cultures. Blood 108, 2095-2105 (2006).

Vodyanik, M.A. et al. A mesoderm-derived precursor for mesenchymal stem and endothelial cells. Cell Stem Cell 7, 718-729 (2010).

Wang, L. et al. Generation of hematopoietic repopulating cells from human embryonic stem cells independent of ectopic HOXB4 expression. J Exp Med 201, 1603-1614. Epub May 2005 1609. (2005).

Wythe, J.D. et al. ETS factors regulate Vegf-dependent arterial specification. Dev Cell 26, 45-58 (2013).

Yamamizu, K. et al. Convergence of Notch and beta-catenin signaling induces arterial fate in vascular progenitors. J Cell Biol 189, 325-338 (2010).

Yurugi-Kobayashi, T. et al. Adrenomedullin/cyclic AMP pathway induces Notch activation and differentiation of arterial endothelial cells from vascular progenitors. Arterioscler Thromb Vasc Biol 26, 1977-1984 (2006).

Yzaguirre, A.D. et al. Insights into blood cell formation from hemogenic endothelium in lesser-known anatomic sites. Dev Dyn (2016).

\* cited by examiner

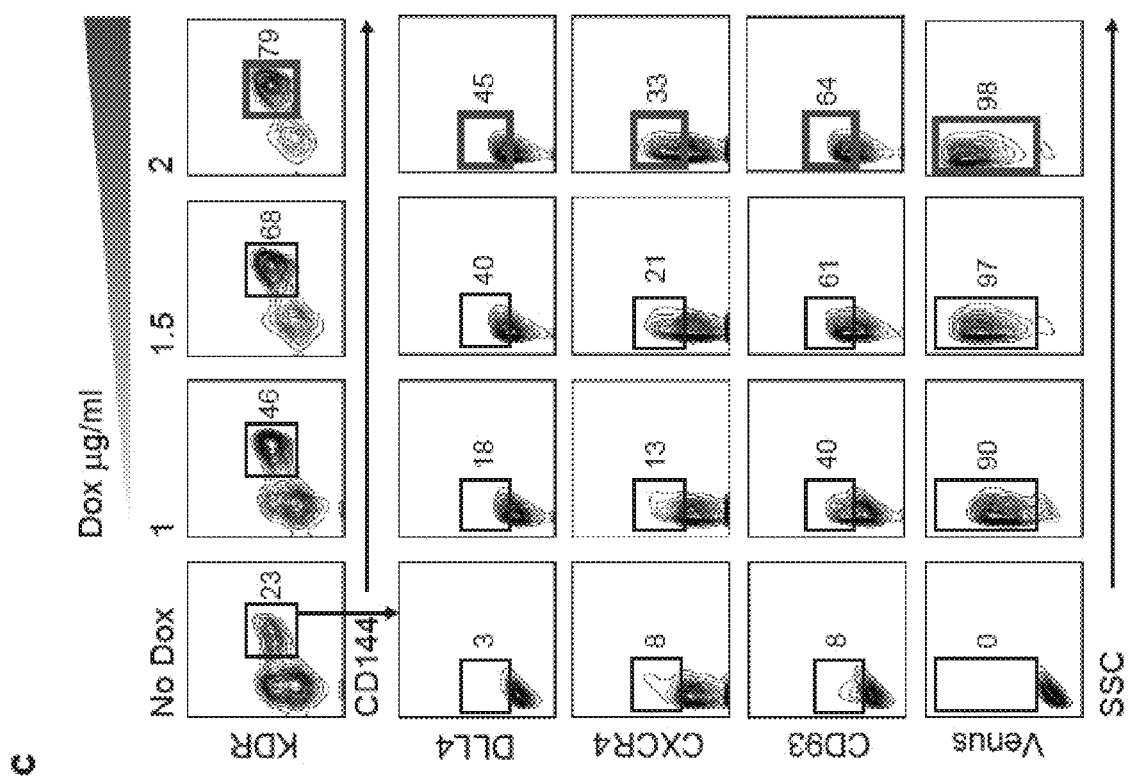
FIGS. 1A-1E, CONTINUED

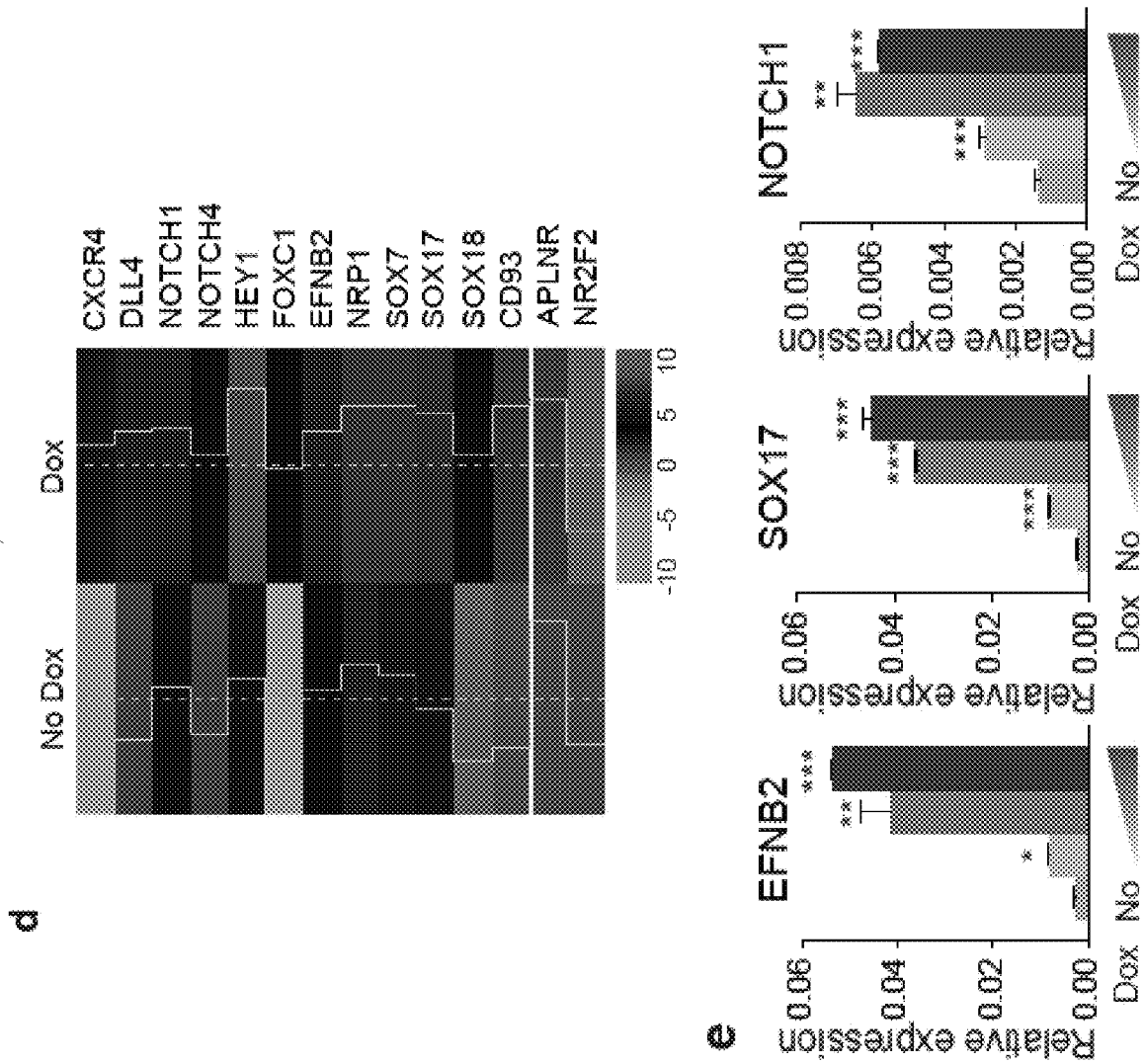
FIGS. 1A-1E, CONTINUED

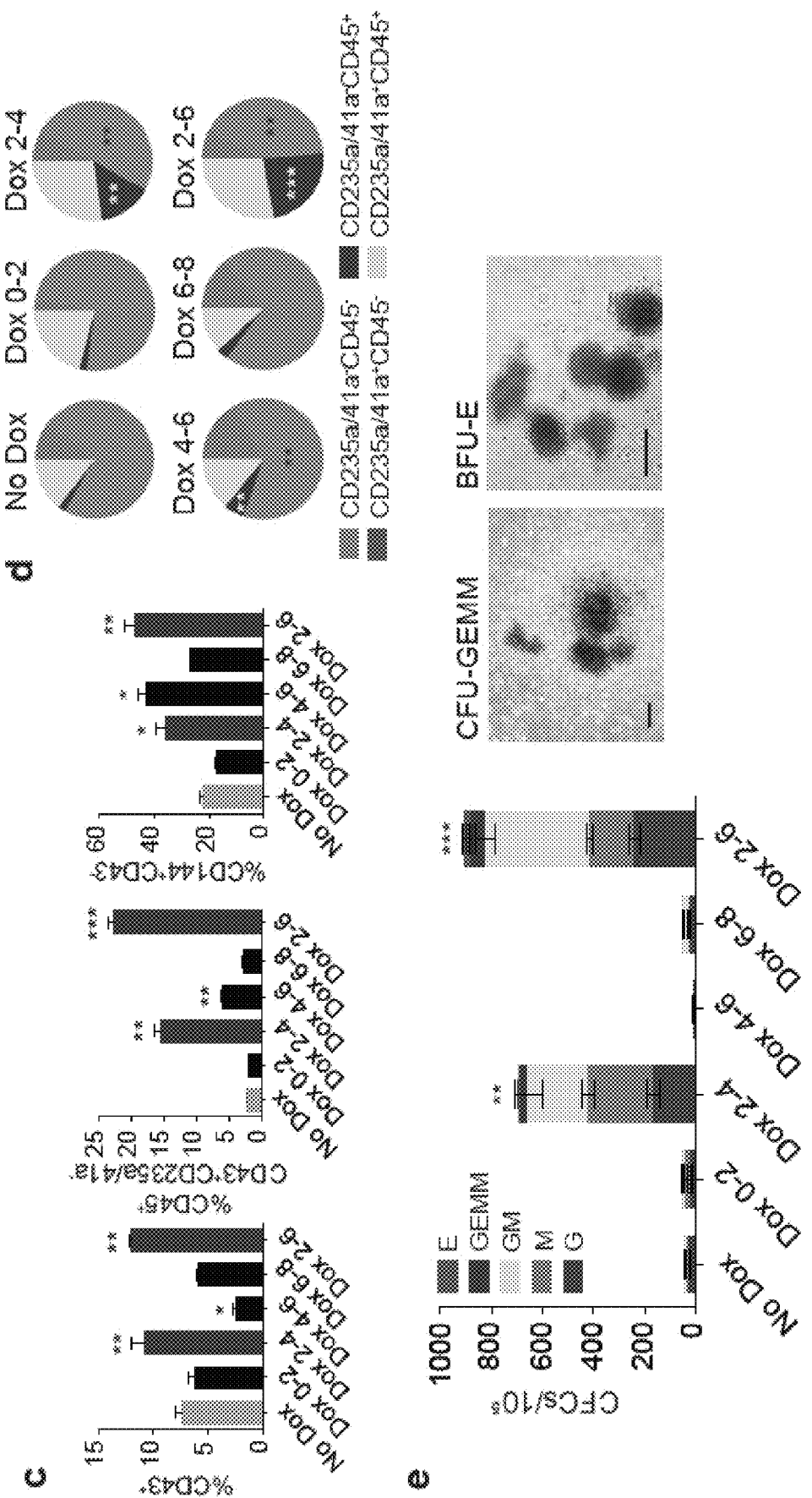
FIGS. 2A-2E, CONTINUED

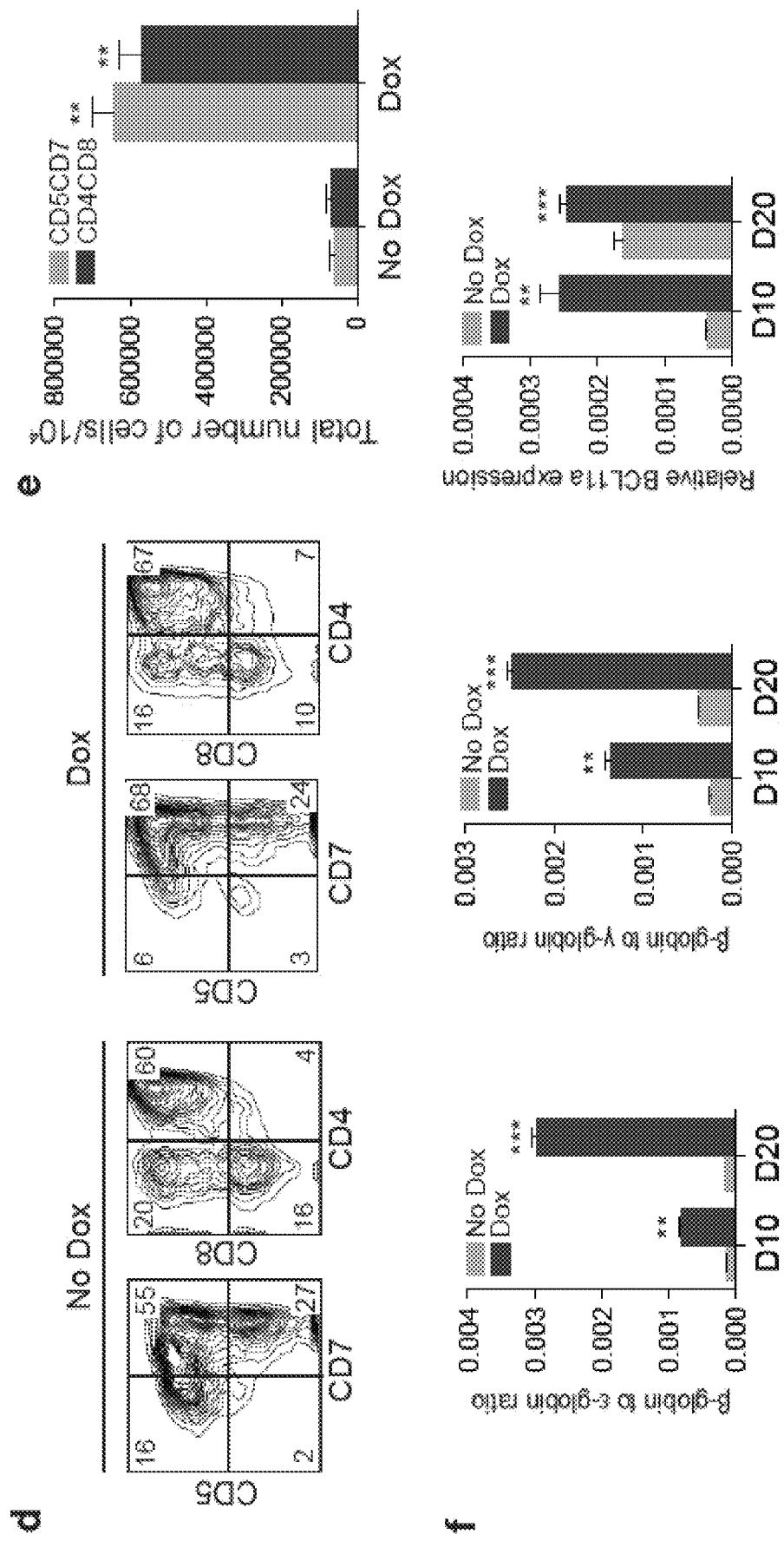
FIGS. 3A-3F, CONTINUED

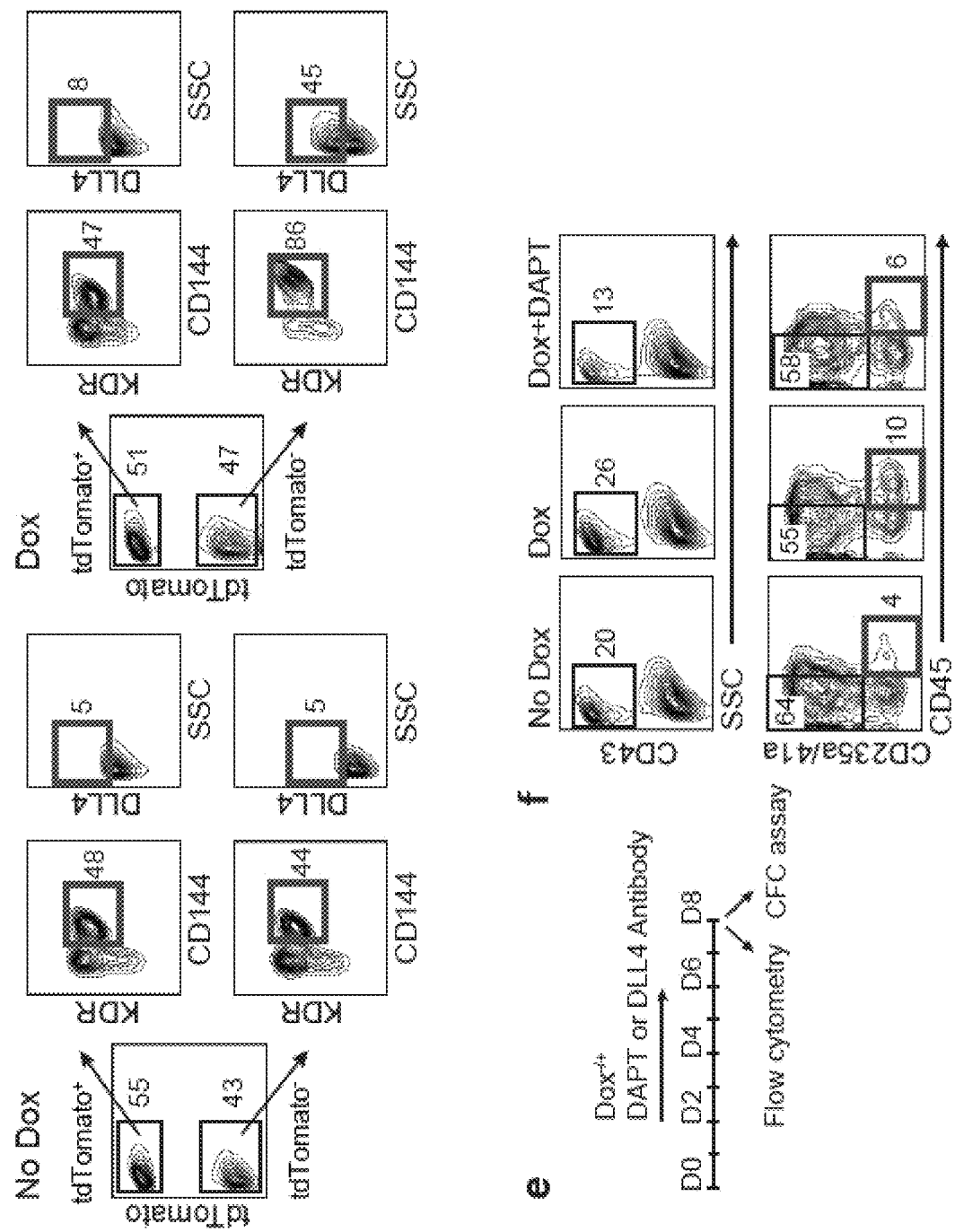
FIGS. 4A-4I, CONTINUED

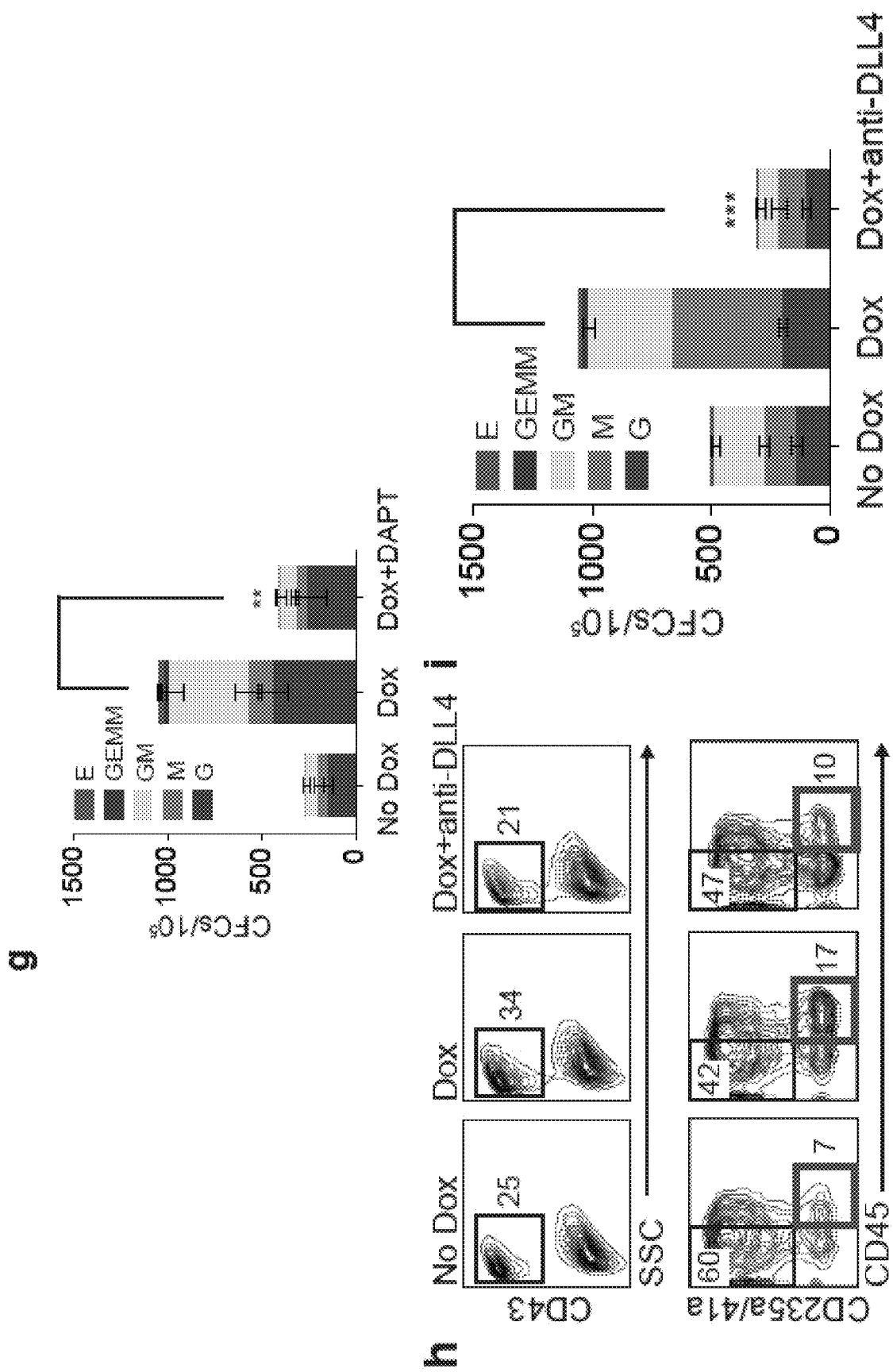
FIGS. 4A-4I, CONTINUED

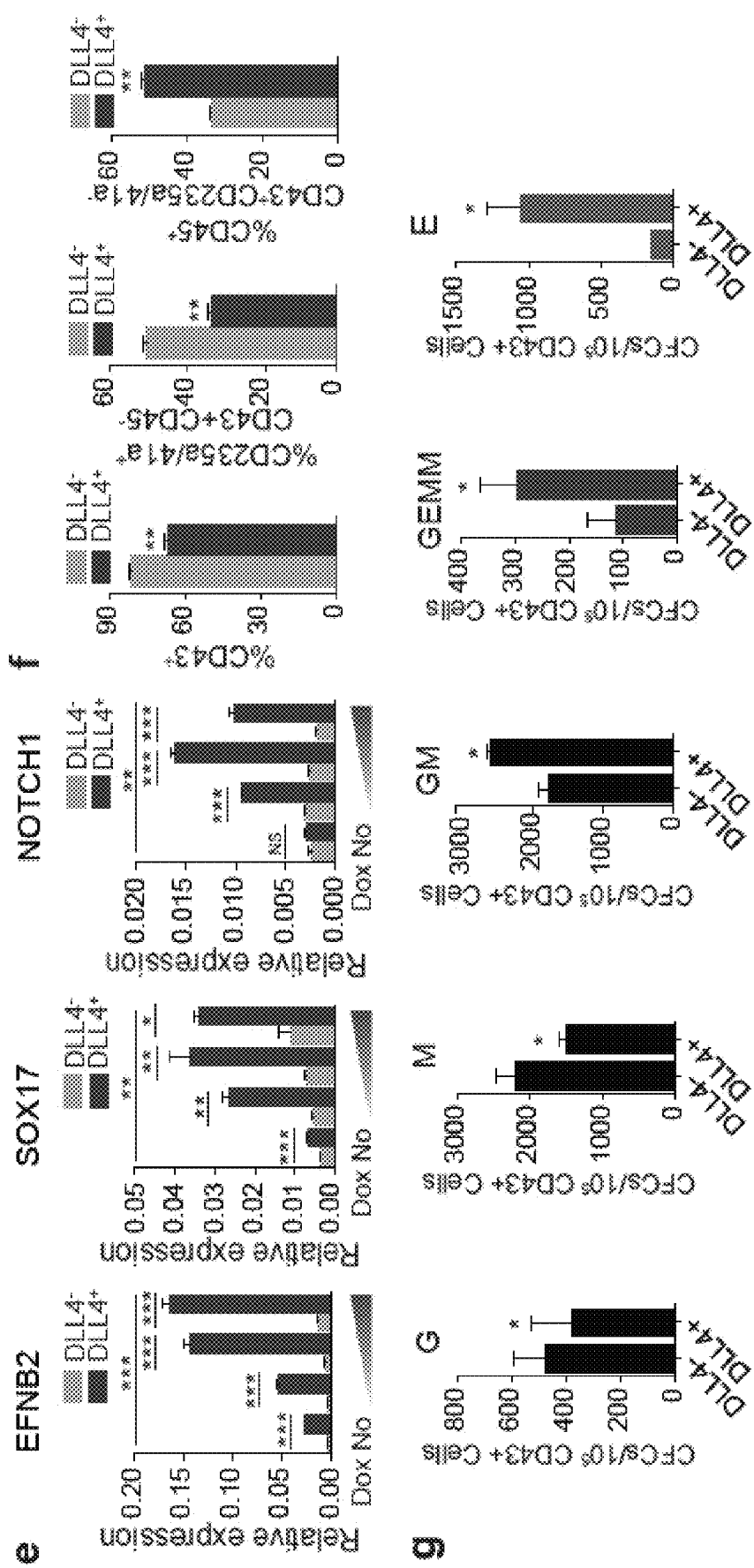
FIGS. 5A-5K, CONTINUED

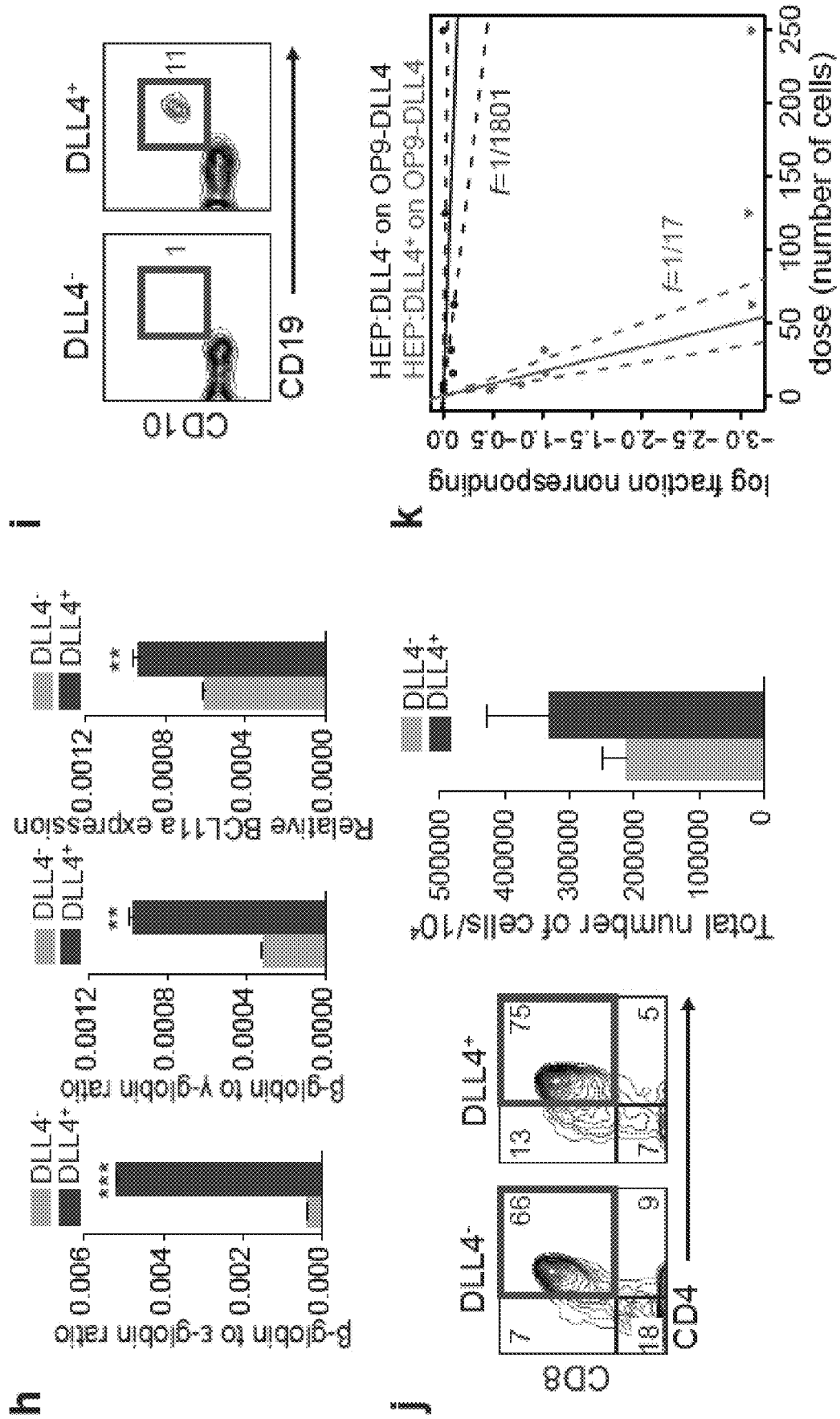
FIGS. 5A-5K, CONTINUED

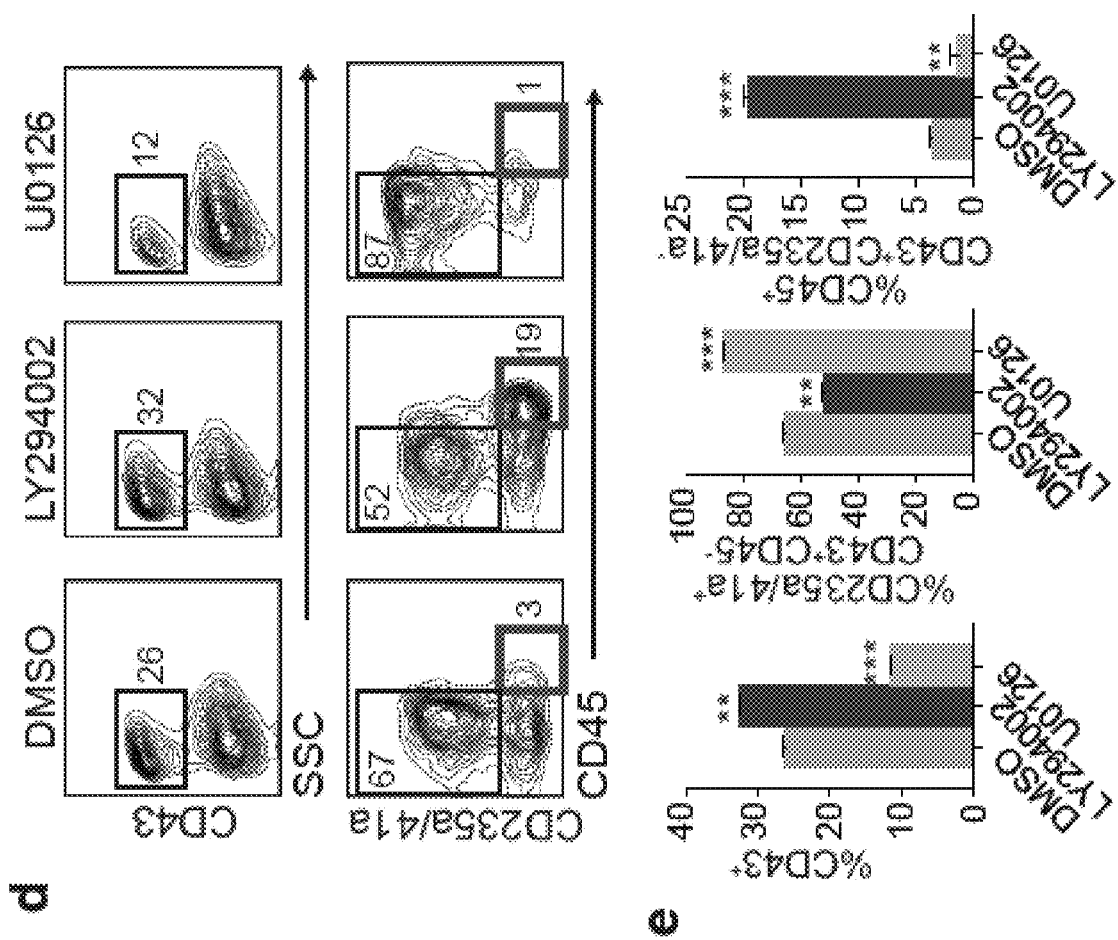
FIGS. 6A-6H, CONTINUED

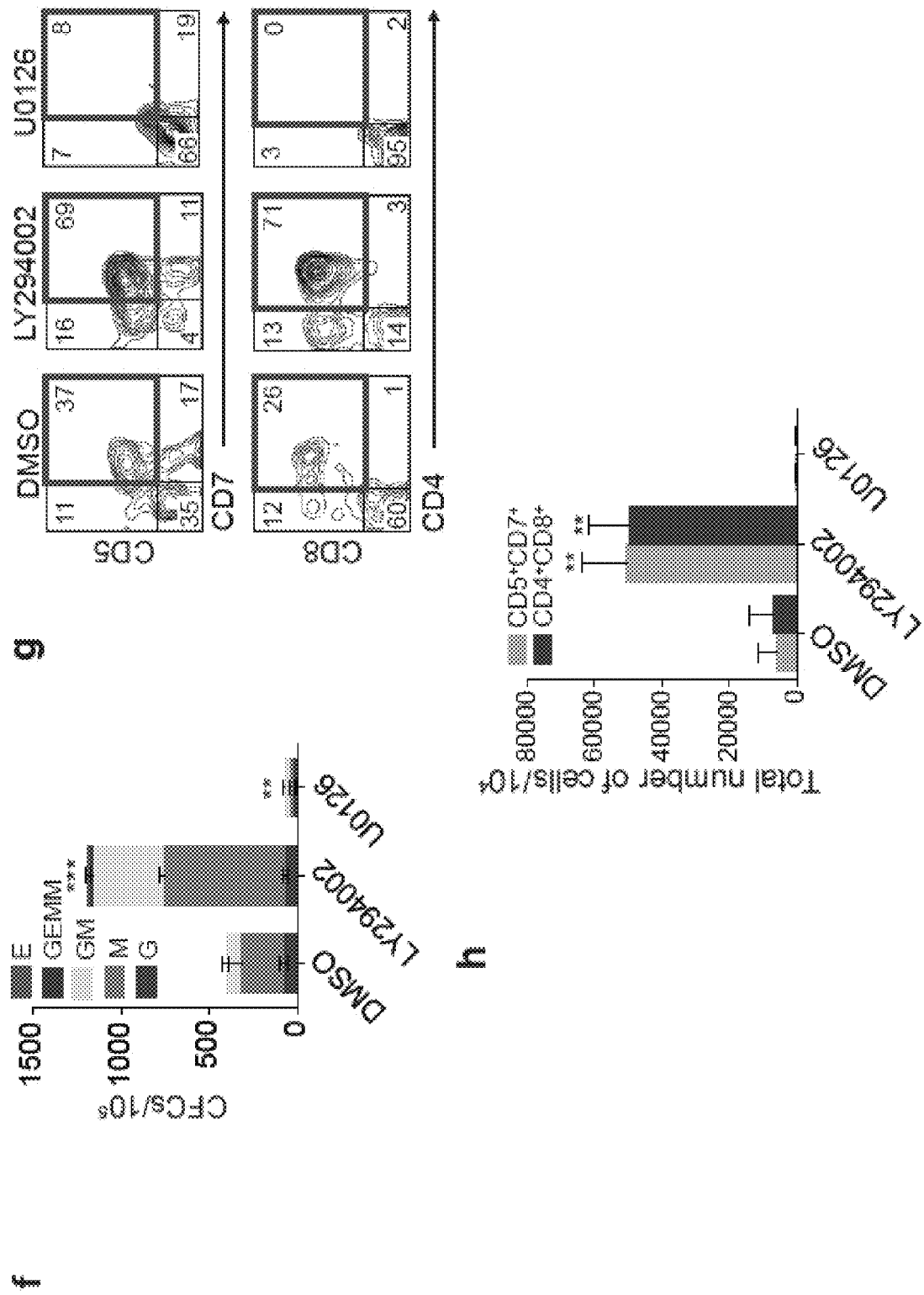
FIGS. 6A-6H, CONTINUED

FIGS. 7A-7B, CONTINUED
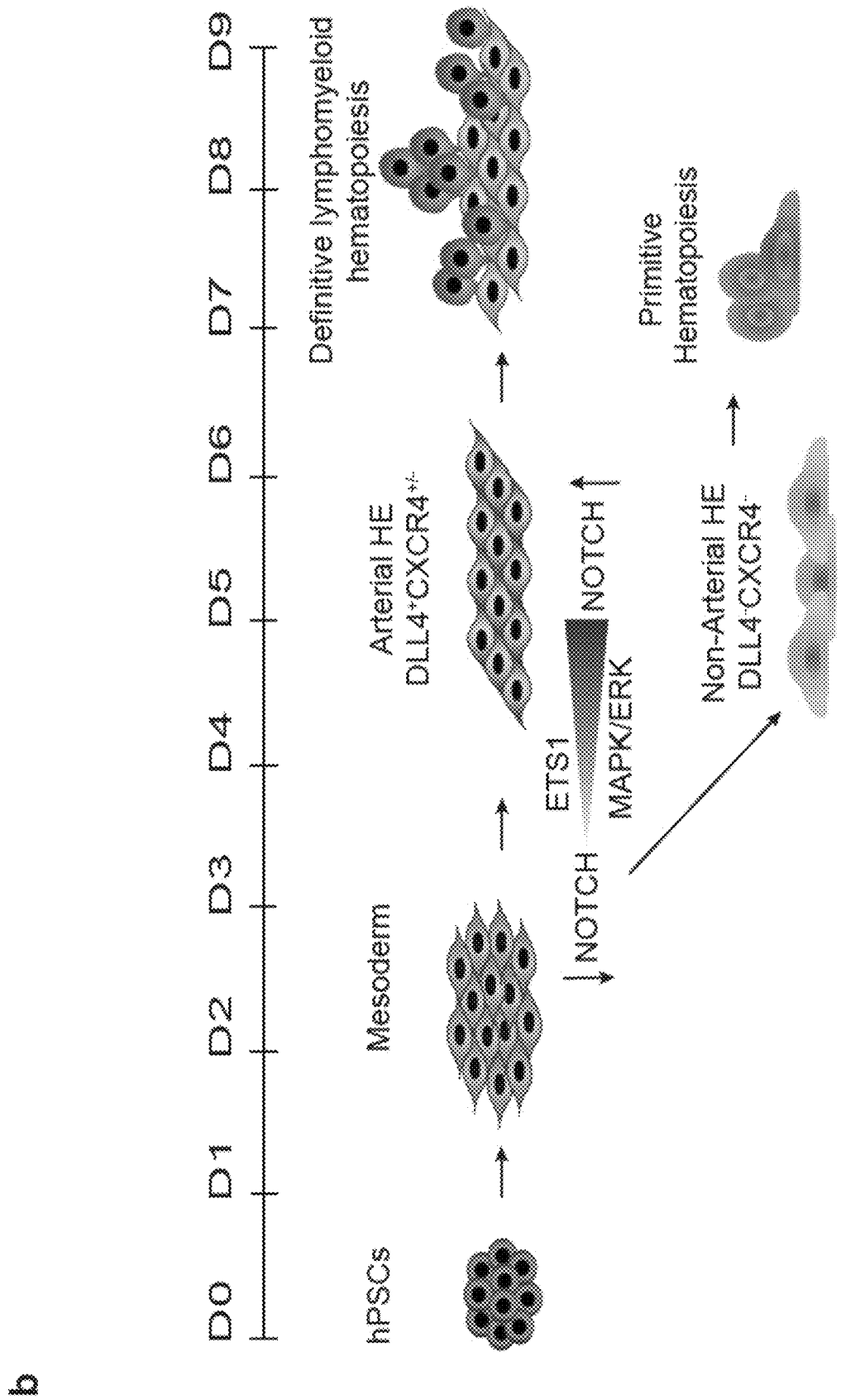

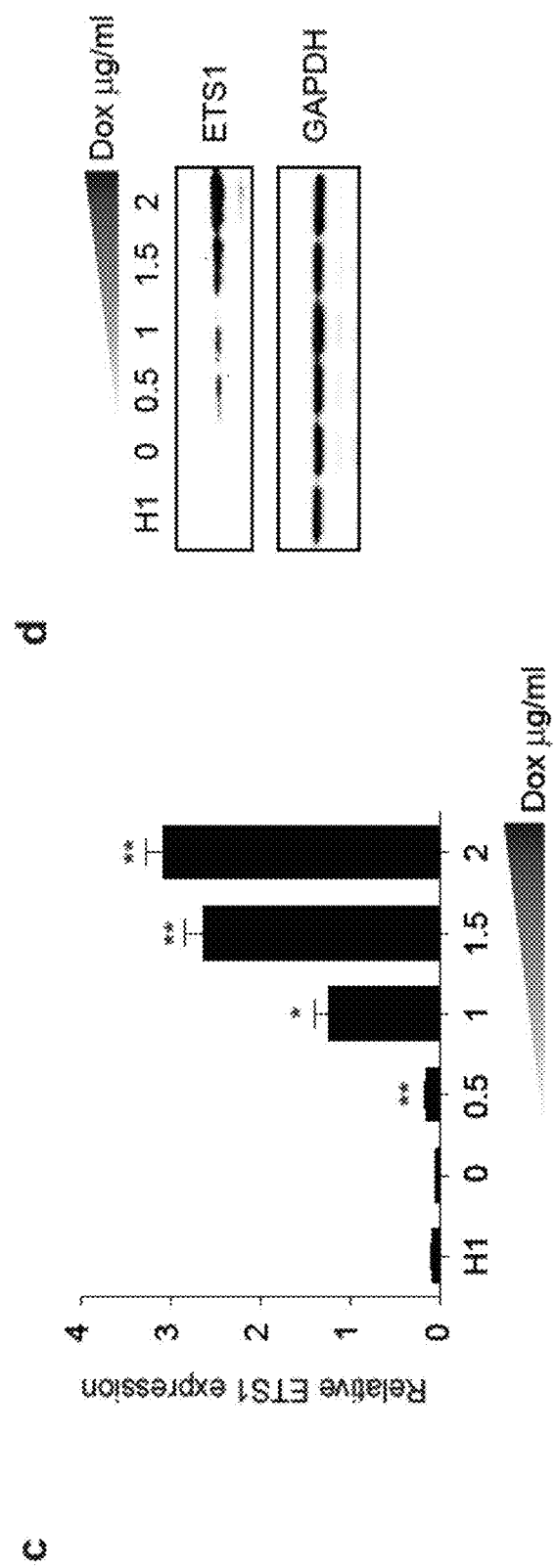
FIGS. 8A-8D, CONTINUED a b c

FIGS. 11A-11E
a
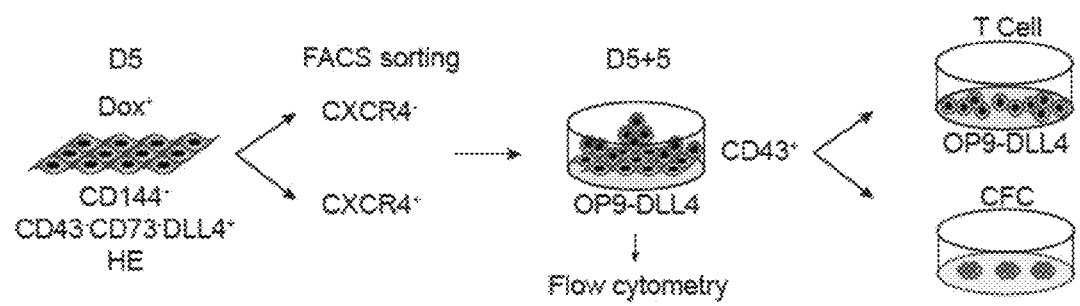
b
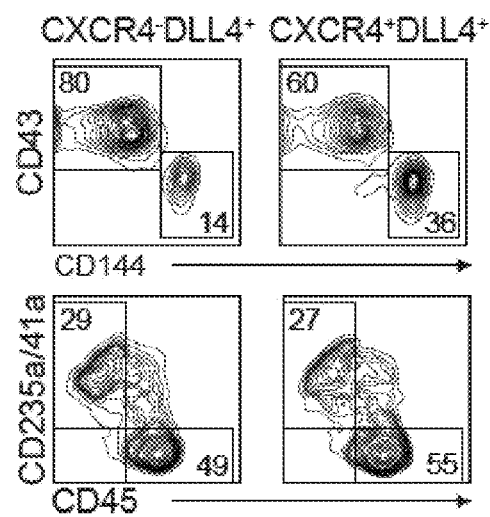

FIGS. 11A-11E, CONTINUED
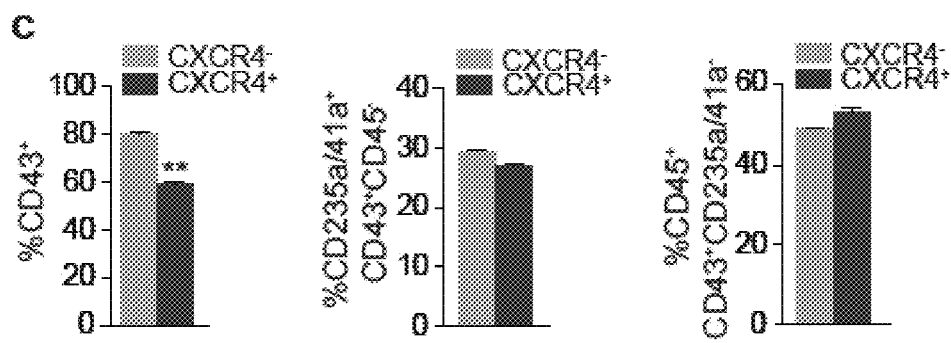
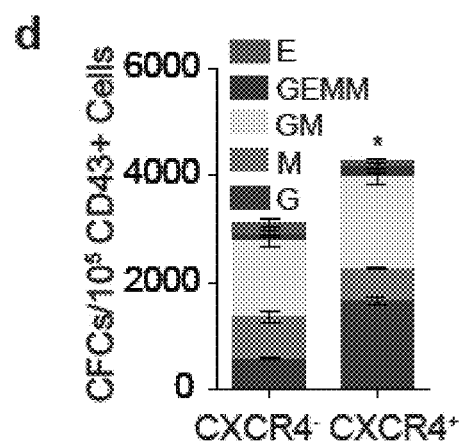
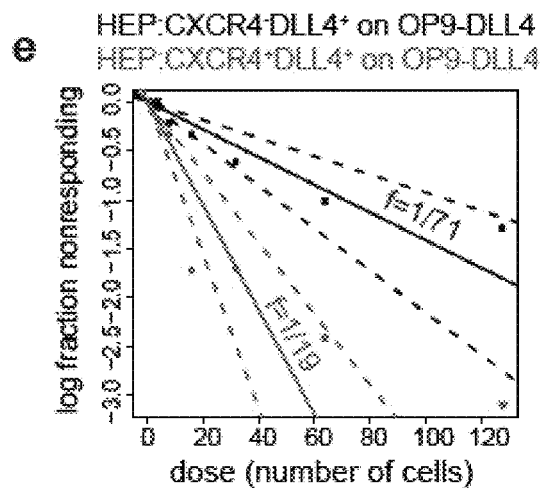

FIG. 12

Supplementary Table S1. List of antibodies used for FACS

| Antigen | Label | Company | Cat. Number |
|---|---|---|---|
| CD4 | APC | BD Biosciences | 555349 |
| CD5 | PE | BD Biosciences | 555353 |
| CD7 | FITC | BD Biosciences | 555360 |
| CD8 | PE | BD Biosciences | 555635 |
| CD10 | PE | BD Biosciences | 555375 |
| CD19 | APC | Miltenyi Biotec | 130-091-248 |
| CD34 | PE | BD Biosciences | 555822 |
| CD41a | PE | BD Biosciences | 555467 |
| CD41a | PE | Miltenyi Biotec | 130-105-580 |
| CD41a | APC | BD Biosciences | 559777 |
| CD43 | PE | BD Biosciences | 560199 |
| CD43 | APC | BD Biosciences | 560198 |
| CD43 | APC-Vio770 | Miltenyi Biotec | 130-101-174 |
| CD43 | BV421 | BD Biosciences | 562916 |
| CD45 | PerCP-Cy5.5 | BD Biosciences | 564105 |
| CD45 | APC | BD Biosciences | 555485 |
| CD45 | PE-Vio770 | Miltenyi Biotec | 130-096-616 |
| CD45 | BV421 | BD Biosciences | 563879 |
| CD73 | PE | BD Biosciences | 550257 |
| CD73 | BV421 | BD Biosciences | 562430 |
| CD93 | PE | BioLegend | 336107 |
| CD144 | PE | Miltenyi Biotec | 130-100-714 |
| CD144 | PE-Vio770 | Miltenyi Biotec | 130-100-722 |
| CD144 | PerCP-Cy5.5 | BD Biosciences | 561566 |
| CD144 | PerCP-Vio700 | Miltenyi Biotec | 130-100-718 |
| CD144 | Alexa Fluor 647 | BD Biosciences | 561567 |
| CD144 | VioBlue | Miltenyi Biotec | 130-100-724 |
| CD235a | PE | BD Biosciences | 555570 |
| CD235a | APC | BD Biosciences | 551336 |
| KDR (CD309) | PE | BD Biosciences | 560494 |
| KDR (CD309) | Alexa Fluor 647 | BD Biosciences | 560495 |
| DLL4 | PE | Miltenyi Biotec | 130-096-567 |
| DLL4 | PE-Vio770 | Miltenyi Biotec | 130-101-587 |
| CXCR4 | APC | eBioscience | 17-9999-42 |
| PDGFα (CD140a) | PE | BD Biosciences | 556002 |
| APLNR | APC | R&D Systems | FAB856A |
| TRA-1-85 | APC | R&D Systems | FAB3195A |

FIG. 13

Supplementary Table S2. List of primers used for RT-qPCR

| Gene | Direction | Sequences (5'-3') |
|---|---|---|
| ETS1 | F | CATCCACAAGACAGCGGGG (SEQ ID NO:1) |
|  | R | CTCGTCGGCATCTGGCTTG (SEQ ID NO:2) |
| EFNB2 | F | CCAGCCTCAAAATCGTGGCCCG (SEQ ID NO:3) |
|  | R | TTTGATGGCCCGAAGCCACTCG (SEQ ID NO:4) |
| SOX17 | F | AGAATCCAGACCTGCACAAC (SEQ ID NO:5) |
|  | R | GCCGGTACTTGTAGTTGGG (SEQ ID NO:6) |
| NOTCH1 | F | CAATGTGGATGCCGCAGTTGTG (SEQ ID NO:7) |
|  | R | CAGCACCTTGGCGGTCTCGTA (SEQ ID NO:8) |
| β-globin | F | GGCACCTTTGCCACACTG (SEQ ID NO:9) |
|  | R | CACTGGTGGGGTGAATTCTT (SEQ ID NO:10) |
| ε-globin | F | GCCTGTGGAGCAAGATGAAT (SEQ ID NO:11) |
|  | R | GCGGGCTTGAGGTTGT (SEQ ID NO:12) |
| γ-globin | F | CTTCAAGCTCCTGGGAAATGT (SEQ ID NO:13) |
|  | R | GCAGAATAAAGCCTATCCTTGAAAG (SEQ ID NO:14) |
| BCL11a | F | AACCCCAGCACTTAAGCAAA (SEQ ID NO:15) |
|  | R | GGAGGTCATGATCCCCTTCT (SEQ ID NO:16) |
| RPL13a | F | CCTGGAGGAGAAGAGGAAAGAGA (SEQ ID NO:17) |
|  | R | TTGAGGACCTCTGTGTATTTGTCAA (SEQ ID NO:18) |

FIG. 14
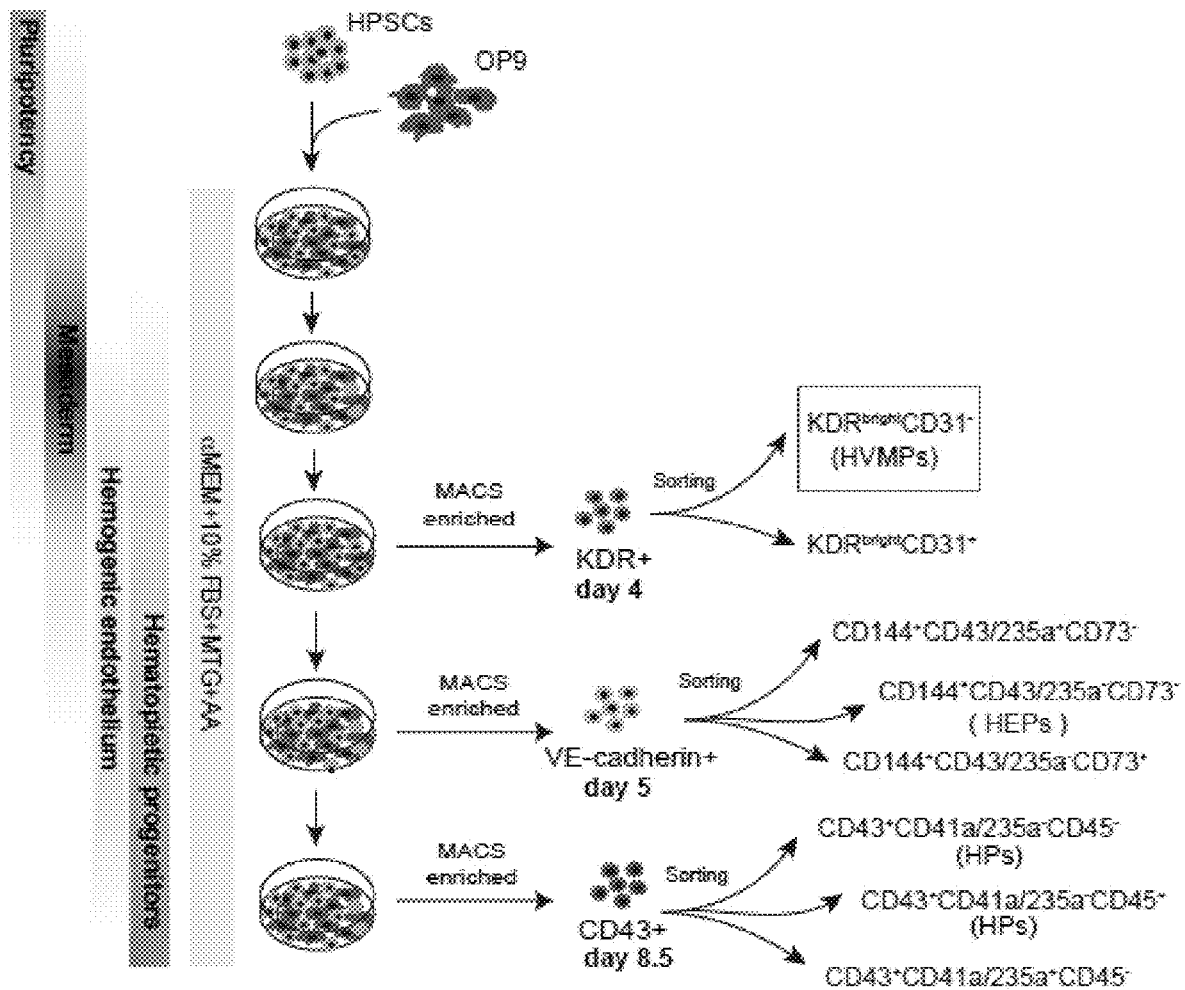
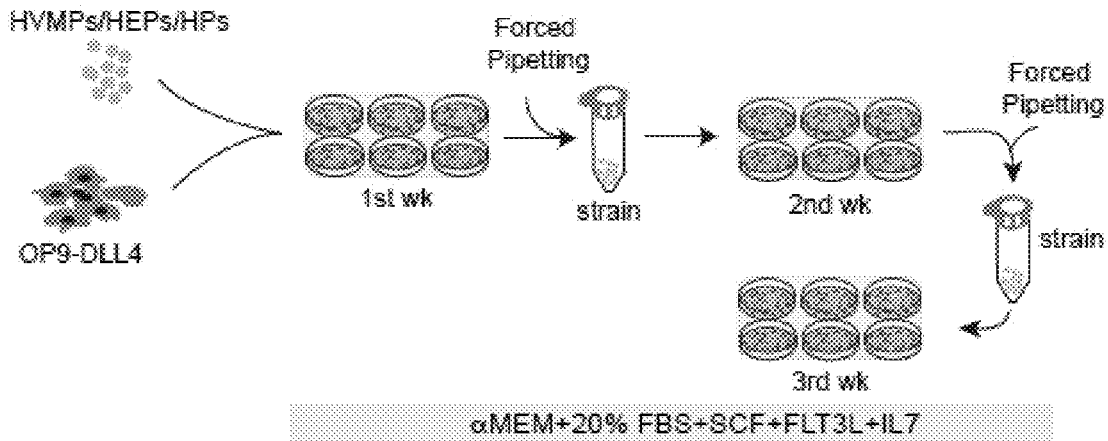

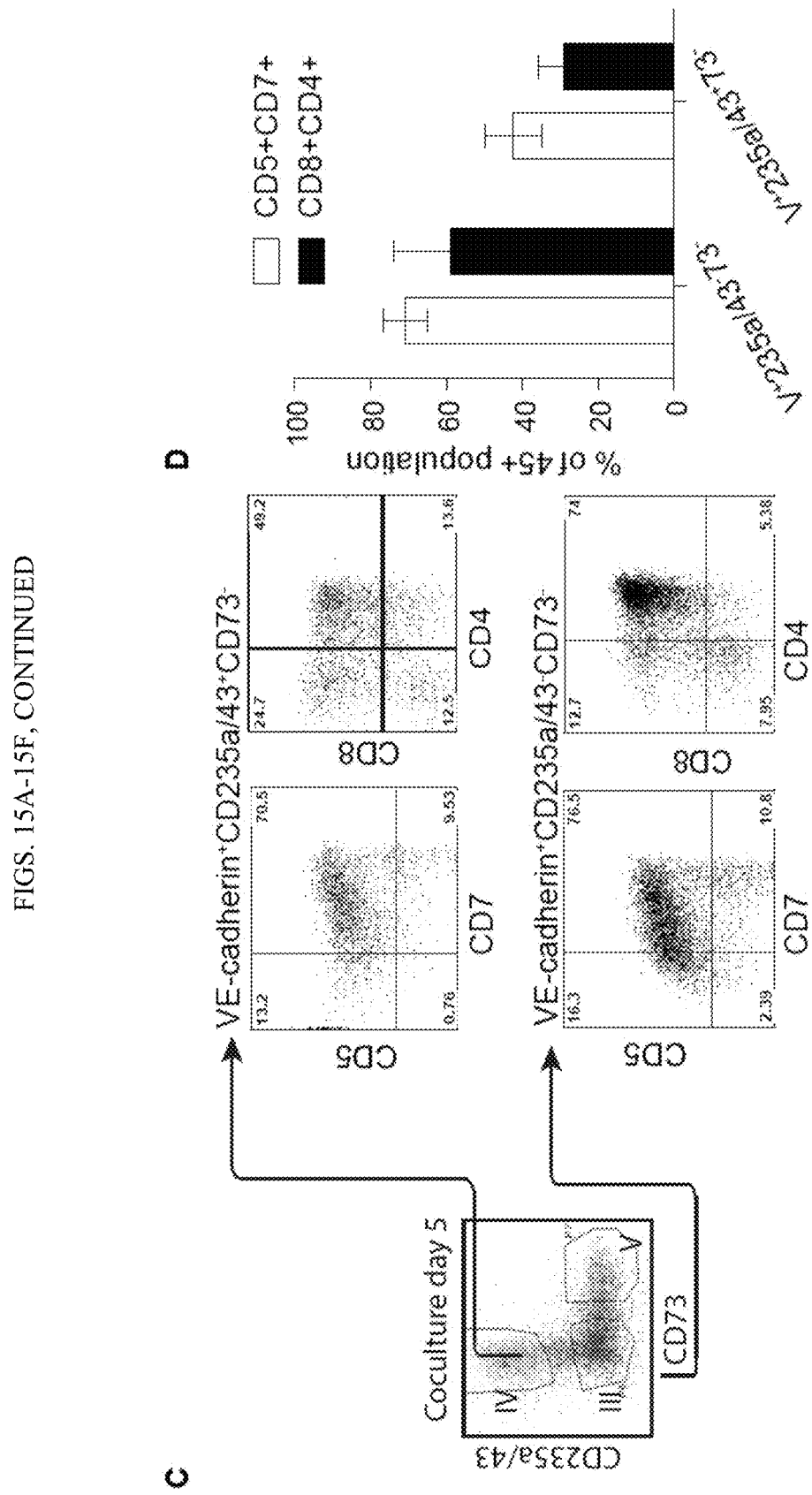
FIGS. 15A-15F, CONTINUED

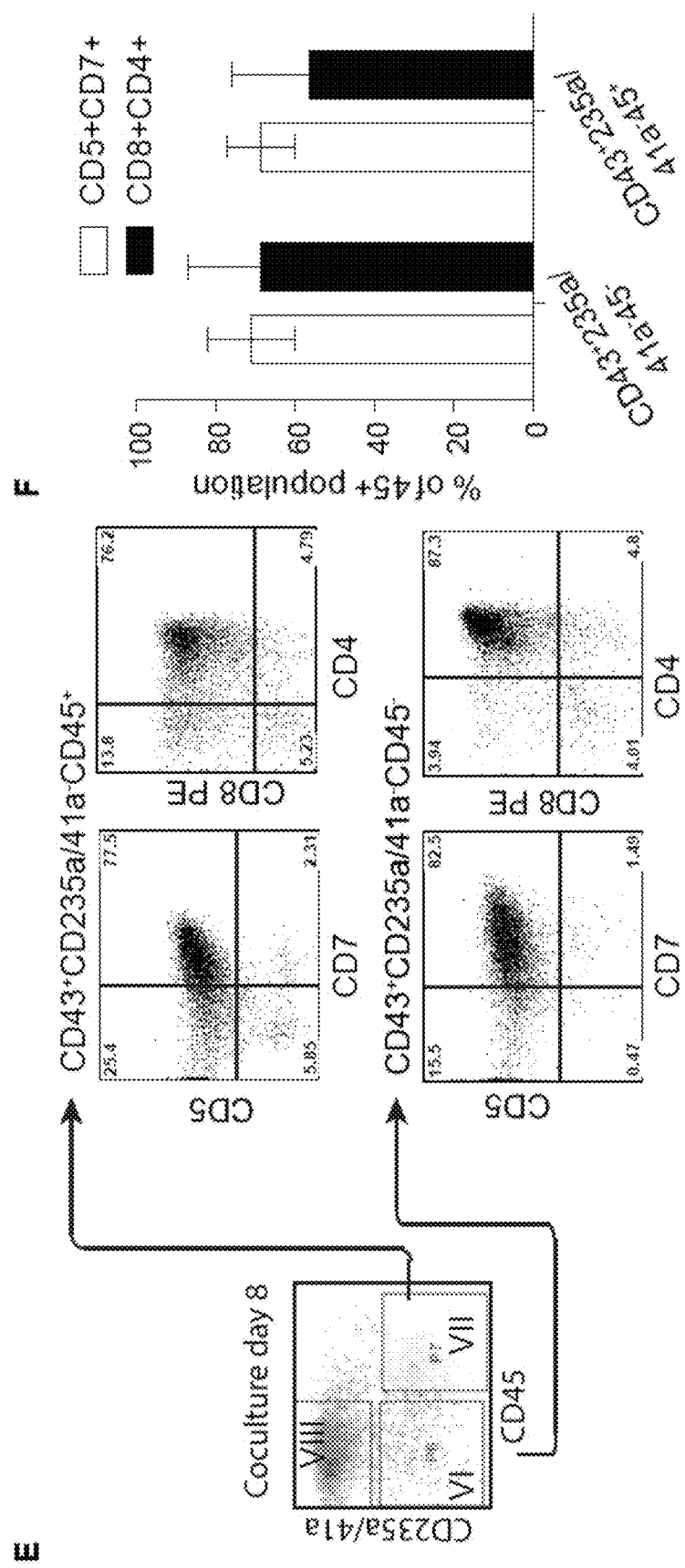
FIGS. 15A-15F, CONTINUED

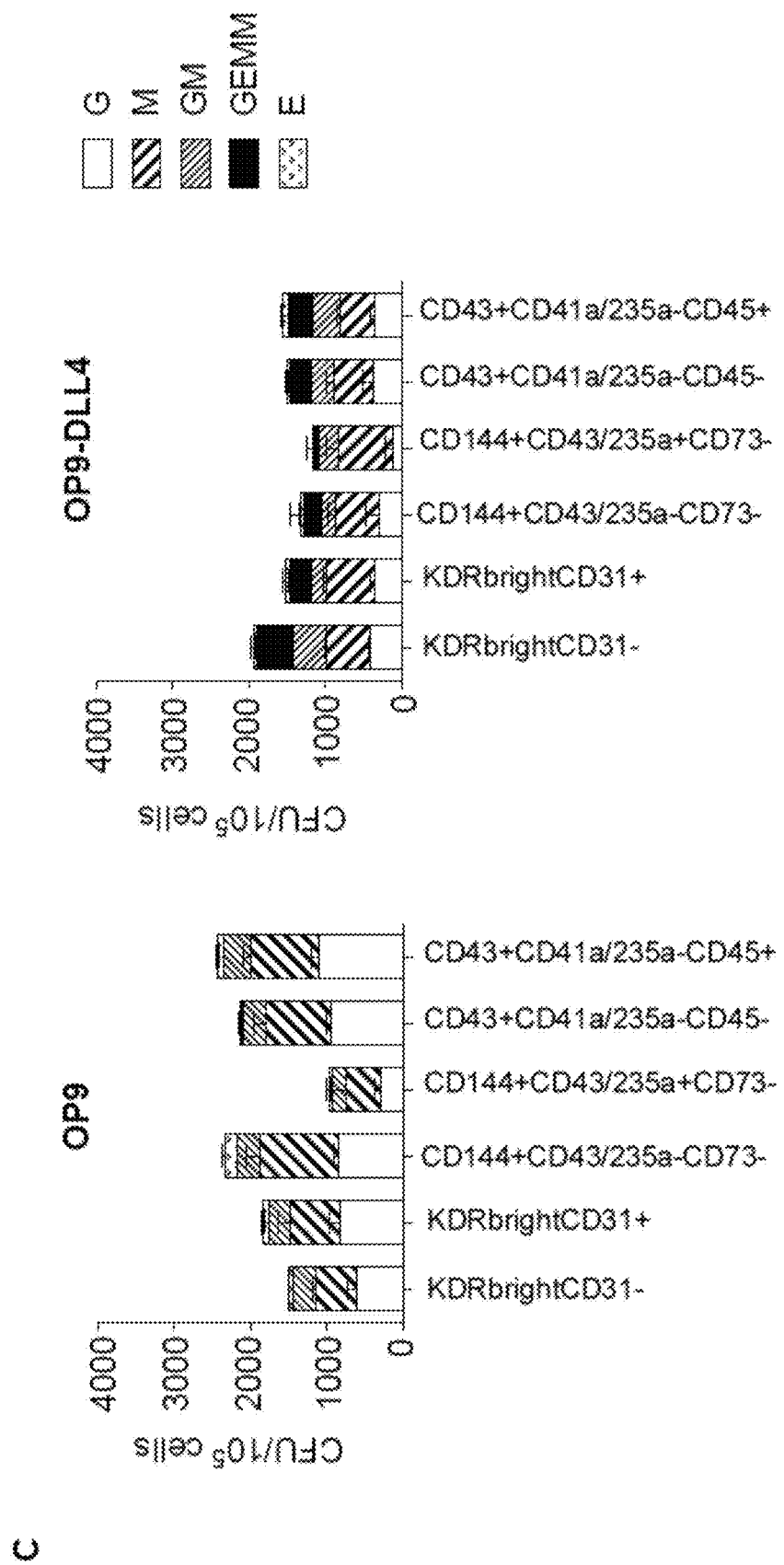
FIGS. 16A-16C, CONTINUED

FIGS. 18A-18C
A
Unstimulated
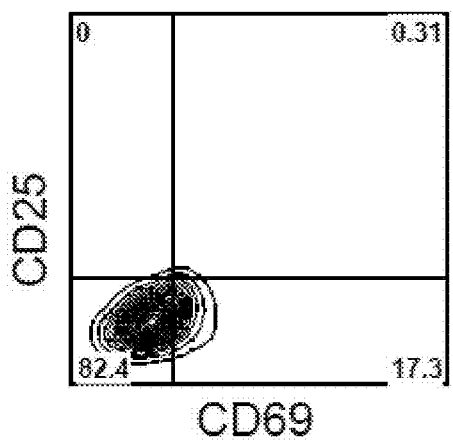
Stimulated
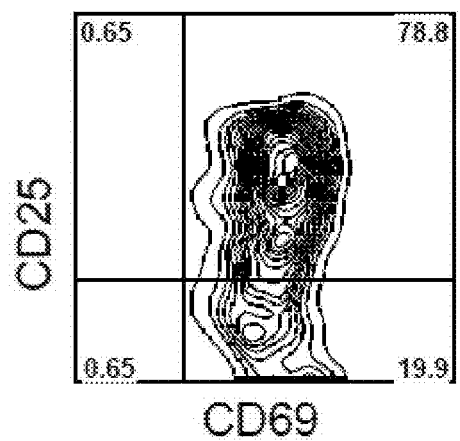
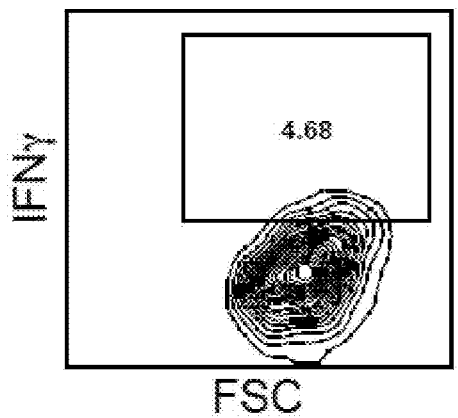
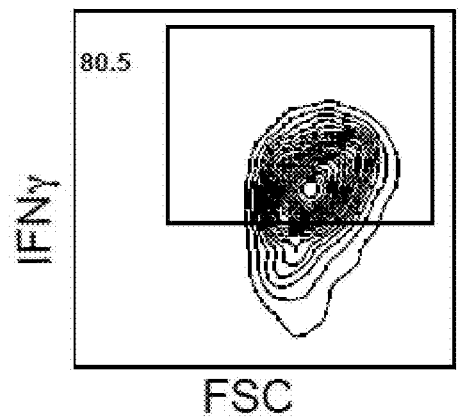
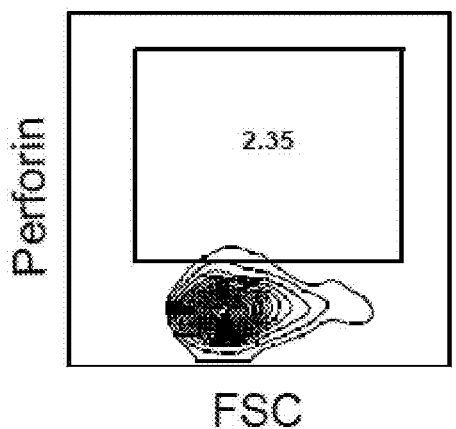
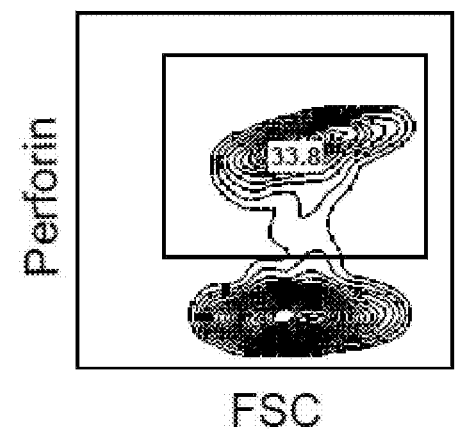

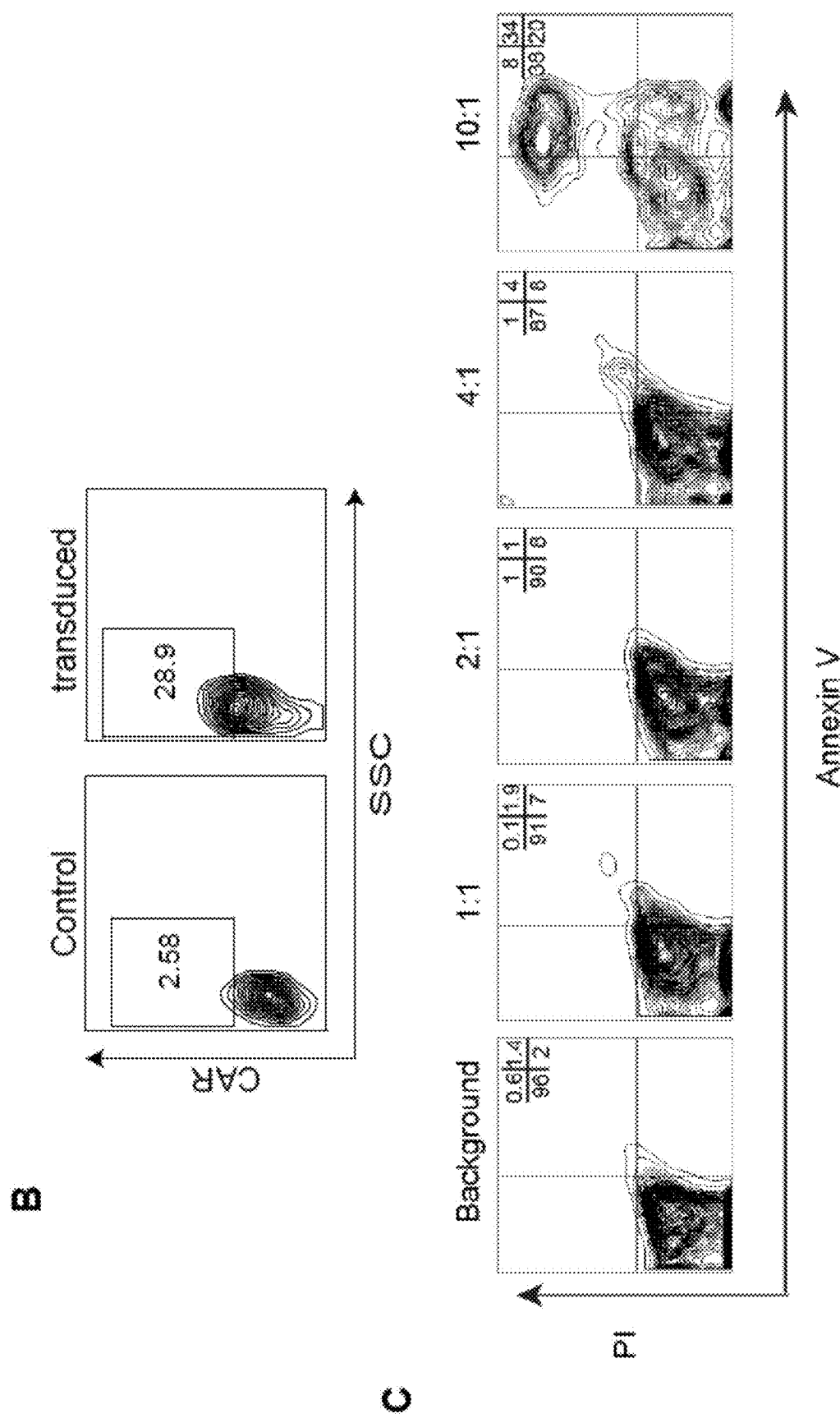
FIGS. 18A-18C, CONTINUED

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: synthetic

<400> SEQUENCE: 1
catccacaag acagcgggg                                                    19

<210> SEQ ID NO 2
<211> LENGTH: 19
<212> TYPE: DNA
<213> ORGANISM: Artificial Sequence
<220> FEATURE:
<223> OTHER INFORMATION: synthetic

<400> SEQUENCE: 2
ctcgtcggca tctggcttg                                                    19

<210> SEQ ID NO 3
<211> LENGTH: 22
<212> TYPE: DNA
<213> ORGANISM: Artificial Sequence
<220> FEATURE:
<223> OTHER INFORMATION: synthetic

<400> SEQUENCE: 3
ccagcctcaa aatcgtggcc cg                                                22

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
tttgatggcc cgaagccact cg                                                22

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
agaatccaga cctgcacaac                                                   20

<210> SEQ ID NO 6
<211> LENGTH: 19
```

```
<212> TYPE: DNA
<213> ORGANISM: Artificial Sequence
<220> FEATURE:
<223> OTHER INFORMATION: synthetic

<400> SEQUENCE: 6
gccggtactt gtagttggg                                          19

<210> SEQ ID NO 7
<211> LENGTH: 22
<212> TYPE: DNA
<213> ORGANISM: Artificial Sequence
<220> FEATURE:
<223> OTHER INFORMATION: synthetic

<400> SEQUENCE: 7
caatgtggat gccgcagttg tg                                      22

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
cagcaccttg gcggtctcgt a                                       21

<210> SEQ ID NO 9
<211> LENGTH: 18
<212> TYPE: DNA
<213> ORGANISM: Artificial Sequence
<220> FEATURE:
<223> OTHER INFORMATION: synthetic

<400> SEQUENCE: 9
ggcacctttg ccacactg                                           18

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
cactggtggg gtgaattctt                                         20

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gcctgtggag caagatgaat                                         20

<210> SEQ ID NO 12
<211> LENGTH: 16
<212> TYPE: DNA
<213> ORGANISM: Artificial Sequence
<220> FEATURE:
<223> OTHER INFORMATION: synthetic

<400> SEQUENCE: 12
```

```
gcgggcttga ggttgt                                                        16
```

```
<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
cttcaagctc ctgggaaatg t                                                  21

<210> SEQ ID NO 14
<211> LENGTH: 25
<212> TYPE: DNA
<213> ORGANISM: Artificial Sequence
<220> FEATURE:
<223> OTHER INFORMATION: synthetic

<400> SEQUENCE: 14
gcagaataaa gcctatcctt gaaag                                              25

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
aaccccagca cttaagcaaa                                                    20

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
ggaggtcatg atccccttct                                                    20

<210> SEQ ID NO 17
<211> LENGTH: 23
<212> TYPE: DNA
<213> ORGANISM: Artificial Sequence
<220> FEATURE:
<223> OTHER INFORMATION: synthetic

<400> SEQUENCE: 17
cctggaggag aagaggaaag aga                                                23

<210> SEQ ID NO 18
<211> LENGTH: 25
<212> TYPE: DNA
<213> ORGANISM: Artificial Sequence
<220> FEATURE:
<223> OTHER INFORMATION: synthetic

<400> SEQUENCE: 18
ttgaggacct ctgtgtattt gtcaa                                              25
```

INDUCTION OF ARTERIAL-TYPE OF HEMOGENIC ENDOTHELIUM (AHE) AND ENHANCEMENT OF T CELL PRODUCTION FROM PSCS THROUGH OVEREXPRESSION OF ETS FACTORS OR MODULATING MAPK/ERK SIGNALLING PATHWAYS

CROSS-REFERENCE TO RELATED APPLICATIONS

This Application claims priority to U.S. Provisional Application Nos. 62/424,144 and 62/572,066 filed on Nov. 18, 2016 and Oct. 13, 2017, respectively, the contents of which are incorporated by reference in their entireties.

STATEMENT REGARDING FEDERALLY SPONSORED RESEARCH

This invention was made with government support under HL116221, HL099773 and OD011106 awarded by the National Institutes of Health. The government has certain rights in the invention.

BACKGROUND OF THE INVENTION

De novo production of hematopoietic stem cells (HSCs) from in vitro expandable human cells, such as pluripotent stem cells (hPSCs), represents a promising approach for stem cell-based therapies and modeling of hematologic diseases. However, generation of HSCs and lymphoid cells from hPSCs remains a significant challenge[63-65]. Since HSCs are specified from hemogenic endothelium (HE) with definitive hematopoietic program, understanding molecular mechanisms regulating the establishment of HE with broad lymphoid and myeloid potentials is essential to advance the HSC manufacturing technology.

During development, blood cells and HSCs arise from hemogenic endothelium (HE). In contrast to the first wave of primitive hematopoiesis lacking of lymphoid and granulocytic potential, definitive hematopoiesis produces the entire spectrum of adult-type erythro-myeloid progenitors (EMP), lymphoid cells, and cells capable of limited engraftment (second wave), and HSCs with capacity of long-term repopulation of adult recipient (third wave)[6-8]. While some definitive hematopoietic cells such as EMPs can be produced from HE in venous vessels and capillaries[9-11], production of lymphoid cells and HSCs is mostly restricted to arterial vasculature[12-16]. The lack of venous contribution to HSCs when considered along with the shared requirements for Notch, VEGF, and Hedgehog signaling in both arterial fate acquisition and HSC formation[17-21], suggests that arterial specification is an essential prerequisite for establishing of definitive hematopoiesis with lymphoid potential. Although previous studies demonstrated arterial commitment within nonHE fraction of hPSC-derived endothelium[22], little is known about the effect of arterial programming on HE.

SUMMARY OF THE INVENTION

The present disclosure provides methods for promoting arterial hemogenic endothelium cell differentiation for human pluripotent stem cell populations in vitro. In one aspect, the method provides a method of promoting AHE differentiation by overexpression of ETS family transcription factor (e.g. ETS1) during hPSCs differentiation at the mesoderm cell population stage, which enhances arterial HE (AHE) formation. In one aspect, the overexpression of ETS family transcription factor, ETS1, was associated with promotion of HE formation with $DLL4^+$ $CXCR4^{+/-}$ arterial phenotype and TB lymphoid and definitive erythroid potentials.

In another aspect, arterialization of HE and enhancement of definitive hematopoiesis can be achieved through modulating of MAPK/ERK pathways, specifically by contacting the cells with a PI3K inhibitor. Methods of activating ERK pathway by inhibiting PI3K results in the enhanced production of $DLL4^+$ $CXCR4^{+/-}$ arterial type HE. In yet another aspect, arterialization of HE and enhancement of definitive hematopoiesis can be achieved through activation of NOTCH signaling at the mesodermal stage, specifically by contacting the $KDR^{hi}PDGFRA^{lo/-}$ mesodermal cells with a NOTCH ligand. In some aspects, the NOTCH ligand is selected from the group consisting of DLL1 and DLL4.

In another aspect, the disclosure provides a method of enhancing arterial specification in mesoderm cell population, the method comprising: (a) introducing an ETS transcription factor transgene into the mesoderm cell population; and (b) culturing the mesoderm cells under conditions sufficient to express the ETS transcription factor transgene within the mesoderm population and differentiating the mesoderm cells to arterial hemogenic endothelium (AHE) cells.

In another aspect, the disclosure provides a method of enhancing arterial specification in differentiating hPSC, comprising the steps of (a) introducing an ETS transcription factor transgene into a hPSC population, (b) culturing the hPSC cells under conditions to differentiate the hPSC cells into mesoderm cells at two days of differentiation, and (b) inducing expression of the transgene at day two of differentiation, such that arterial hemogenic endothelium cells (AHE) are obtained by day four of differentiation.

In yet another aspect, the disclosure provides a method of creating a cell population, comprising the steps of (a) obtaining a cell population of AHE cells, (b) further differentiating the AHE cells into an at least 90% pure population of cells, wherein the cell type of the cell population is selected from the group consisting of T-cells, B-cells, definitive (adult-type) red blood cells, myeloid progenitors and mature myelomonocytic cells.

In yet another aspect, the method provides a method of enhancing arterial specification in differentiating hPSC, comprising the steps of (a) culturing human mesoderm cells in defined cell culture medium comprising an effective amount of a factor capable of activating ERK signaling to differentiate the mesoderm cells into arterial hemogenic endothelium cells (AHE); and (b) obtaining the arterial hemogenic endothelium cells. In some aspects, the factor capable of activating ERK signaling is a PI3K inhibitor.

In another aspect, the disclosure provides a method of creating a cell population, comprising the steps of (a) obtaining a cell population of AHE $DLL4^+$ cells, (b) further differentiating the AHE $DLL4^+$ cells into an at least 90% pure population of cells, wherein the cell type of the cell population is selected from the group consisting of T-cells, B-cells, definitive (adult-type) red blood cells, myeloid progenitors and mature myelomonocytic cells.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 9A:
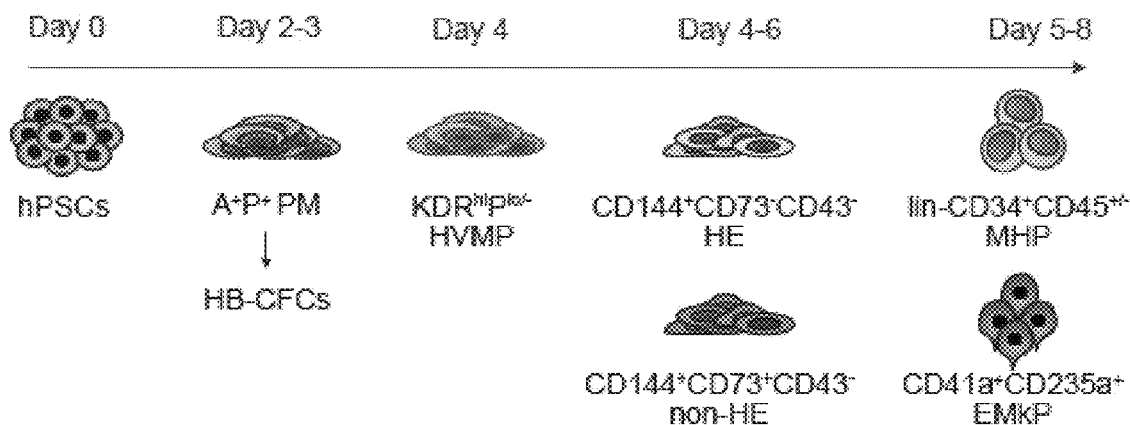
Figure 9B:
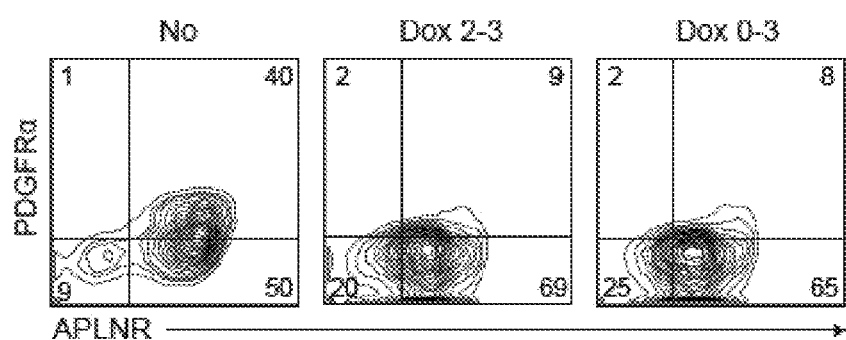
Figure 9C:
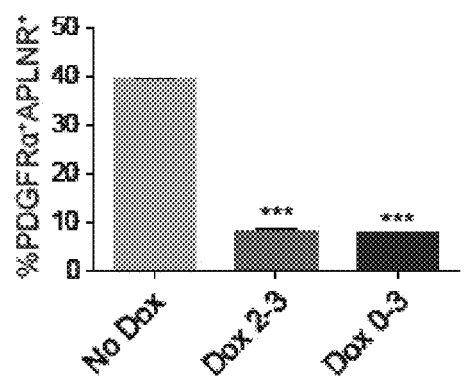

FIGS. 9A-9C Effect of ETS1 overexpression on development of primitive posterior mesoderm. (Aa) Schematic diagram depicts the major stages of hematopoietic development from hESCs. A+P+ PM is APLNR+PDGFRα+ primitive posterior mesoderm; HB-CFC is hemangioblast CFCs; $KDR^{hi}P^{lo/-}$ HVMPs is $KDR^{high}PDGFRα^{low/-}$ hematovascular mesodermal progenitors; HE, hemogenic endothelium; MHPs, multipotent hematopoietic progenitors; EMkPs, erythromegakaryocytic progenitors. (B) Representative contour plots show the DOX effect on A+P+ PM. (C) Percentage of A+P+ PM cells in DOX-treated and untreated cultures. Bars are mean±s.d. of three independent experiments; ***p<0.001.

Figure 10:
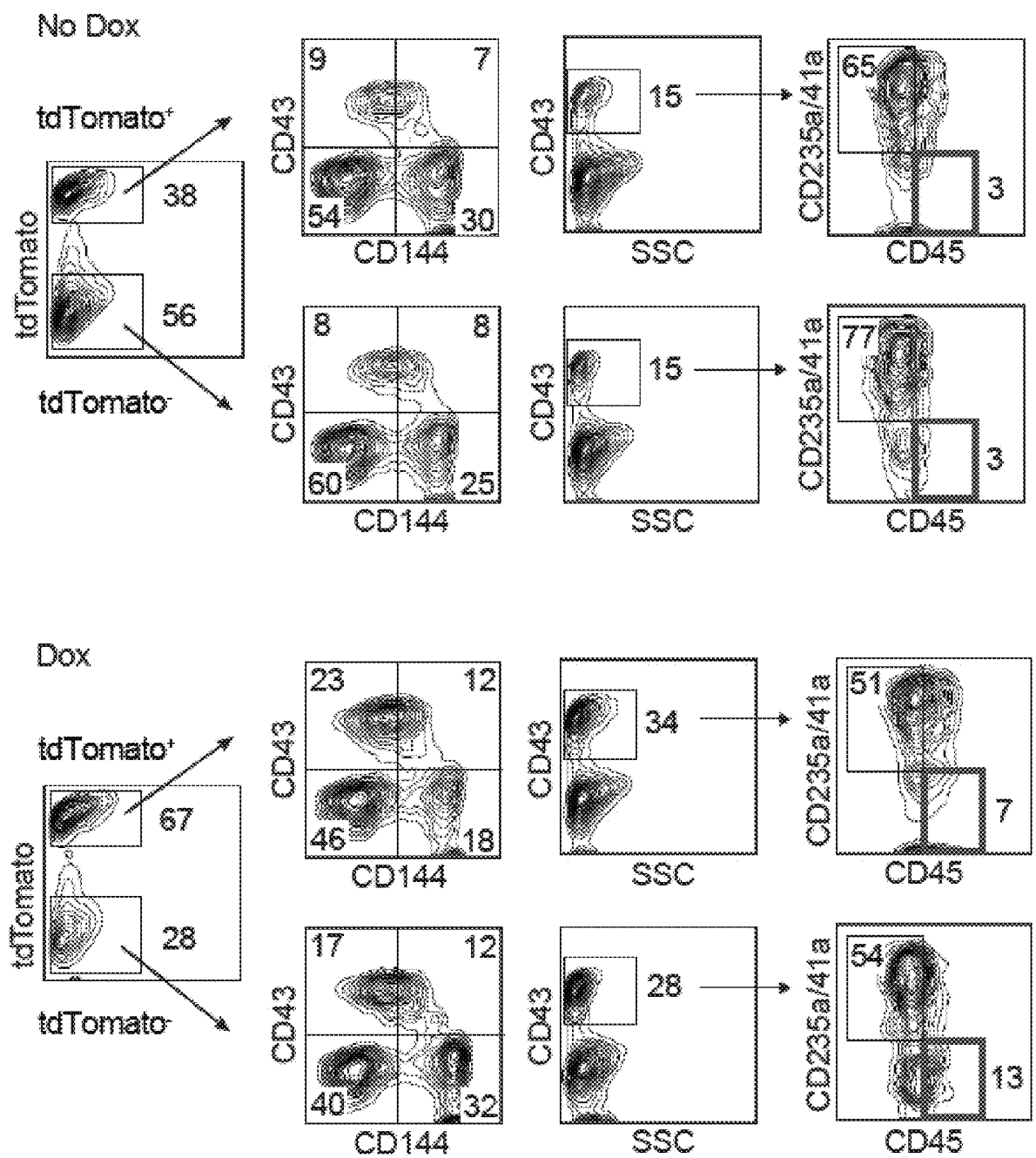
Figures 15A, 15B, 15C, 15D, 15E, 15F:
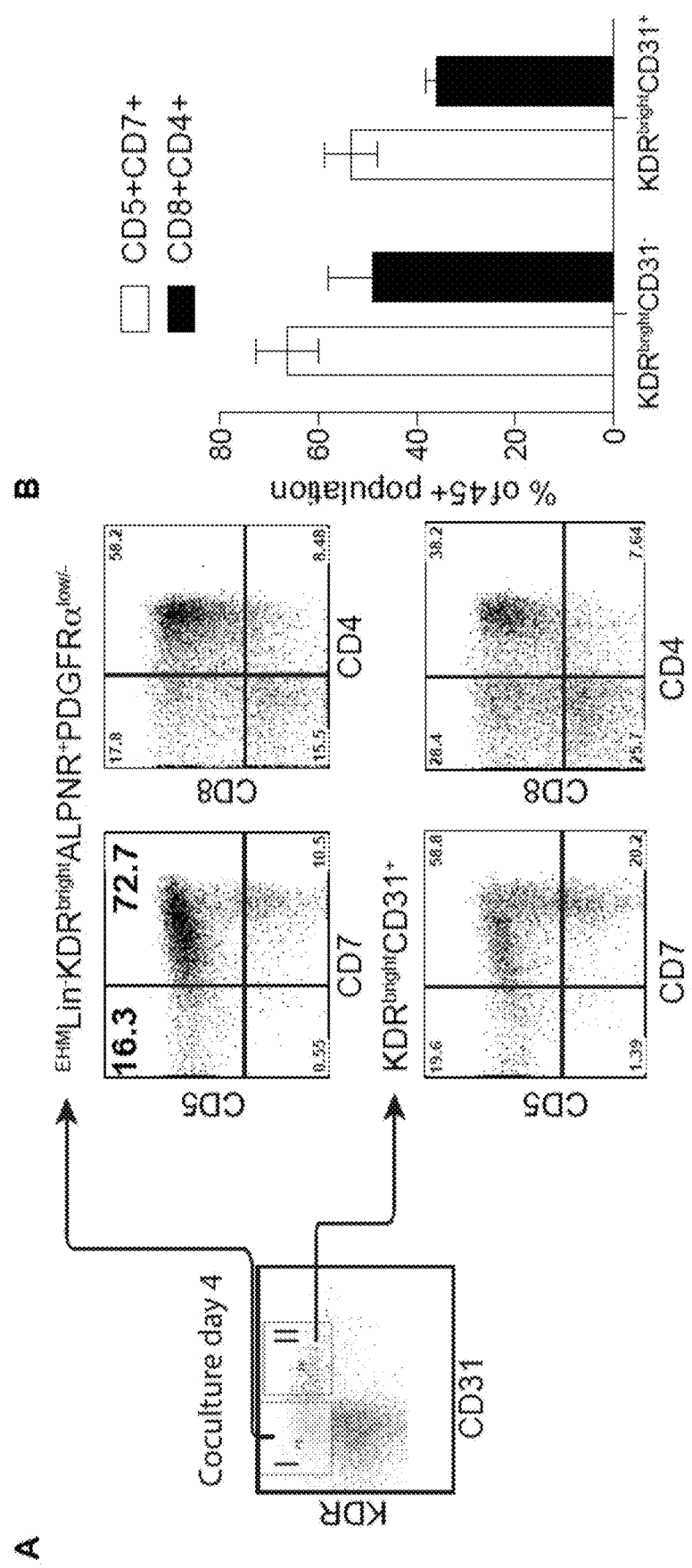

FIG. 10 shows evaluation of ETS1 effect using chimeric (wild type tdTomato+ and iETS1 tdTomato−) H1 hESCs. Representative contour plots show flow cytometric analysis of hematopoietic development on day 8 of differentiation following gating tdTomato+ or tdTomato− (iETS1) cells in DOX-treated and untreated cultures.

FIGS. 11A-11E show hematopoietic potential of CXCR4+ and CXCR4− DLL4+ arterial HE. (A) Schematic diagram of experiments. (B) and (C) flow cytometric analysis of hematopoiesis from CXCR4+ and CXCR4− DLL4+ HE. (D) CFC potential of CD43+ cells generated from CXCR4+ and CXCR4− DLL4+ HE. (E) Limiting dilution assay to determine the frequency of T cell progenitors from CXCR4+ and CXCR4− DLL4+ HE. Bars in (C) and (D) are mean±s.d. of three independent experiments; *p<0.05 and **p<0.01.

FIG. 12 lists the antibodies used for FACS.

FIG. 13 lists the primers used for RT-qPCR.

FIG. 14 is a schematic representation of generation of T Lymphoid cells from hematopoietic progenitor subsets using hESC/OP9 coculture system. Scheme shows the emerging progenitor subsets according to different co culture days. $KDR^+$ mesodermal hematovascular progenitors at coculture day 4, $CD144^+$ hemogenic endothelial progenitors at coculture day 5, and $CD43^+$ hematopoietic progenitors at coculture day 8.5 were isolated and used for T cell differentiation. T cell differentiation was accomplished on Op9-DLL4 using the respective subsets.

FIGS. 15A-15F demonstrate T cell differentiation from hESC-derived hematopoietic progenitor subsets. (A) $KDR^+$ mesodermal hematovascular progenitors were generated from hESC/OP9 coculture at day 4, $KDR^{hi}CD31^{-/+}$ subsets were sorted for lymphoid differentiation. (B) Percentage of T cell phenotypes from day 4 cell subsets, as detected by flow cytometry. (C) $CD144^+$ hemogenic endothelial progenitors were generated from hESC/OP9 coculture at day 5, different endothelial subsets were sorted for lymphoid differentiation. (D) Percentage of T cell phenotypes from day 5 cell subsets, as detected by flow cytometry. (E) $CD43^+$ hematopoietic progenitors were generated from hESC/OP9 coculture at day 8.5, subsets were sorted for lymphoid differentiation. (F) Percentage of T cell phenotypes from day 8.5 cell subsets, as detected by flow cytometry. All gates represent target cell population sorted by MACS and FACS.

Figures 16A, 16B, 16C:
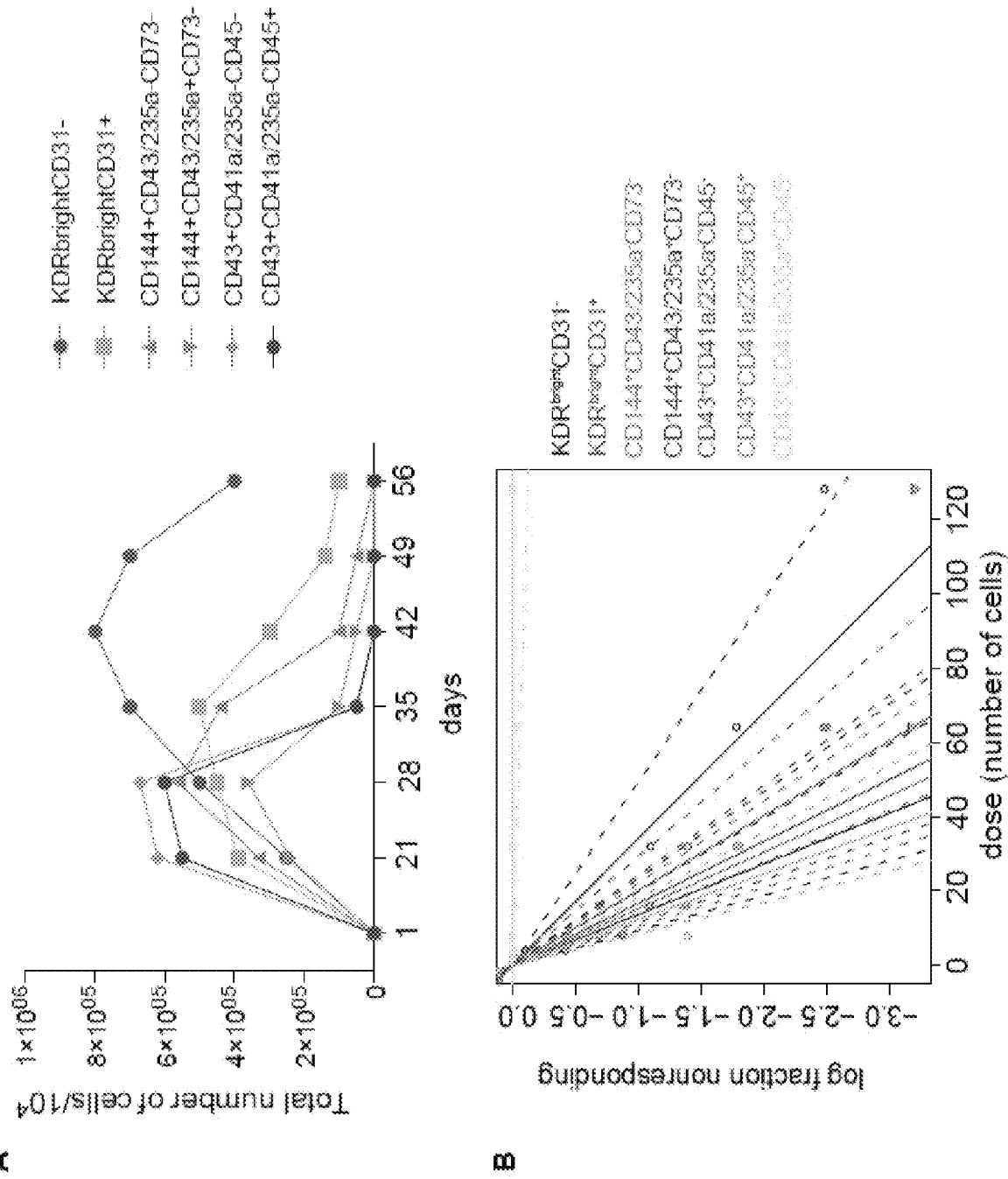

FIGS. 16A-16C show the characterization of T cells from different progenitor subsets. (A) Proliferative potential of T cells generated from various subsets. Expansion and proliferation potential of $KDR^{hi}CD31^-$ subsets is higher in comparison to other subsets. (B) Limiting dilution assay to determine the frequency of T cell progenitors from different subsets. (C) Comparison of hematopoietic colony-forming potential of subsets differentiated on OP9 and OP9-DLL4.

Figure 17:
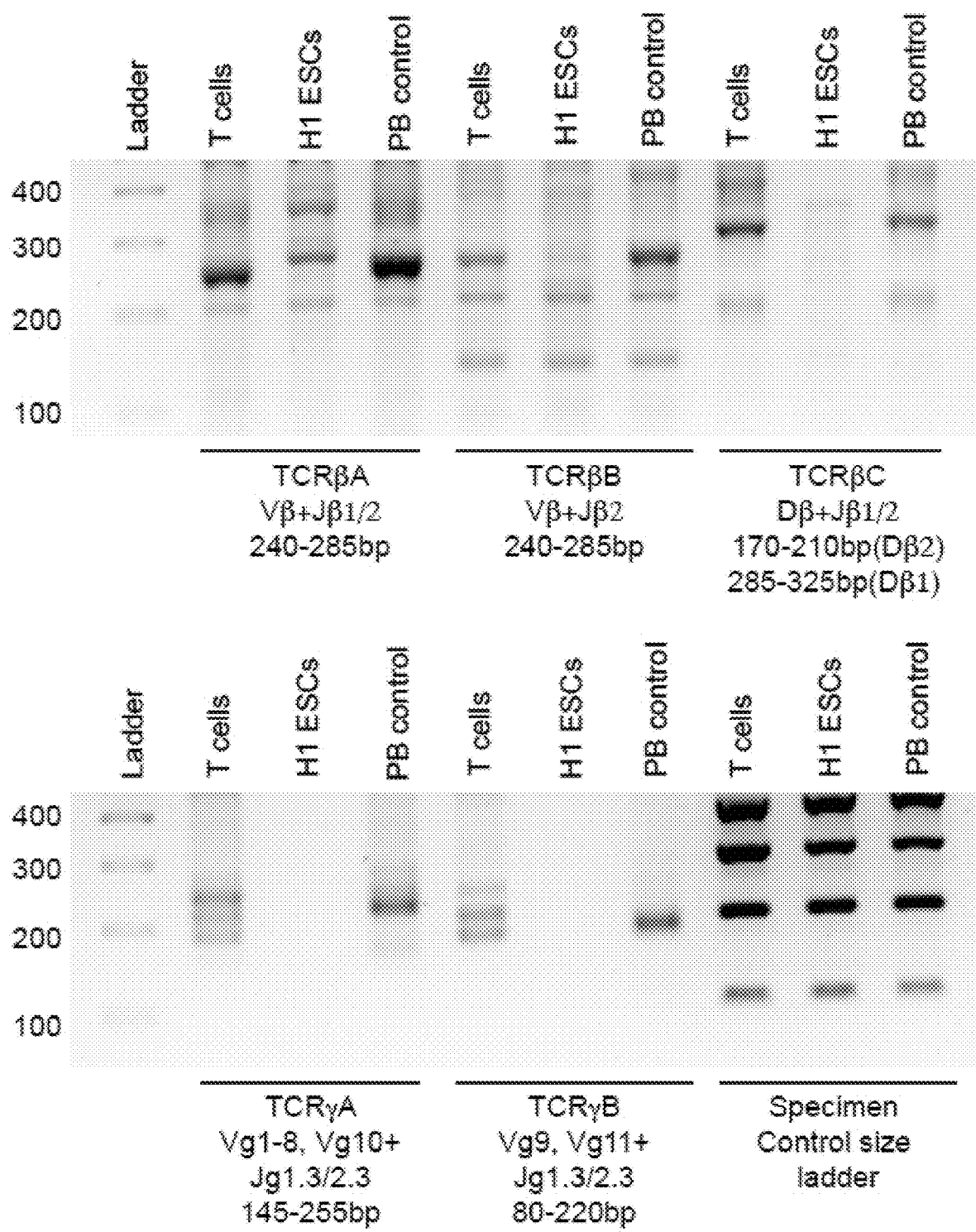

FIG. 17 depicts the analysis of TCR gene rearrangement in HVMP derived T cells. PCR analysis of TCR gene rearrangement in TCRβ and TCRγ locus of HVMP derived T cells and specimen control. M, 50 bp DNA ladder. T cells, genomic DNA from H1-derived T cells. H1, genomic DNA from hESC (negative control). PB, genomic DNA from peripheral blood (positive control) and undifferentiated H1 ESCs.

FIGS. 18A-18C show the results of the T cell Functional assay. (A) HVMP derived T cells were stimulated with PMA and ionomycin for 24 hours before analysis of activation markers CD25 and CD69 and intracellular protein IFN-γ and perforin. (B) Flow cytometry analysis of T cells transduced with CD19 CAR. (C) Cytotoxicity assay of HVMP derived CAR-T cells. CAR-T cells (effector) and Raji (target cells) were combined in ratio 1:1, 2:1, 4:1 and 10:1. Target cells (Raji) were labeled with PKH67 (green fluorescent cell linker) to distinguish from cell mixture.

DETAILED DESCRIPTION OF THE INVENTION

In General

The present disclosure demonstrates methods that allow for the promoting of arterial patterning in hPSC cultures that can aid in in vitro approaches to instruct definitive hematopoiesis with lymphoid and HSC potentials from hPSCs. Arterial program from hPSCs can be enhanced by overexpression of ETS family transcription factor, ETS1 which was associated with promotion of HE formation with $DLL4^+$ $CXCR4^{+/-}$ arterial phenotype and TB lymphoid and definitive erythroid potentials, as described in the Examples. Further, arterialization of HE and enhancement of definitive hematopoiesis can be achieved through modulating of MAPK/ERK pathways, further demonstrated in the examples. Methods of activating ERK pathway by inhibiting PI3K results in the enhanced production of $DLL4^+$ $CXCR4^{+/-}$ arterial type HE. Together, the Examples demonstrate different approaches in providing arterialization of HE and enhanced definitive hematopoiesis.

In the Examples, how arterial programming affects specification of definitive HE from hPSCs was investigated. During vascular development, arterial fate is specified following induction of DLL4 expression[23] initiated by signaling through arterial-specific enhancer located within the third intron of DLL4 that is controlled by ETS factors[24-25].

The inventors found that arterial program from hPSCs could be enhanced by overexpression of ETS family transcription factor, ETS1. The boost in arterial programming by ETS1 was associated with promotion of definitive HE formation with lymphoid and definitive erythroid potential. The observed increase in arterial programming by ETS1 was associated with promotion of HE formation with $DLL4^+$ $CXCR4^{+/-}$ arterial phenotype and T/B lymphoid and definitive erythroid potentials. The ETS1 effect was associated with upregulation of SOXF factors and DLL4 in endothelial cells. Inhibition of NOTCH signaling with DAPT or DLL4 neutralizing antibodies abrogated the effect of ETS1 overexpression in hematopoiesis, thereby indicating that enhancement of arterial patterning is mediated through upregulation of NOTCH signaling. Together these findings suggest that promotion of arterial patterning in hPSC cultures could aid in vitro approaches to instruct definitive hematopoiesis and HSC fate from hPSCs.

In one embodiment, the disclosure provides a population of hPSCs or mesoderm cells (e.g. KDR+ mesoderm cells) comprising an exogenous vector comprising the ETS transcription factor. This population of cells is capable of differentiation into arterial hemogenic endothelial cells upon expression of the exogenous vector. In some embodiments, the exogenous vector includes an inducible promoter that allows for inducing of the ETS transcription factor within the cells. Suitable exogenous vectors, including viral vectors, are discussed more below.

We expect that the result with ETS1 can be replicated with other ETS transcriptional factors. In one embodiment of the invention, the ETS factor is ETS1. In another embodiment of the invention, the ETS factor is selected from the group consisting of ETV2, ERG and ETS2. (See Y. Sato, Cell Structure and Function 26: 19-24 (2001), incorporated by reference in its entirety). We note that the ETS transcription factor FLI1 was not able to induce AHE from hPSCs (see Example 1).

In another embodiment, the present disclosure provides a method of enhancing arterial specification of hemogenic endothelium in mesoderm cells, the method comprising culturing the mesoderm cells in defined medium comprising an effective amount of a factor capable of activating NOTCH signaling to differentiate the mesoderm cells into arterial hemogenic endothelium (AHE) cells. As demonstrated in the Examples, the activation of NOTCH signaling allows for the arterial specification of hemogenic endothelium in mesoderm cells. Specifically, arterialization of HE and enhancement of definitive hematopoiesis can be achieved through activation of NOTCH signaling at the mesodermal stage, specifically by contacting the KDR$^{hi}$PDGFRA$^{lo/-}$ mesodermal cells with a NOTCH ligand. In some embodiments, the NOTCH ligand is selected from the group consisting of DLL1 and DLL4.

One goal of the present invention is to produce a population of arterial type hemogenic endothelial cells (AHEs). Arterial type cells (AHE) of the present invention are CD144+ CD73–DLL4+ HE that express high level of EFNB2 and NOTCH1 arterial markers. These cells have broad lympho-myeloid and definitive erythroid potentials.

As described in the Examples, arterial type cells are referred to as having a CD144+CD43–CD73–DLL4+ phenotype. Applicants note that the vast majority of CD43+ cells are DLL4– by default. In other words, selection of arterial type CD144+CD73–DLL4+ phenotype does not typically require CD43 exclusion.

In one embodiment, the present invention is a population of arterial hemogenic endothelium cells (AHE) that are CD144+CD73–DLL4+ HE that express high level of EFNB2 and NOTCH1 arterial markers. These cells have broad lympho-myeloid and definitive erythroid potentials. As described above, definitive hematopoiesis produces the entire spectrum of adult-type erythro-myeloid progenitors (EMP), lymphoid cells, and cells capable of limited engraftment (second wave), and HSCs with capacity of long-term repopulation of an adult recipient.

In some embodiments, the population of arterial hemogenic endothelium cells is produced by expression of an exogenous ETS factor (e.g. ETS1) in differentiating hPSCs (e.g. by use of an exogenous vector or exogenous viral vector).

In another embodiment, the present invention is a method of making AHE cells and a method of differentiating AHE cells to obtain cells of interest.

In another embodiment, methods of enhancing arterial specification in differentiating hPSCs by activating ERK signaling are provided. Specifically, the method comprises culturing of human mesodermal progenitors derived from hPSCs in chemically defined culture medium containing an effective amount of an activator of ERK signaling to obtain arterial hemogenic endothelium (AHE) cells. In one embodiment, the activator for ERK signaling is an inhibitor of phosphoinositide 3-kinase (PI3K) downstream of VEGF receptor signaling.

Methods of the Present Invention

In one embodiment of the present invention, we disclose a method of enhancing arterial specification in differentiating hPSC. In general, our method involves increase of ETS factor gene expression in hPSCs or mesoderm cells (KDR+ cells) by introducing an ETS transgene, preferably an inducible gene, into a hESC or mesoderm cell population. The ETS factor is selected from the group consisting of ETS1, ETV2, ERG and ETS2. In a preferred embodiment, the ETS factor is ETS1. The ETS factor gene may be obtained by amplifying the gene cDNA from human PSCs differentiated into endothelial and blood cells or cDNA clones can be obtained commercially (e.g. Sino Biological, Origene, etc.). In preferred embodiments, the ETS transgene is provided within a vector or plasmid.

In one embodiment of the present invention, we disclose a method of enhancing arterial specification in differentiating hPSC. In general, our method involves increase of ETS gene expression in hPSCs by introducing an ETS transgene (e.g. ETS1 transgene), preferably an inducible gene, into a hESC population. A typical ETS gene may be obtained by amplifying ETS cDNA from human PSCs differentiated into endothelial and blood cells or cDNA clones can be obtained commercially (e.g. Sino Biological, Origene, etc.). In a preferred embodiment, the ETS transgene is an ETS1 transgene. In another embodiment, the ETS transgene is a selected from the group consisting ETS1, ETV2, ERG and ETS2 transgenes.

The transgene can be inserted into the cell via any suitable method, for example by transfection or transduction.

In one embodiment, the ETS transgene comprises nucleic acid sequence able to express the human ETS1 protein (see. GenBank accession no. NP 001137292). In some embodiments, the ETS1 transgene further comprises a vector capable of expressing the ETS1 transgene within the cell. In some embodiments, the vector comprises an inducible promoter before the ETS1 transgene.

In another embodiment, the ETS transgene comprises nucleic acid sequence able to express the human ETS1 protein (see. GenBank accession no. NP 001137292), the ETV2 protein (GenBank accession no. NP 055024), ETS2 protein (GenBank accession no. NP 001243224) or the ERG protein (GenBank accession no. NP 891548). The ETS transgene may comprise a vector capable of capable of expressing the ETS transgene within the cell. In some embodiments, the vector comprises an inducible promoter before the ETS transgene.

In some embodiments, the PSCs or mesoderm cells are transduced with an exogenous vector encoding for the ETS factor, for example a recombinant vector (recombinant expression vector) such as a plasmid or viral vector. The exogenous vector allows for the expression of the ETS factor within the cell, in some examples, the exogenous vector is an inducible vector allowing for the controlled expression of the ETS factor within the cells during different stages of differentiation. In another embodiment, the PCSs or mesoderm cells are transduced with an exogenous modified mRNA of the ETS factor. In yet another embodiment, the PSCs or mesoderm cells are transduced with the ETS factor protein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." The vector include exogenous genetic material that allow for the expression of the transgene.

In some embodiments, the expression vector is a viral vector. Suitable viral vectors are known in the art and include, but are not limited to, for example, an adenovirus vector; an adeno-associated virus vector; a pox virus vector, such as a fowlpox virus vector; an alpha virus vector; a baculoviral vector; a herpes virus vector; a retrovirus vector, such as a lentivirus vector; a Modified Vaccinia virus Ankara vector; a Ross River virus vector; a Sindbis virus vector; a Semliki Forest virus vector; and a Venezuelan Equine Encephalitis virus vector. In a preferred embodiment, the viral vector is a lentiviral vector, an adenovirus vector or an adeno-associated virus vector.

In a preferred embodiment, expression of the ETS1 gene is at the mesoderm stage of development (day 2 of differentiation). (See Uenishi et al. 2014, incorporated by reference in its entirety, for typical developmental protocol.)

In one embodiment, the ETS factor may be inserted (e.g. transduced) into a hPSC using a vector comprising an inducible promoter, and the ETS factor may then be induced to be expressed at the mesoderm stage of development, e.g. day 2 of differentiation. In another embodiment, mesoderm cells are transduced with a vector comprising the ETS factor able to be expressed in the mesoderm cell (e.g. that may or may not be inducible). In some embodiments, the vector may be transient.

In one example, a typical vector would include inserting the ETS1 gene cloned downstream of a conditional promoter such as TREtight promoter that requires Doxycycline for activation. The gene could be introduced along with M2rtTA transactivator using, for example, a lentivirus system, PiggyBac transposon system or a plasmid.

Alternatively one can increase ETS factor expression in the cells by transfecting hPSCs on day 2 of differentiation with ETS factor modified mRNA. For example, the cells can be transfected with ETS1 modified mRNA.

The methods of the present invention would be suitable for any type of hPSC, including both embryonic stem cells and inducible pluripotent stem cells. One may wish to confirm the arterial specification by observing increased formation of CD144+ endothelial cells and induced expression of DLL4 and CXCR4 on endothelial cells in a dose-dependent manner. Molecular profiling of endothelial cells isolated on day 4 of differentiation will show marked increased expression of genes associated with arterial specification including CXCR4, NOTCH ligand DLL4, NOTCH1, NOTCH4, HEY1, SOXF group genes (SOX7, SOX17, SOX18), as well CD93 gene associated with emerging HSCs in the aorta-gonada-mesonephros (AGM) region in the embryo.

One may also wish to further differentiate the ETS1 induced cells. In general, one would consult standard procedures for cell differentiation to obtain cell populations of hematopoietic cells, such as T cells, beta-hemoglobin-producing red blood cells and multipotential myeloid progenitors, including granulocyte, erythrocyte, megakaryocyte, macrophage (GEMM) and granulocyte-macrophage (GM) colony-forming cells (CFCs) and mature myelomonocytic cells. See:

Uenishi, Gene, et al. "Tenascin C promotes hematoendothelial development and T lymphoid commitment from human pluripotent stem cells in chemically defined conditions." Stem cell reports 3.6 (2014): 1073-1084.

Choi, Kyung-Dal, Maxim Vodyanik, and Igor I. Slukvin. "Hematopoietic differentiation and production of mature myeloid cells from human pluripotent stem cells." Nature protocols 6.3 (2011): 296-313.

Dias, Jessica, et al. "Generation of red blood cells from human induced pluripotent stem cells." Stem cells and development 20.9 (2011): 1639-1647.

Vodyanik, Maxim A., et al. "Human embryonic stem cell—derived CD34+ cells: efficient production in the coculture with OP9 stromal cells and analysis of lymphohematopoietic potential." Blood 105.2 (2005): 617-626.

Example 1 discloses that an AHE cell fraction cultured on DLL4–OP9 cells underwent endothelial-to-hematopoietic transition and produced blood cells. Our evaluation of lymphoid and CFC potential revealed that CD144+CD73−DLL4+ arterial type hemogenic endothelium population has a more potent T cell potential.

Figures 8A, 8B, 8C, 8D:
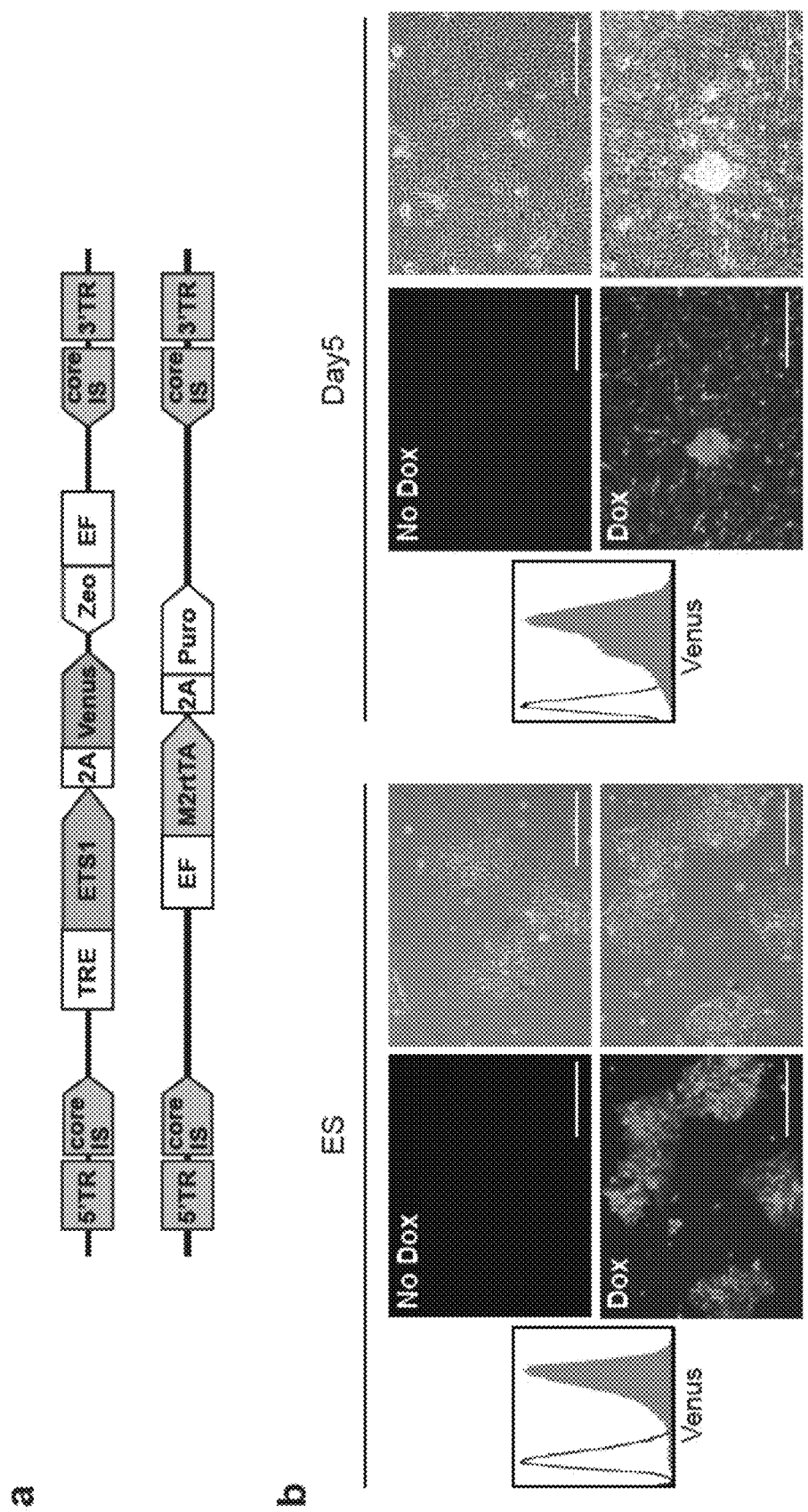
FIGS. 8A-8D show generation of conditional H1 hESC cell line (iETS1-hESC). (A) Schematic diagram of Piggy-Bac system used to generate iETS1. (B) Expression of Venus reported in undifferentiated and day 5 differentiated iETS1 cells. Dose-dependent effect of DOX on ETS1 expression in undifferentiated iETS1-hESCs as determined by RT-qPCR (C) and Western Blot (D).

Example 1 discloses a number of embodiments of the present invention. To evaluate effect of ETS1 on arterial programming and hematopoiesis from hPSCs, H1 human embryonic stem cells (hESC) were engineered carrying doxycycline (DOX)-inducible ETS1 transgene (FIG. 8) and differentiated them into endothelial and hematopoietic cells in chemically defined conditions[26].

Methods of differentiating hPSCs to mesoderm cells (e.g. KDR+ mesoderm cells) are known in the art. For example, the hPSCs may be cultured in chemically defined medium or co-cultured with OP9 cells as known in the art. For example, in one embodiment the hPSCs are cultured in chemically defined medium comprising BMP4, activin A, LiCl and FGF2 on coated plates (e.g. collagen IV coated or TenC coated) wherein the hPSCs are differentiated into mesoderm cells (e.g. cells expressing KDR+). A suitable method is described in Uenishi et al. 2014, incorporated by reference herein.

In some embodiments, the cells are attached to a culture plate via extracellular matrix proteins. For example, in one embodiment, the cells are attached via collagen, fibronectin, Matrigel™ or Tenascin C (TenC). In a preferred embodiment, the cells are cultured on plates coated with TenC or Collagen IV as described in Uenishi et al.

Figures 1A, 1B, 1C, 1D, 1E:
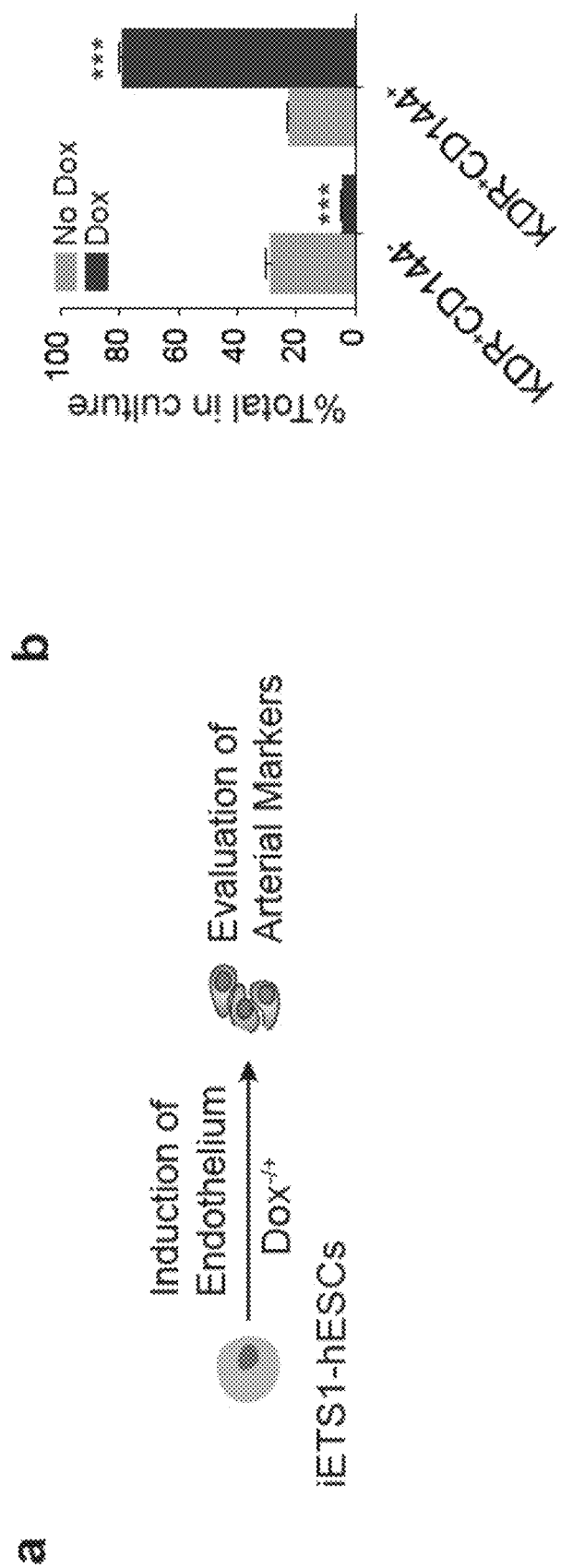
FIGS. 1A-1E demonstrate that ETS1 induction enhances arterial specification of hPSCs. (A) Experimental scheme. iETS1 hESC were differentiated in defined conditions with or without Dox for 4 days and evaluated for expression of arterial markers in CD144$^+$ endothelial cells. (B) The effect of DOX treatment on generation of CD144$^+$ endothelial cells. (C) Flow cytometric analysis of arterial markers expression by hESC-derived endothelial cells following DOX treatment (1, 1.5 or 2 µg/ml) for 2-4 days. Representative experiment of three independent experiments is shown. (D) Heat map of arterial and venous genes expression in day 4 KDR$^+$CD144$^+$ endothelial cells obtained with or without ETS1 induction as determined by RNAseq analysis. Gene expression is estimated in tpm values. (E) RT-qPCR analysis confirms upregulation of arterial genes following DOX treatment. Bar graphs in (B) and (E) are mean±s.d. of at least three independent experiments; *p<0.05; p<0.01;*p<0.001

To determine whether ETS1 overexpression promotes arterial specification, we treated cultures with DOX beginning at mesodermal stage of development (day 2 of differentiation) and analyzed the expression of the arterial markers DLL4 and CXCR4[23,27] on CD144+ endothelial cells emerging on day 4 of differentiation (FIG. 1A).

As shown in FIGS. 1B and 1C, DOX treatment increased formation of CD144+ endothelial cells and induced expression of DLL4 and CXCR4 on endothelial cells in dose-dependent manners. Molecular profiling of endothelial cells isolated on day 4 of differentiation, revealed that ETS1 upregulation led to marked increased expression of genes associated with arterial specification including CXCR4, EFNB2, NOTCH ligand DLL4, NOTCH1, NOTCH4, HEY1, SOXF group genes (SOX7, SOX17, SOX18), as well CD93 gene associated with emerging HSCs in AGM region[24, 27-34], but downregulated the expression of NR2F2 and APLNR venous markers (FIG. 1D). Based on these findings, we concluded that ETS1 upregulation enhances arterial specification from hPSCs.

Previous studies demonstrated that VEC$^+$CD43$^-$CD73$^-$ HE is lacking arterial marker CXCR4[37,22] and that hemogenic potential within VEC$^+$CD43$^-$CD73$^-$ could be further enriched by excluding cells expressing the earliest arterial marker DLL4[22]. However, we found that increased blood production following ETS1 overexpression was associated with a marked increase of DLL4$^+$ fraction within CD144$^+$CD73$^-$ HE population that acquires expression of CXCR4, thereby suggesting that enhancement of definitive hematopoietic program could be attributed to DLL4$^+$ HE population that acquires arterial characteristics. To find out whether arterial type HE has hematopoietic potential we sorted DLL4$^+$ and DLL4$^-$ cells and assessed their hematopoietic potential in defined conditions on matrix in presence of hematopoietic cytokines. DLL4$^+$ population in contrast to DLL4$^-$ failed to produce blood in these conditions. However, when we cultured DLL4$^+$ fraction on DLL4–OP9, we found that these cells undergo endothelial-to-hematopoietic transition and produced blood cells. Evaluation of lymphoid and CFC potential revealed that CD144$^-$ CD73$^-$ DLL4$^+$ arterial type hemogenic endothelium population has a more potent T cell potential than the DLL4– population.

As demonstrated by the Examples, the ETS1 effect is mediated through the upregulation of DLL4 expression and activation of NOTCH signaling. Further Example 2 demonstrates that activation of NOTCH signaling at the mesoderm stage cells can enhance arterial specification and increase the production of T cells. Specifically, the inventors has found that coculturing isolated KDR$^{hi}$PDGFR$^{lo/-}$ mesodermal cells on stromal cells (e.g. OP9 cells) with a NOTCH ligand results in an increased number of T cells with high expansion potential. Prior to this discovery, it has been difficult to make expandable T cells from PSCs.

Thus, in another embodiment, the disclosure provides methods of enhancing arterial specification of hemogenic endothelium by activating NOTCH signaling in mesoderm cells. In one embodiment, a method of enhancing arterial specification of hemogenic endothelium in mesoderm cells is provided, the method comprising culturing the mesoderm cells in defined medium comprising an effective amount of a factor capable of activating NOTCH signaling to differentiate the mesoderm cells into arterial hemogenic endothelium (AHE) cells. In another embodiment, a method of enhancing arterial specification of hemogenic endothelium is provided, the method comprising: (a) introducing into a mesoderm cell population a transgene able to upregulate NOTCH signaling within the mesoderm cell population; and (b) culturing the mesoderm cells under conditions sufficient to upregulate NOTCH signaling and differentiate the mesoderm cells to arterial hemogenic endothelium (AHE) cells.

In another embodiment, the method provides a method of differentiating expandable T cells from KDR$^{hi}$PDGFR$^{lo/-}$ mesodermal cells. The method comprises culturing the KDR$^{hi}$PDGFR$^{lo/-}$ mesodermal cells with NOTCH ligand. This method produces T cells with high expansion potential. The T cells are CD4+CD8+ T cells.

The term "T cells with high expansion potential" or "expandable T cell population" refers to a population of T cells that is able to divide and multiply in culture for at least 10 passages, suitably at least 20 passages, alternatively for at least 30 passages, alternatively for at least 40 passages. The T cells retain their identity throughout the culture passages. In a preferred embodiment, the expandable T cell population is able to be cultured for at least 40 passages.

Examples of suitable factors that activate NOTCH signaling include, but are not limited to, for example, NOTCH ligands, feeder or stromal cells expressing NOTCH ligands (e.g. OP9 cells expressing DLL1 or DLL4) and solid surfaces with immobilized NOTCH ligands (e.g. plates coated with NOTCH ligands). Suitable NOTCH ligands include, for example, DLL1-Fc (which has been described in other papers as Delta1ext-IgG), Jag1 ligand, and DLL4. Other examples of suitable factors that activate NOTCH signaling include an immobilized synthetic molecule that can bind to NOTCH and sufficiently activate the NOTCH receptor and the ectopic expression of the active, intracellular domain of NOTCH1 (Notch-ICD).

The mesoderm cells may be plated onto an NOTCH activation agent, such as immobilized Notch ligands, to activate NOTCH signaling (Hadland et al., 2015; Ohishi et al., 2002). Activation of NOTCH signaling by any means is suitable, for example, overexpression of the active form of NOTCH receptor or NOTCH ligands. See Bigas, A., D'Altri, T., and Espinosa, L. (2012). The Notch pathway in hematopoietic stem cells. Curr Top Microbiol Immunol 360, 1-18.

Bigas, A., and Espinosa, L. (2012). Hematopoietic stem cells: to be or Notch to be. Blood 119, 3226-3235.

Butko, E., Pouget, C., and Traver, D. (2016). Complex regulation of HSC emergence by the Notch signaling pathway. Dev Biol 409, 129-138.

Lu, Y F., Cahan, P., Ross, S., Sahalie, J., Sousa, P M., Hadland, B. K., Cai, W., Serrao, E., Engelman, A N., Bernstein, I D., Daley, G Q. (2016) Engineered Murine HSCs Reconstitute Multi-lineage Hematopoiesis and Adaptive Immunity. Cell Report 17, 3178-3192 the contents of which are incorporated by reference in their entirety.

In one example, the factor capable of activating NOTCH signaling is selected from the group consisting of DLL4, DLL1-Fc, DLL1-expressing feeder or stromal cells (e.g. DLL1-expressing OP9 cells), DLL4-expressing feeder or stromal cells (e.g. DLL4-expressing OP9 cells), plates coated with DLL4-Fc, and plates coated with DLL1-Fc.

In one embodiment, the disclosure provides a method of differentiating KDR$^{hi}$PDGFR$^{lo/-}$ mesenchymal stem cells into CD8+CD4+ T cell population by culturing the KDR$^{hi}$PDGFR$^{lo/-}$ mesenchymal stem cells in the presence of OP9-hDLL4 cells. OP9-hDLL4 cells were maintained in a-MEM media containing 20% FBS on 0.1% gelatin-in distilled water coated 10 cm cell culture dish. Cells were passaged every 4 days. For lymphoid differentiation, OP9-hDLL4 cells were cultured in the gelatin coated 6 well plates. When OP9-hDLL4 cells formed a confluent monolayered (4 days old cells), sorted hematopoietic progenitors were cocultured on OP9–DLL4 in a-MEM, 20% FBS, IL-7 (5 ng/ml), Flt3L (5 ng/ml) and SCF (10 ng/ml) at 37° C. and 5% CO2 for 3-4 weeks with weekly passage. Every 6-7 days co-cultures were transferred onto fresh OP9–DLL4 cells by vigorous pipetting and passaging through a 40 μm cell strainer.

In another embodiment, a method of enhancing arterial specification in differentiating hPSCs is achieved by activating ERK signaling. Specifically, the method comprises culturing of human mesodermal progenitors derived from hPSCs in chemically defined culture medium containing an effective amount of an activator of ERK signaling to obtain arterial hemogenic endothelium (AHE) cells.

In one embodiment, the activator for ERK signaling is an inhibitor of phosphoinositide 3-kinase (PI3K) downstream of VEGF receptor signaling. Suitable PI3K inhibitors are known in the art and include, but are not limited to, LY294002, GS4894, and wortmannin, among others. See Hong et al. "Artery/Vein Specification Is Governed by Opposing Phosphatidylinositol-3 Kinase and MAP Kinase/ERK Signaling, Current Biology, 16, 1366-1372 (2006), incorporated by reference in its entirety. In a preferred embodiment, the PI3K inhibitor is LY294002.

Suitable effective amounts of the PI3K inhibitors include, but are not limited to about 0.01 μM-about 20 μM preferably about 0.1 μM-10 μM. Suitable ranges for specific PI3K inhibitors include, but are not limited to, for example, for LY294002 about 0.1 μM-50 μM, preferably about 0.1 μM-10 μM, preferably about 0.5 μM-5 μM, including any amount or ranges in between, including, for example, about 0.1 μM-20 μM, 0.1 μM-10 μM, 0.1 μM-5 μM, 0.1-3 μM, 0.5 μM-20 μM, 0.5-10 μM, 0.5 μM-5 μM, 0.5-4 μM, 0.5-3 μM; for wortmannin about 0.01 μM to about 10 μM, preferably about 0.01 μM to about 5 μM, including, but not limited to, for example, 0.05 μM-10 μM, 0.05 μM-5 μM, 0.1 μM to 1.0 μM, 0.1 μM to 2 μM, 0.5 μM to about 10 μM, 0.5 to about 5 μM, and any amount or range in between, for GS4894, amount of about 0.1 μM-20 μM, preferably about 0.1 μM-10 μM, including, but not limited to, 0.1 μM-5 μM, 0.1-3 μM, 0.5 μM-20 μM, 0.5-10 μM, 0.5 μM-5 μM, 0.5-4 μM, 0.5-3 μM. In a preferred embodiment, the amount of the PI3K inhibitor is about 0.1 μM-5 μM, suitably about 0.1 μM-3 μM, and preferably is LY294002.

The Example demonstrates that the indirect ERK activation through inhibition of Phosphoinositide 3-kinase (PI3K) downstream of VEGF receptor signaling, enhances arterial specification of hPSCs, while inhibition of ERK branch blocks arterial specification.

Figures 6A, 6B, 6C, 6D, 6E, 6F, 6G, 6H:
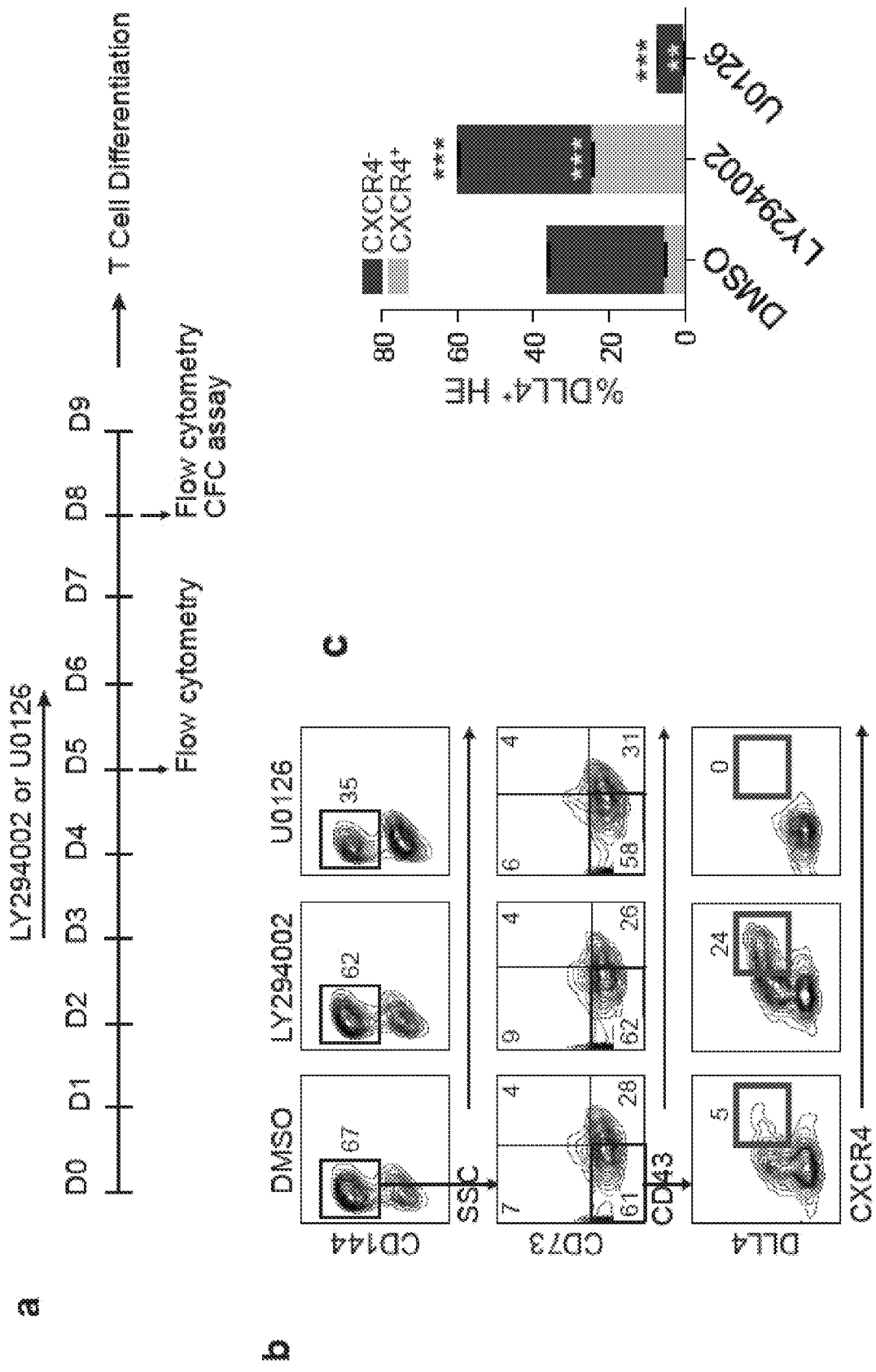
FIGS. 6A-6H show modulation of MAPK/ERK signaling enhances arterial specification and definitive hematopoiesis from hESCs. (A) Experimental scheme. Effect of LY294002 and U0126 on arterial HE specification (B) and (C), hematopoietic (D)-(E), CFC (F) and T cell development (G) and (H) from hESCs. Bars in (C), (E), (F) and (H) are mean±s.d. of at least three independent experiments; *p<0.05, p<0.01;*p<0.001.

In some embodiments, the differentiation cultures were treated with the ERK activation factor, e.g. the PI3K inhibitor (for example LY294002), on days 3 through day 6, demonstrating enhanced production of DLL4+ arterial type HE, including the DLL4+CXCR4+ fraction. Treatment using a MAPK inhibitor, U0126, almost completely abrogated formation of DLL4+ HE (FIGS. 6B and 6C). A direct correlation between definitive hematopoiesis efficacy and arterial specification was seen. When ERK pathways were activated following HE specification, production of multipotent CD235a/CD41a-CD45+ hematopoietic progenitors and CFC potential was dramatically increased, while ERK inhibition abrogated production of these types of cells (FIG. 6D-6F). In addition, T lymphoid potential was significantly increased in cultures treated with LY294002 and entirely abrogated in cultures treated with U0126. Overall, treatment with a PI3K inhibitor during differentiation of hPSCs enhanced arterial specification of HE which is essential to establish a definitive hematopoietic program with lympho-myeloid potentials from hPSCs.

The methods described herein induced formation of DLL4+CXCR4+/− arterial type HE that are highly enriched in definitive hematopoietic progenitors with T and B lymphoid potentials. In addition, arterial program activation enhanced production of CD34+CD43+ hematopoietic progenitors expressing HSC homing receptor CXCR4, which is typically not present in hematopoietic progenitors in traditional hESC differentiation cultures. DLL4 is expressed by HE underlying intra-aortic hematopoietic clusters in the AGM[47] and recent mouse studies have revealed significant enrichment in pre-HSCs in the DLL4+ fraction of AGM HE. The in vitro data of Example 1 correlates with in vivo observation and suggest that induction of HE arterialization is critical to mimic the proper specification of definitive hematopoiesis and HSC formation from hPSCs in vitro.

This disclosure also provides methods of improving T cell progenitor production. As described herein, PSCs that undergo arterial programming in lymphoid development results in significantly improved T cell progenitor production in defined conditions by applying small molecules to enhance formation of arterial type HE. Scalable T cell production is essential to advance translation of iPSC-based immunotherapies into the clinic.

In one embodiment, the specification provides a method of creating a cell population, comprising the steps of (a) obtaining a cell population of AHE DLL4+ cells, (b) further differentiating the AHE DLL4+ cells into an at least 90% pure population of T-cells. In some embodiments, step (b) comprises co-culturing the AHE DLL4+ cells with stromal cells expressing NOTCH ligand DLL4 or others (DLL1, DLL3, JAG1 or JAG2) (for example, OP9-DLL4+ cells) in T cell differentiating medium for an effective amount of time to differentiate the AHE cells into T-cells.

Example 1 further demonstrates methods of enhancing arterial specification in differentiating hPSC by activating ERK signaling. The method comprises (a) culturing human mesoderm cells in defined cell culture medium comprising a factor capable of activating ERK signaling in a sufficient amount and for a sufficient time to differentiate the mesoderm cells into arterial hemogenic endothelium cells (AHE); and (b) obtaining the arterial hemogenic endothelium cells.

Suitable methods of obtaining the arterial hemogenic endothelium cells may be isolating the AHE via expression of cell surface markers (e.g. CD144+ CD73−DLL4+ HE) as described herein.

Suitable methods of differentiating PSCs to mesoderm progenitor cells are known in the art. In one embodiment, the human mesoderm cells are obtained from a method comprising culturing human PSCs in a chemically defined culture medium for about 2 to about 4 days, whereby a cell population comprising human KDR+ mesoderm cells is obtained. Mesoderm may be obtained in any conditions and include, but are not limited to, OP9 system or Uenishi defined system as described in Uenishi et al. 2014, which is incorporated by reference in its entirety (medium comprising BMP4, Activin A, LiCl and FGF2 on coated plates under hypoxic conditions (5% $O_2$, 5% $CO_2$). Thus, the method of culturing AHE is described in FIG. 7, wherein PSCs are cultured to mesoderm progenitor cells for 1-4 days, at which time the mesoderm progenitors cells are further cultured in defined cell culture medium comprising a factor capable of activating ERK signaling to differentiate the mesoderm cells into AHE cells. The AHE cells obtained further express one or more arterial markers selected from the group consisting of EFNB2, NOTCH1, NOTCH 4 and SOX17.

The terms "defined culture medium," "defined cell culture medium," "defined medium," and the like, as used herein, indicate that the identity and quantity of each medium ingredient is known. As used herein, the terms "chemically-defined culture conditions," "fully defined, growth factor free culture conditions," and "fully-defined conditions" indicate that the identity and quantity of each medium ingredient is known and the identity and quantity of supportive surface is known. As used herein, the term "albumin-free" indicates that the culture medium used contains no added albumin in any form, including without limitation Bovine Serum Albumin (BSA) or any form of recombinant albumin. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that do not contain serum or serum replacement, or that contain essentially no serum or serum replacement. For example, an essentially serum-free medium can contain less than about 1%, 0.9%, 0.8%, 0.7%, 0.6%, 0.5%, 0.4%, 0.3%, 0.2%, or 0.1% serum. "Serum free" also refers to culture components free of serum obtained from animal (e.g., fetal bovine) blood or animal-derived materials, which is important to reduce or eliminate the potential for cross-species viral or prion transmission. For avoidance of doubt, serum-containing medium is not chemically defined.

Suitable defined medium includes, but is not limited to, E8 medium.

The AHE cells can be identified as CD144+CD43−CD73−DLL4+. AHE cells are CXCR4+/−.

In some embodiments, the AHE cells are sorted from the cell culture.

Suitably, the PSCs can be selected from the group consisting of embryonic stem cells (ESCs) or induced pluripotent stem cells (iPSCs).

Compositions of the Present Invention

In another embodiment, the present invention is a cell line created from the methods of the present invention. This hemogenic cell line will contain an ETS transgene, such as an ETS1 transgene, and be at least 90, 95% or 99% pure.

In further embodiments, one would wish to obtain the following cell lines:
(1) CD144+ CD43−CD73−DLL4+,
(2) T cells,
(3) B cells,
(4) Definitive (adult-type) red blood cells,
(5) myeloid progenitors or mature myelomonocytic cells
by use of the methods described herein. As discussed above, the methods described herein provide an enrichment in T cell progenitors, for example at least a 3 fold enrichment for T cell progenitors, alternatively at least a 10 fold, alternatively at least 25 fold, alternatively at least 50 fold, alternatively at least 75 fold, alternatively at least 100 fold enrichment of T cell progenitors. In some embodiments, the methods described herein using ETS1 have produced about 50 to 100 fold enhancement of T cell progenitors, e.g. 50 fold, 60 fold, 70 fold, 80 fold, 90 fold, 100 fold. In other embodiments, the methods provided herein can be used to obtain the following cell lines: a) CD235a/CD41a−CD45+ progenitors, granulocyte-macrophage colony-forming cells (GM-CFC), granulocyte-erythrocyte-macrophage-megakaryocyte (GEMM), and erythroid cells expressing β-hemoglobin and BCL11a. In some embodiments, the methods provide a population of AHE-DLL4+ cells that have B cell potential.

The T cells generated by the methods described herein go through a CD5+CD7+ progenitor stage that eventually transitions into CD8+CD4+ double positive cells (~90%), CD3+TCRa/b+ and CD3+TCRg/d+ cells. In one embodiment, the methods are able to produce T cells that are positive for CD8+ and CD4+ (double positive CD4+CD8+). In some embodiments, the methods are used to generate CD5+CD7+ progenitor T cell population that is expandable in culture to produce CD4+CD8+ cells that can further differentiate into CD4+ or CD8+ T cells. In another embodiment, the T cells generated are CD8+CD4+ T cell population that is at least 80% pure, preferably about 90% pure. In a preferred embodiment, the methods provide a population of T cells that are at least 90% positive for CD4+ and CD8+.

As demonstrated in Example 2, the ability to enrich in T cell progenitors allows for the ability to generate a population of T cell progenitors and ultimately T cells. The ability to produce large populations of T cells can be used in combination with the ability to transduce the T cells and express an engineered chimeric antigen receptor (CAR) within these cell populations. These engineered T cells can further be used for treatment of cancer as a form of cancer therapy. Example 2 demonstrates the transduction of T cells made by the methods described herein with exogenous CD19 CAR. These engineered CAR-expressing T cells were further shown to be able to kill tumor cells (Raji cells, cultured cell line of lymphoblastoid cells derived from a Burkitt lymphoma).

In one embodiment, the CAR expressing T cells can be used to kill tumor cells. The tumor cells are contacted with the CAR expressing T cells in an effective amount in order to kill the tumor cells.

In another embodiment, the CAR expressing T cells can be used to treat a subject having cancer. The CAR expressing T cells can be administered in an effective amount to treat the cancer. The CAR expressing T cells can be adoptively transferred to the patient. Suitable engineered CAR-expressing T cells for use in treating a subject having cancer are known in the art and include, CAR that are specific to a tumor-associated antigen. For example, in one embodiment, the CAR is a CD19 chimeric antigen receptor.

Design and methods of making CARs are known in the art and include, but are not limited to the first, second, third and fourth generation of CARs. Genetically engineered CARs are contemplated herein. These genetically engineered receptors, CARs, comprise an antigen-specific recognition domain that binds to specific target antigen or cell and a transmembrane domain linking the extracellular domain to an intracellular signaling domain. Design and methods of making CAR are known in the art. In one embodiment, the antigen-specific recognition domain in the extracellular domain redirects cytotoxicity of the effector cell toward tumor cells. In Example 2, a CAR expressing CD19, which is expressed on certain kinds of leukemia or lymphoma, is expressed in T cells derived by these methods and used to kill tumor cells (Riji cells, which are a cell line derived from Burkitt Lymphoma patient).

The T cells produced by the methods herein can be engineered to express CAR specific for tumor or cancer cells, and used in the treatment of such cancers. As is known in the art, a cancer is generally considered as uncontrolled cell growth. Suitable cancers that can be treated using the T cells expressing the engineered CAR receptors include, but are not limited to, hematologic malignancies and solid tumors. Suitable hematologic malignancies are forms of cancer that begin in the cells of blood-forming tissue, such as the bone marrow, or in the cells of the immune system. Examples of hematologic cancer include, but are not limited, to, for example, acute and chronic leukemias, lymphomas, multiple myeloma and myelodysplastic syndromes. The methods of the present invention can be used to treat any cancer, any metastases thereof, including, but not limited to, carcinoma, lymphoma, blastoma, sarcoma, and leukemia. Suitable cancers able to be treated by the compositions, methods and kits described herein include, but are not limited to, for example, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, and peripheral neuroepithelioma. In one embodiment, the cancer is selected from leukemia, lymphoma, melanoma, non-small cell lung cancer, squamous cell carcinoma of the head and neck, ovarian cancer, pancreatic cancer, renal cell carcinoma, hepatocellular carcinoma, bladder cancer, malignant glioma, colorectal cancer, and endometrial cancer.

The term "treating" can be characterized by one or more of the following: (a) the reducing, slowing or inhibiting the growth of tumor cells; (b) preventing the further growth of tumor cells; (c) reducing or preventing the metastasis of tumor cells within a patient, and (d) reducing or ameliorating at least one symptom of the tumor or cancer. In some embodiments, the optimum effective amounts can be readily determined by one of ordinary skill in the art using routine experimentation. As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

As used herein "subject" or "patient" refers to mammals and non-mammals. The term "subject" does not denote a particular age or sex. In one specific embodiment, a subject is a mammal, preferably a human. In some embodiments, the subject suffers from a cancer, particularly a hemotologic malignancy.

Kits

Aspects of the present disclosure that are described with respect to methods can be utilized in the context of the compositions or kits discussed in this disclosure. Similarly, aspects of the present disclosure that are described with respect to the compositions can be utilized in the context of the methods and kits, and aspects of the present disclosure that are described with respect to kits can be utilized in the context of the methods and compositions.

This disclosure provides kits. The kits can be suitable for use in the methods described herein.

In one embodiment, the disclosure provides a kit for culturing a population of AHE cells from human pluripotent cells or mesoderm cells, the kit comprising (1) defined medium sufficient for differentiation of the pluripotent cells into mesoderm cells, (2) an exogenous vector comprising a ETS transcription factor transgene or mRNA comprising a ETS transcription factor transgene; and (3) instructions for introducing the ETS transcription factor into the hPSCs or mesoderm cells and methods for culturing the AHE cells.

In another embodiment, the disclosure provides a kit for culturing AHE cells from mesoderm cells, the kit comprising an inhibitor of the ERK pathway. In one embodiment, the kit comprises a PI3K inhibitor. Instructions for methods of culturing are also provided.

The following non-limiting examples are included for purposes of illustration only, and are not intended to limit the scope of the range of techniques and protocols in which the compositions and methods of the present invention may find utility, as will be appreciated by one of skill in the art and can be readily implemented. The present invention has been described in terms of one or more preferred embodiments, and it should be appreciated that many equivalents, alternatives, variations, and modifications, aside from those expressly stated, are possible and within the scope of the invention.

EXAMPLES

Example 1

Activation of Arterial Program Drives Development of Definitive Hemogenic Endothelium with Lymphoid Potential This Example shows that activation of arterial program through ETS1 overexpression or by modulating MAPK/ERK signaling pathways, at the mesodermal stage of development, dramatically enhanced formation of arterial type HE expressing DLL4 and CXCR4. Blood cells generated from arterial HE were more than 100-fold enriched in T cell precursor frequency and possessed the capacity to produce B lymphocytes and red blood cells exhibiting high expression of BCL11a and □-globin. Together, these findings demonstrated that promotion of arterial specification in cultures provides a novel strategy to generate lymphoid cells and eventually HSCs from hPSCs.

De novo production of hematopoietic and lymphoid cells from in vitro expandable human cells, such as human pluripotent stem cells (hPSCs) can be used for transplantation and immunotherapies of hematologic diseases and cancers. Although the feasibility of generating engraftable hematopoietic cells and T lymphoid cells from hPSCs has been demonstrated[1-5], further translation of these technologies from bench-to-bedside requires development of clinically safe protocols for scalable production of therapeutic cells in defined physiological conditions. Thus, identifying the proper molecular pathways guiding specification of multipotential lymphomyeloid progenitors from hPSCs is essential to advance T lymphoid cell and HSC manufacturing technologies.

During development, blood cells and HSCs arise from hemogenic endothelium (HE). In contrast to the first wave of primitive hematopoiesis lacking of lymphoid and granulocytic potential, definitive hematopoiesis produces the entire spectrum of adult-type erythro-myeloid progenitors (EMP), lymphoid cells, cells capable of limited engraftment (second wave), and HSCs with the capacity for long-term repopulation of an adult recipient (third wave) (reviewed in[6-8]). While some definitive hematopoietic cells such as EMPs can be produced from HE in venous vessels and capillaries[9-11], production of lymphoid cells and HSCs is mostly restricted to arterial vasculature[12-16]. The lack of venous contribution to HSCs when considered along with the shared requirements for Notch, VEGF, and Hedgehog signaling in both arterial fate acquisition and HSC formation[17-21] suggests that arterial specification is an essential prerequisite for establishing of definitive hematopoiesis with lymphoid potential. Although previous studies demonstrated arterial commitment within nonHE fraction of hPSC-derived endothelium[22], little is known about the effect of arterial programming on HE.

This example investigated how arterial programming affects specification of definitive HE and hematopoietic cells from hPSCs. During vascular development, arterial fate is specified following induction of DLL4 expression[23] initiated by signaling through an arterial-specific enhancer located within the third intron of DLL4 that is controlled by ETS factors[24, 25]. Here, the inventors found that arterial program from hPSCs could be enhanced by overexpression of ETS family transcription factor, ETS1. The observed boost in arterial programming by ETS1 was associated with promotion of HE formation with DLL4$^+$CXCR4$^{-/-}$ arterial phenotype and T/B lymphoid and definitive erythroid potentials. In addition, we demonstrated that arterialization of HE and enhancement of definitive hematopoiesis could be achieved through modulating of MAPK/ERK pathways. Promoting arterial patterning in hPSC cultures can be used to aid in vitro approaches to instruct definitive hematopoiesis with lymphoid and HSC potentials from hPSCs.

ETS1 Induction Upregulates SOXF and NOTCH-Signaling Associated Genes and Enhances Arterial Specification To evaluate the effect of ETS1 on arterial programming and hematopoiesis from hPSCs, we engineered H1 human embryonic stem cells (hESC) carrying doxycycline (DOX)-inducible ETS1 transgene (iETS1-hESCs; FIGS. 8A-8D) and differentiated them to endothelial and hematopoietic cells in chemically defined conditions[26]. We treated cultures with DOX beginning at mesodermal stage of development (day 2 of differentiation) and analyzed the expression of the arterial markers DLL4 and CXCR4[23, 27] on CD144$^+$ (VE-cadherin$^+$) endothelial cells emerging on day 4 of differentiation (FIG. 1A). As shown in FIGS. 1B and 1C, DOX treatment increased formation of CD144$^+$ endothelial cells and induced expression of DLL4 and CXCR4 on endothelial cells in a dose-dependent manners. Molecular profiling of endothelial cells isolated on day 4 of differentiation, revealed that ETS1 upregulation led to a marked increase expression of genes associated with arterial specification-associated genes including CXCR4, NOTCH ligand DLL4, NOTCH1, NOTCH4, HEY1, SOXF group genes (SOX7, SOX17, and SOX18), as well as CD93, a gene associated with emerging HSCs in AGM region[24, 27-34], but downregulated the expression of NR2F2 and APLNR venous markers (FIG. 1D). The upregulation of arterial genes was confirmed by RT-qPCR (FIG. 1E). Based on these findings, we concluded that ETS1 upregulation enhances arterial specification from hPSCs.

Figures 2A, 2B, 2C, 2D, 2E:
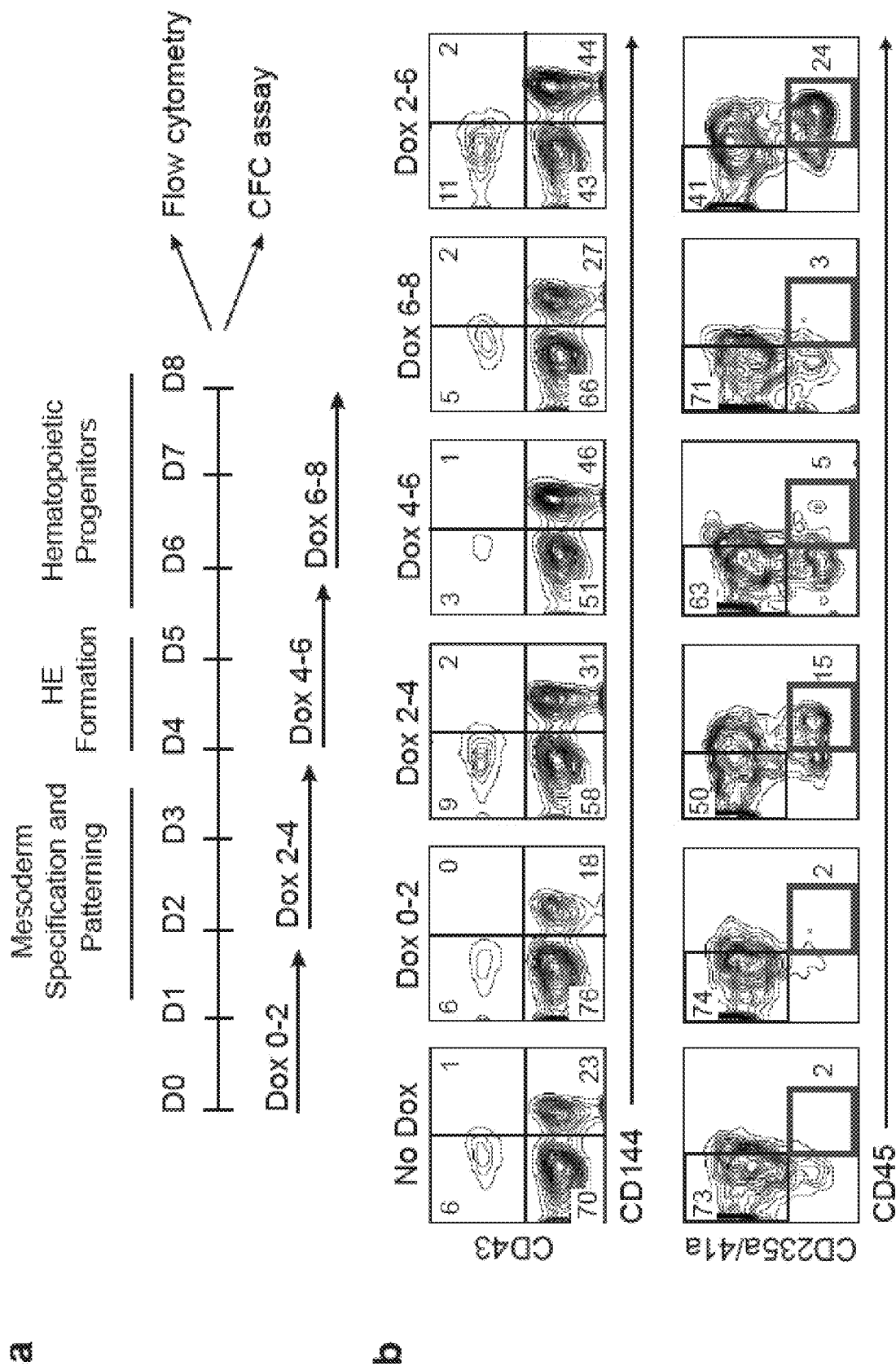
FIGS. 2A-2E show the stage-specific effect of ETS1 on hematopoietic development. (A) Experimental scheme. (B) Flow cytometric analysis of the hematopoietic progenitors obtained from iETS1 hESCs treated with DOX at indicated time points. Representative experiment of three independent experiments is shown. (C) The percentage of hematopoietic and endothelial cells in day 8 of differentiation cultures following DOX treatment at indicated time points. (D) Pie charts display the composition of CD43$^+$ subsets. (E) Hematopoietic colony-forming potential of iETS1 hESCs treated with the DOX at indicated time points. Bar graphs in (C) and (E) are mean±s.d. for two independent experiments performed in duplicates; *p<0.05;p<0.01; *p<0.001 compared to No DOX treatment.

ETS1 induction at mesodermal stage enhances definitive hematopoiesis from hESCs. To determine how ETS1 affects hematopoiesis and whether it's effect on hematopoiesis is associated with activation of arterial program in HE, we treated cells with DOX in a stepwise fashion as depicted in FIG. 2A. In our differentiation system, hPSCs undergo a stepwise progression toward APLNR$^+$PDGFRα$^+$ mesoderm with hemangioblast colony forming cells (HB-CFCs) that reflects primitive hematopoiesis, KDR$^{high}$PDGFRα$^{low/-}$ hematovascular mesodermal progenitors with definitive hematopoietic potential, CD144$^+$CD43$^-$CD73$^-$ definitive HE and CD43$^+$ hematopoietic progenitors which include CD235a$^+$CD41a$^+$ erythromegakaryocytic progenitors (E-MK) and CD235a/41a$^-$CD45$^{+/-}$ hematopoietic progenitors with lin$^-$CD34$^+$CD90$^+$CD38$^-$CD45RA$^-$ hematopoietic stem progenitor cells (HSPC) phenotype[26, 35-37] (FIG. 9A). Stepwise DOX treatment experiments, revealed that upregulation of ETS1 during hematovascular mesoderm and HE specification on days 2-4 or 2-6 of differentiation produced the most profound effect on generation of CD43$^+$ and CD45$^+$ hematopoietic progenitors (FIG. 2B-2C). Importantly, ETS1 upregulation increased the proportion of multipotential CD235a/CD41a$^-$ CD45$^+$ progenitors and GEMM-CFCs (FIGS. 2D and 2E). Typically, colonies from DOX+ were much larger as compared to DOX− cultures (FIG. 2E). ETS1 induction before mesoderm establishment (days 0-2) or post-HE stage (days 6-8) had minimal effect or inhibited blood production (FIG. 2B-2E). Thus, we concluded that the window for the optimal effect of ETS1 on hematopoiesis coincided with amplification of arterial program by ETS1.

Figures 3A, 3B, 3C, 3D, 3E, 3F:
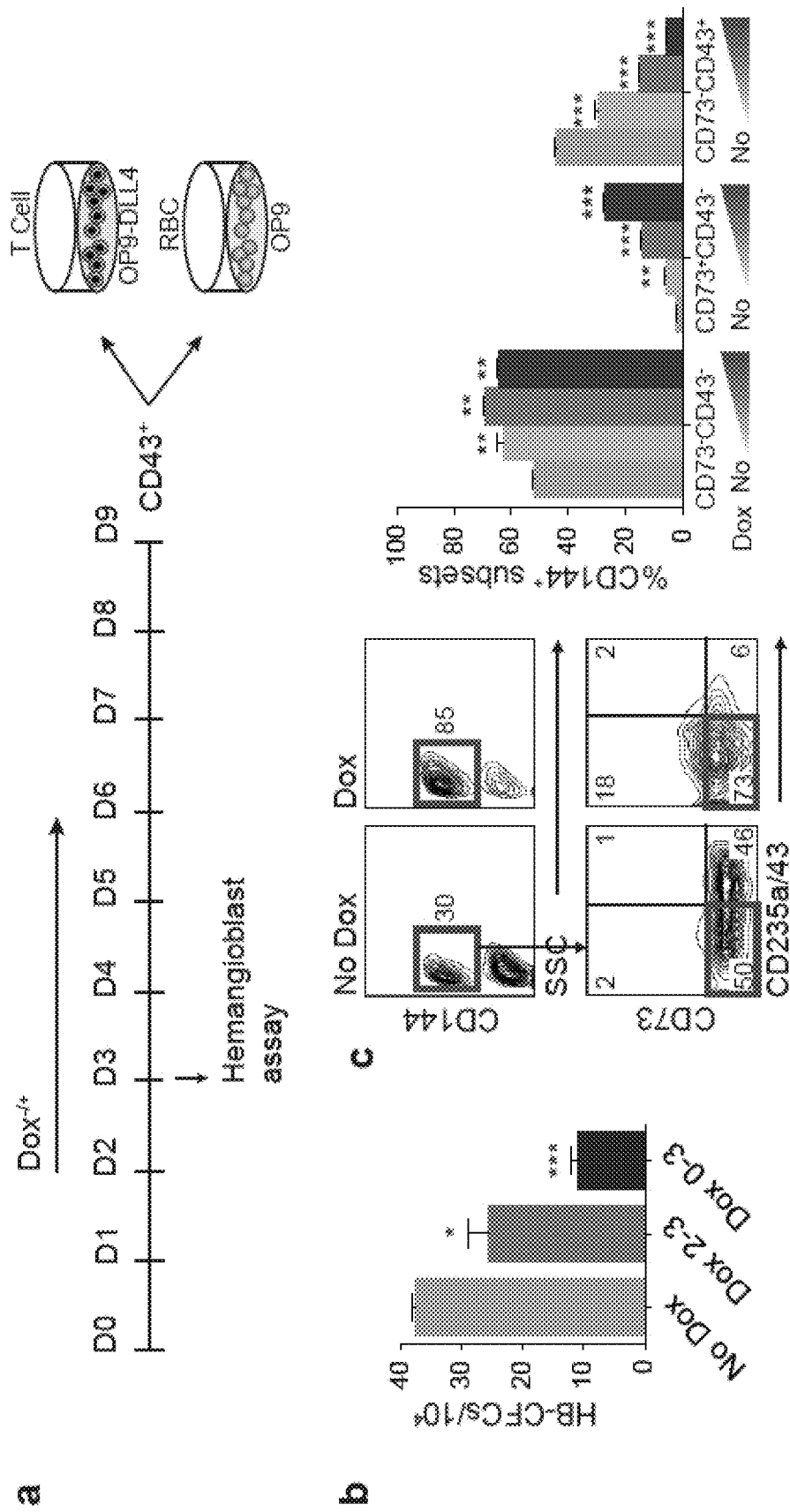
FIGS. 3A-3F demonstrate that ETS1 induction suppresses primitive and promotes definitive hematopoiesis. (A) Experimental scheme. (B) Effect of ETS1 induction on hemangioblast (HB)-CFCs. (C) Flow cytometric analysis shows the increase of CD144$^+$ CD73$^-$ CD235a/43$^-$ HE population at day 5 of differentiation of iETS1-hESC cultures treated with DOX for 2-5 days. (D) CD43$^+$ cells generated in DOX-treated and No-DOX cultures possess T cell potential. Representative experiment of 3 independent experiments shows the expression of T cell markers on CD45-gated cells in T cell differentiation cultures. (E) Bar graph shows the total number of T cells generated from 10$^4$ CD43$^+$ cells obtained from iETS1-hESCs in DOX-treated and untreated conditions. (F) Ratio of β/ε and β/γ globin chain and BCL11a gene expression as measured by RT-qPCR in red blood cell cultures generated from CD43$^+$ cells obtained from DOX-treated and untreated iETS1-hESC cultures. Bar graphs in (B), (C), (E) and (F) are mean±s.d. of at least three independent experiments. *p<0.05; p<0.01; *p<0.001 compared to No DOX treatment.

To define which type of hematopoiesis is affected by ETS1 overexpression, we evaluated the effect of DOX treatment on i) hemangioblast (HB) CFCs that reflect the primitive wave of hematopoiesis[37, 38] and ii) on T lymphocytes and β-hemoglobin-producing red blood cells that reflect definitive hematopoiesis (FIG. 3A)[37, 39]. When cultures were treated with DOX on day 2 of differentiation, we observed on day 3 a significant decrease in APLNR$^+$PDGFRα$^+$ primitive mesodermal cells and HB-CFCs compared to control. This effect was more profound when cultures were treated with DOX from day 0 through day 3 to ensure maximum ETS1 overexpression on day 3 (FIG. 3B and FIGS. 9B-9C). In contrast, DOX treatment starting from day 2 of differentiation increased formation of CD144$^+$CD43$^-$CD73$^-$ definitive HE[37] on day 5 of differentiation in a dose-dependent manner (FIG. 3C). To determine the effect of ETS1 upregulation on T cell potential, we collected CD43$^+$ cells from DOX+ and DOX− cultures and subcultured on OP9-DLL4 stromal cells. Although cells collected from both conditions generated a similar percentage of CD5$^+$CD7$^+$ and CD4$^+$CD8$^+$ T lymphoid cells (FIG. 3D), CD43$^+$ cells from DOX+ cultures produced a dramatically (~8 fold) greater number of T lymphoid cells per $10^4$ of CD43 cells (FIG. 3E). In addition, we found that CD43 cells collected following DOX treatment and cultured in erythroid conditions upregulated adult β-hemoglobin and BCL11a genes associated with definitive erythropoiesis[40] (FIG. 3F). Overall, these studies suggest that ETS1 upregulation suppresses primitive and promotes definitive hematopoiesis from hPSCs, most likely through enhancement of definitive HE specification at the mesodermal stage.

Figures 4A, 4B, 4C, 4D, 4E, 4F, 4G, 4H, 4I:
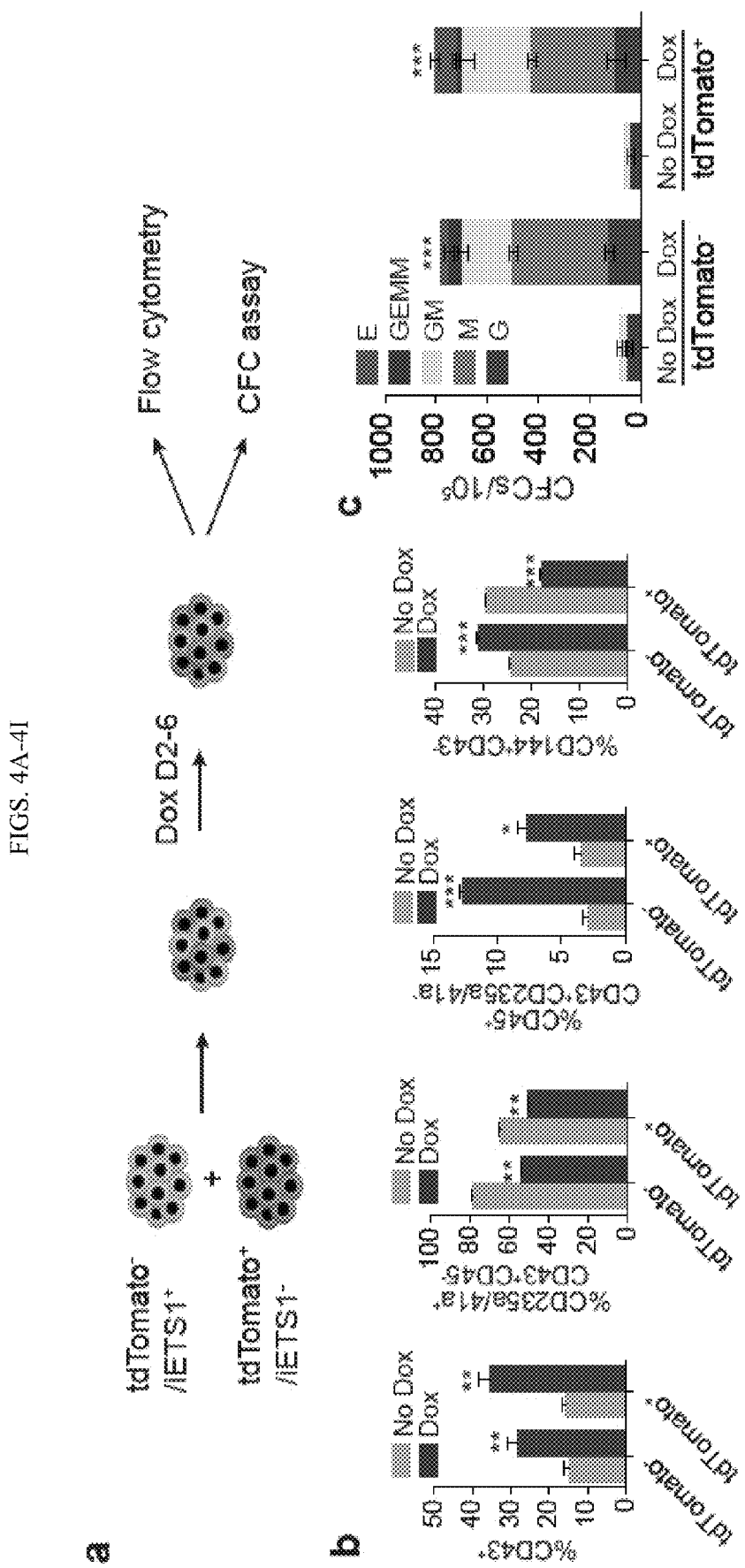
FIGS. 4A-4I demonstrate that ETS1 induction promotes hematopoiesis through upregulation of NOTCH signaling. (A) Schematic diagram of experiment with chimeric hESC cultures. Mixture of iETS1 (tdTomato$^-$) and tdTomato$^+$ H1 hESCs were cultured with or without Dox (2 µg/ml) for 2-6 days during hematopoietic differentiation in chemically defined culture conditions. (B) Flow cytometric analysis of hematopoietic development on day 8 of differentiation following gating tdTomato$^+$ or tdTomato$^-$ (iETS1) cells in DOX-treated and untreated cultures. (C) Hematopoietic colony-forming potential of tdTomato$^+$ or tdTomato$^-$ cells. (D) Flow cytometric analysis of DLL4 expression in day 4 KDR$^+$ CD144$^+$ population following gating tdTomato$^-$ or tdTomato$^-$ (iETS1) cells in DOX-treated and untreated cultures. (E) Schematic diagram of experiment to assess the role of NOTCH signaling in ETS1-mediated effect on hematopoiesis. The effect of DAPT treatment on blood production (F) and CFC potential (G) in cultures treated with DOX. The effect of DLL4 neutralizing antibodies on blood production (H) and CFC potential (I) in cultures treated with DOX. Bar graphs in (B), (C), (G) and (I) are mean±s.d. of three independent experiments; *p<0.05, p<0.01; *p<0.001.

ETS1 Overexpression Promotes Definitive Hematopoiesis Through NOTCH-Mediated Signaling To determine whether ETS1 induction promotes definitive hematopoietic program in a cell-autonomous or non-autonomous manner, we mixed tdTomato (tdT) transgenic H1 hESC with iETS1 H1 hESCs and analyzed hematopoietic development from chimeric cultures with and without induction of ETS1 expression (FIG. 4A).

These studies revealed that ETS1 upregulation enhanced the production of CD43$^+$ hematopoietic progenitors, including CD45$^+$ progenitors, from both, tdT$^+$ and tdT$^-$ cells (FIG. 4B and FIG. 10). When cells were collected and assayed for CFC potential, the number of hematopoietic colonies in both tdT$^+$ and tdT$^-$ were increased following DOX treatment (FIG. 4C). Interestingly, endothelial cells in D4 tdT$^-$ fraction expressed greater levels of DLL4 as compared to tdT$^+$ cells (FIG. 4D).

These results suggest that ETS1 overexpression expands DLL4-expressing arterial endothelial cells, and promotes definitive hematoendothelial program through upregulation of NOTCH signaling.

To confirm the role of NOTCH activation in promoting definitive hematopoiesis by ETS1, we evaluated hematopoiesis following ETS1 upregulation in the presence of NOTCH signaling inhibitor DAPT, and DLL4 neutralizing antibodies (FIG. 4E). As shown in FIG. 4F-4I, treatment of hESC cultures with NOTCH signaling inhibitor DAPT, or DLL4 antibodies, abrogated effect of ETS1 upregulation on hematopoiesis, thereby confirming the important role of DLL4 expression and NOTCH activation in ETS1-mediated promotion of definitive hematoendothelial program.

ETS1 overexpression induces HE with DLL4+CXCR4+ arterial phenotype.

Figures 5A, 5B, 5C, 5D, 5E, 5F, 5G, 5H, 5I, 5J, 5K:
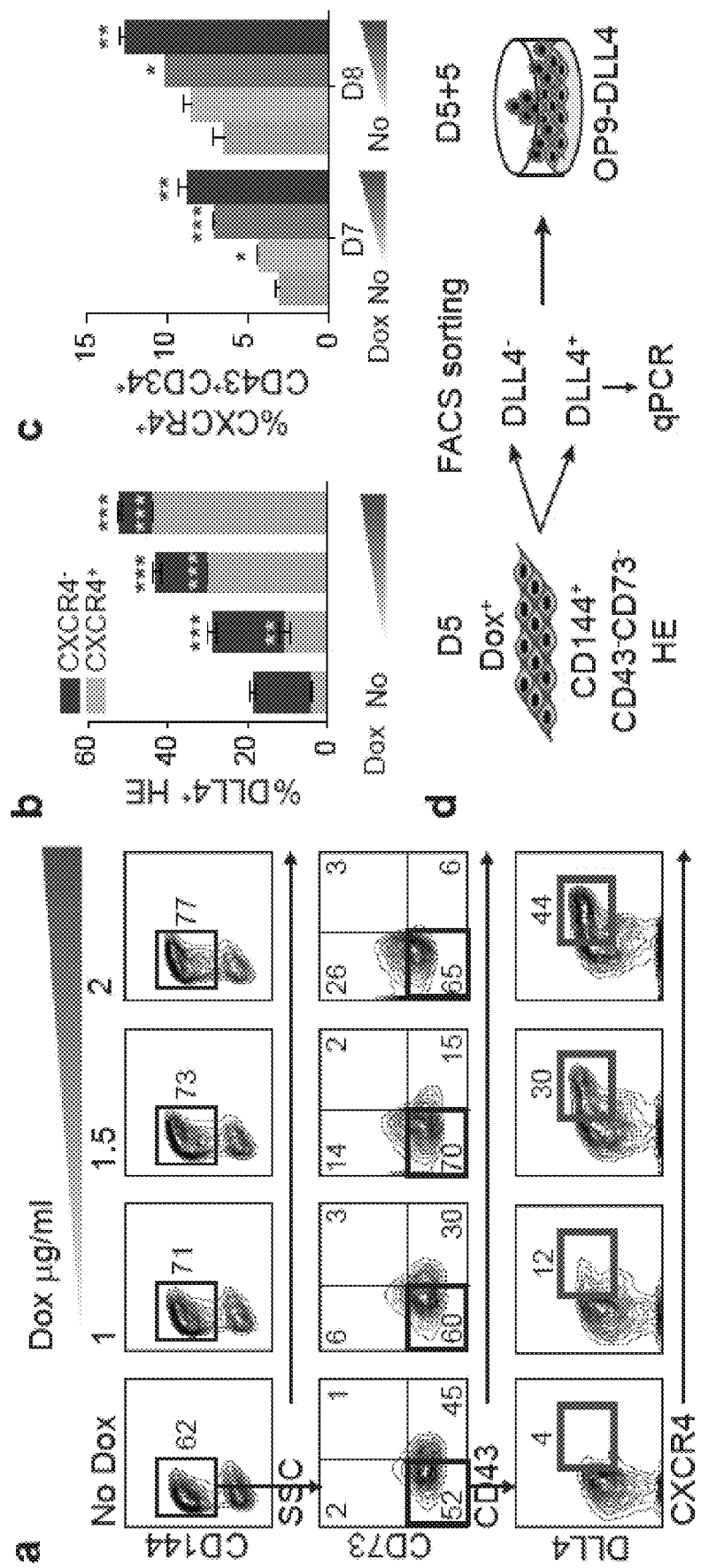
FIGS. 5A-5K demonstrate that ETS1 promotes specification of arterial type HE. (A) and (B) DOX treatment enhances specification of DLL4$^+$ CXCR4$^{+/-}$ arterial type HE in dose-dependent manner. (C) DOX-treatment enhances production of CD34$^+$ CD43$^+$ hematopoietic progenitors expressing CXCR4$^+$ in a dose-dependent manner. (D) Schematic representation of the experimental strategy to assess hematopoietic potential of DLL4$^+$ and DLL4$^-$ HE. (E) RT-qPCR analysis of arterial genes in DLL4$^+$ and DLL4$^-$ HE. Hematopoietic (F) and CFC (G) potential of DLL4$^+$ and DLL4$^-$ HE. (H) Ratio of β/ε and β/γ globin chain and BCL11a gene expression as measured by RT-qPCR in red blood cell cultures generated from DLL4$^+$ and DLL4$^-$ HE. (I) B cell potential of DLL4$^+$ and DLL4$^-$ HE. (J) T cell potential of DLL4$^+$ and DLL4$^-$ HE. Flow cytometry plot depicts percentage of CD4$^+$ CD8$^+$ T cells. Bar graph shows the total number of T cells generated from 10$^4$ CD43$^+$ cells obtained from DLL4$^+$ and DLL4$^-$ HE. (k) Limiting dilution assay to determine frequency of T cell progenitors in DLL4$^+$ and DLL4$^-$ HE cultures. Bars in (B), (C), (E)-(J) are mean±s.d. of at least three independent experiments; *p<0.05, p<0.01; *p<0.001.

Although previous studies found that DLL4+ endothelial cells in hPSC cultures have reduced hematopoietic potential as compared to DLL4− cells[22, 41], we noticed that increased definitive hematopoietic cell production following ETS1 overexpression was correlated with marked increase of DLL4+ and DLL4+CXCR4+ fraction within the CD144+ CD43−CD73− HE population (FIGS. 5A and 5B), thereby suggesting that enhancement of the definitive hematopoietic program could be attributed to DLL4+ HE population that acquires arterial characteristics, as determined by analysis of EFNB2, SOX17 and NOTCH1 arterial markers by RT-qPCR (FIG. 5E). To determine whether arterial type HE has hematopoietic potential, we sorted DLL4+ and DLL4− cells and assessed blood formation from them following 5 days secondary culture on OP9–DLL4 (FIG. 5D). Although DLL4+ produced a relatively lower number of CD43+ cells, the proportion of multipotential CD235a/CD41a−CD45+ progenitors was greater in DLL4+ cultures compared to DLL4− (FIG. 5F). Hematopoietic progenitors collected from DLL4+ HE also produced a greater number of multipotential CFC-GM and -GEMM (FIG. 5G) and generated erythroid cells with substantially higher expression of adult β-hemoglobin and BCL11a (FIG. 5H). Importantly, the most significant difference was observed in the lymphoid potentials of DLL4+ and DLL4− HE (FIG. 5I-5K). As shown in FIG. 5I, only DLL4+ cells had B cell potential. While both DLL4+ and DLL4− cells possessed T cell potential (FIG. 5J), the limiting dilution analysis revealed more than a 100-fold enrichment in T cell progenitors in DLL4+ fraction. Interestingly, we have previously shown that in contrast to fetal liver HSCs, PSC-derived hematopoietic progenitors have decreased expression of HSC homing receptor CXCR4[42]. As demonstrated in FIG. 5C, following ETS1 induction, not only HE, but CD34+CD45+ hematopoietic progenitors upregulated CXCR4 expression.

Together, these data suggest that arterial specification of HE is associated with acquisition of definitive hematopoietic program. To further characterize DLL4− arterial HE, we evaluated hematopoietic potential of CXCR4+ and CXCR4− cells (FIG. 11A). As shown in FIGS. 11B-11E, both CXCR4+ and CXCR4− fractions of DLL4+ HE cells generated multipotential CFCs and T cells. However, a more than 3-fold enrichment in the T cell progenitors was observed in blood cells generated from CXCR4+ cells.

Promotion of Arterial Specification of HE and Definitive Hematopoiesis by Modulation of MAPK/ERK Signaling Arterial specification in the embryo is modulated by multiple pathways, including MAPK/ERK signaling. It has been shown, that indirect ERK activation through inhibition of Phosphoinositide 3-kinase (PI3K) downstream of VEGF receptor signaling, enhances arterial specification in zebrafish, while inhibition of ERK branch blocks arterial specification[43, 44]. To determine whether modulating MAPK/ERK signaling affects arterial specification of HE from hPSCs, we treated differentiation cultures on days 3 through day 6 with PI3K inhibitor LY294002, or MEK1 and MEK2 inhibitor U0126 (FIG. 6A). Indeed, we revealed that treatment with LY294002 enhanced production of DLL4+ arterial type HE, including the DLL4+CXCR4+ fraction, while U0126 treatment almost completely abrogated formation of DLL4+HE (FIGS. 6B and 6C). We also observed a direct correlation between definitive hematopoiesis efficacy and arterial specification. When ERK pathways were activated following HE specification, production of multipotent CD235a/CD41a−CD45+ hematopoietic progenitors and CFC potential was dramatically increased, while ERK inhibition abrogated production of these types of cells (FIG. 6D-6F). In addition, T lymphoid potential was significantly increased in cultures treated with LY294002 and entirely abrogated in cultures treated with U0126. Overall, these observations provide additional evidence for our hypothesis that enhancing arterial specification of HE is essential to establish a definitive hematopoietic program with lymphomyeloid potentials from hPSCs.

Figures 7A, 7B:
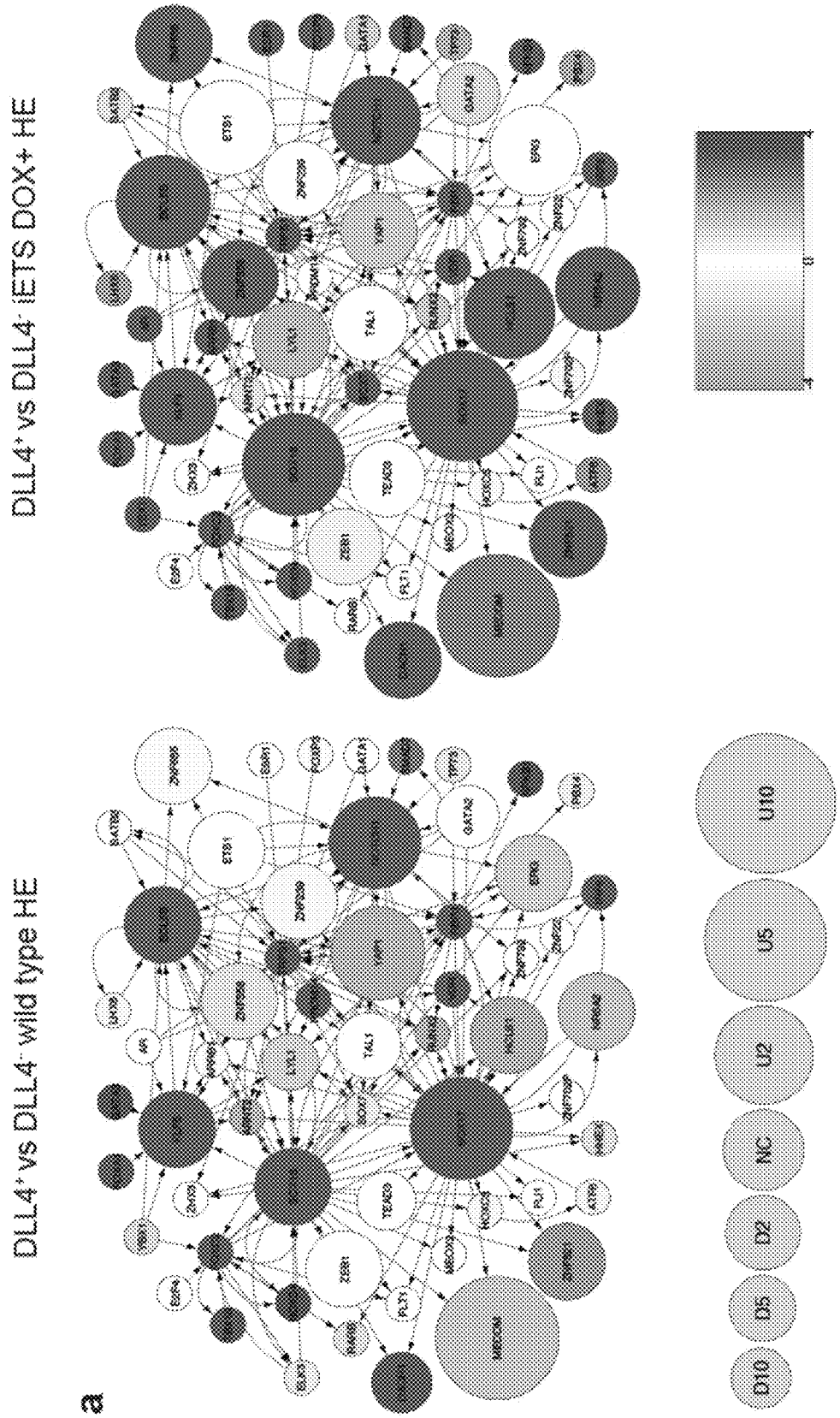
FIGS. 7A-7B demonstrate that gene expression profiling reveals activation of NOTCH and SOXF$^-$ mediated transcriptional programs in DLL4$^+$ arterial HE. (A) Transcriptional regulatory network reconstructed based on analysis of differentially expressed genes in DLL4$^+$ and DLL4$^-$ HE cells as described in materials and methods. Size of the nodes represents relative abundance of mRNA of the respective gene, computed as log 2 (fold change) in DLL4$^+$ and DLL4$^-$ HE cells. Both up- and down-regulation effects are mapped onto the node size. The color density represents enrichment (red) or depletion (blue) of known targets of that transcription factor (regulon members) among the differentially expressed genes. Network visualization was performed using Cytoscape ver. 3.4.0$^{62}$. (B) Schematic of arterial HE induction from hPSCs by overexpression of ETS1 or modulation of MAPK/ERK signaling pathways.

NOTCH and SOXF-Mediated Transcriptional Program is Activated in DLL4+ Arterial HE To determine the molecular program associated with establishing arterial HE, we performed RNAseq analysis of DLL4+ and DLL4− HE. As a basis for the analysis, genes that were differentially expressed in a 3-way Bayesian model involving DLL4+ vs DLL4− wild type HE and DLL4+ vs DLL4− iETS1 HE from DOX cultures (FIG. 12—Supplementary Table S1) were used. The transcriptional network relevant to the observed responses was visualized as described in Methods. Every node of the network reflects both regulon-level signal strength related to a particular transcription factor and the change in mRNA level of the transcript of the gene encoding that transcription factor. The relative abundance of mRNA expression in these networks was coded as a node size, while color density represents enrichment (red) or depletion (blue) of known targets of that transcription factor (regulon members) among the differentially expressed genes. As shown in FIG. 7A, the increased expression and regulon activity for NOTCH1, SOXF (SOX17, SOX18), KLF5 and BCL6B genes was a distinct feature of DLL4+ arterial HE from wild type and iETS1 hESCs in DOX cultures, although these features were more pronounced in iETS1 DLL4+ HE. As previously shown, proinflammatory signaling plays an important role in HSC development[45, 46]. Interestingly, the regulons of NFKB1 and IRF6 factors were activated in DLL4− cells suggesting that arterialization of HE is associated with activation of proinflammatory signaling. Despite ETS1 overexpression in DOX cultures, ETS1 regulon signal in iETS1–DLL4+ HE was poor. This is consistent with our findings that the effect of ETS1 is primarily mediated through upregulation of signaling from NOTCH1 and likely SOXF transcription factors, rather than from any immediate activity of ETS1. Overall, these studies suggest that activation of arterial program in HE is primarily driven by the NOTCH and SOXF-driven transcriptional programs.

In present example, the inventors demonstrated that definitive hematopoiesis from hPSCs could be promoted through activation of arterial program in HE through a number of mechanisms: overexpression of transcription factors ETS1, which has the capacity to activate arterial-specific enhancer in the third intron of DLL4 gene[24,25], through modulation of MAPK/ERK signaling by small molecules, or through upregulation of NOTCH signaling. These approaches induced formation of DLL4+CXCR4+/− arterial type HE that is highly enriched in definitive hematopoietic progenitors with T and B lymphoid potentials. In addition, arterial program activation enhanced production of CD34+CD43+ hematopoietic progenitors expressing HSC homing receptor CXCR4, which is typically not present in hematopoietic progenitors in traditional hESC differentiation cultures[42]. DLL4 is expressed by HE underlying intra-aortic hematopoietic clusters in the AGM[47] and recent mouse studies have revealed significant enrichment in pre-HSCs in the DLL4+ fraction of AGM HE[48]. Thus, our in vitro findings correlate with in vivo observation and suggest that induction of HE arterialization is critical to mimic the proper specification of definitive hematopoiesis and HSC formation from hPSCs in vitro.

Discovering the important role of arterial programming in lymphoid development from PSCs, allowed us to significantly improve T cell progenitor production in defined conditions by applying small molecules to enhance formation of arterial type HE. Scalable T cell production is essential to advance translation of iPSC-based immunotherapies into the clinic. However, in vivo studies from ETS1-induced cultures have failed to show the evidence of long-term engraftable cells (data not shown). Molecular profiling and functional studies of PSC-derived phenotypical HSCs in human and mouse system have revealed multiple pathway deficiencies in in vitro generated cells as compared to their in vivo counterparts, including lacking of Notch-signaling signature, and deficiency of HOXA and AP-1 complex genes that are functioning independently of arterial programming[1, 42, 49]-51. In addition, studies in zebra fish revealed that HSC specification is also regulated by mechanisms uncoupled from arterial patterning[21,52,53]. Thus, arterial specification of HE per se may not be sufficient for HSC formation. Further exploration of the interplay between mechanisms coupled and uncoupled with arterial specification, and deciphering kernels for the gene regulatory network required for HSC development, will be essential for further advancing HSC generation for clinical purposes.

Experimental Procedures hESC Lines Maintenance and Hematopoietic Differentiation H1 hESCs were obtained from WiCell Research Institute (Madison, Wis.). H1 hESC line, the iETS1 H1 hESC line and the tdTomato H1 hESCs line were maintained on Matrigel™ in mTeSR1™ medium. Cells were passaged every 3-4 days using 0.5 mM EDTA in PBS. The hESC lines were differentiated on ColIV coated plate as previously described in details[26].

Construction of Vectors and Generation of iETS1 and tdTomato H1 hESC Lines

Human ETS1 cDNA was cloned into PiggyBac transposon vector (Transposagen) downstream of TREtight promoter of pTRE-P2A-Venus-EF1α-Zeo plasmid, and then co-electroporated with pEF1α-M2rtTA-T2A-Puro and transposase plasmid into H1 hESCs using Amaxa® human stem cell nucleofector kit 2 (Lonza) (FIG. 8). The colonies were selected in Zeocin (0.5-1 µg/ml, Invitrogen) and Puromycin (0.5-1 µg/ml, Sigma) for 10-15 days and the resistant clones were screened by Venus expression under a fluorescence microscope with DOX treatment. The tdTomato cDNA was cloned downstream of EF1α promoter of a pRMCE-EF1α-Zeo plasmid and into H1 hESCs. 3 days after electroporation, cells were treated with Zeocin (0.5-1 µg/ml, Invitrogen). After 10-15 days, tdTomato positive surviving colonies were picked out and expanded in each well of a 12 well plate.

Hemangioblast (HB)-CFC and Hematopoietic CFC Assay

HB-CFCs were detected as described previously[54]. HB-CFCs were detected using the semisolid colony-forming serum-free medium (CF-SFM) containing 40% ES-Cult M3120 methylcellulose (2.5% solution in IMDM, Stem Cell Technologies), 25% StemSpan™ serum-free expansion medium (SFEM, Stem Cell Technologies), 25% human endothelial serum-free medium (ESFM, Invitrogen), 10% BIT 9500 supplement (Stem Cell Technologies), GlutaMAX™ (1/100 dilution, Invitrogen), Ex-Cyte™ (1/1000 dilution, Millipore), 100 µM MTG, 50 µg/ml ascorbic acid and 20 ng/ml FGF (Peprotech). Hematopoietic CFCs were detected using serum containing H4435 MethoCult with FGF, SCF, IL-3, IL-6 and EPO (Stem Cell Technologies).

Assessment of Hematopoietic Potential of DLL4$^-$ and DLL4$^+$CXCR4+/− HE.

The iETS1 DOX-treated cells from day 5 of culture were dissociated into single cells by treatment with 1× TrypLE and stained with DLL4-PE, CD144-PerCPVio700, CD43-APC and CD73-BV421 antibodies and then sorted using a FACSAria II cell sorter (BD Biosciences) for isolation of DLL4$^+$ and DLL4$^-$ HE. For isolation of CXCR4$^+$ and CXCR4$^-$ DLL4$^+$ HE, cells were stained with DLL4-PE, CD144-PerCPVio700, CXCR4-PEVio770, CD73-APC and CD43-APCVio770 antibodies and sorted using a FACSAria cell sorter (BD Biosciences). Isolated day 5 DLL4$^+$CD144$^+$CD73$^-$CD43$^-$ and DLL4$^-$CD144$^+$CD73$^-$CD43$^-$HE, or CXCR4$^+$DLL4$^+$CD144$^+$CD73$^-$CD43$^-$ and CXCR4$^-$DLL4$^+$CD144$^+$CD73$^-$CD43$^-$HE were cultured at a concentration of 4×10$^4$ cells per well on a monolayer of Mitomycin C (Cayman Chemicals)-pretreated OP9 cells expressing human DLL4 (OP9-DLL4) in medium with SCF (50 ng/ml), TPO (50 ng/ml), IL-3 (10 ng/ml) and IL-6 (20 ng/ml, all cytokines from PeproTech) in 6-well plates as we described previously[55]. After 5 days of cultures on OP9-DLL4, cells were harvested and analyzed by flow cytometry. The floating CD43$^+$ cells were collected for T cell or RBC differentiation.

T and B Cell Differentiation

T cell differentiation of hESC-derived hematopoietic precursors was performed on the OP9-DLL4 in T cell differentiated medium consisting of α-MEM (Gibco) supplemented with 20% FBS (Hyclone), 5 ng/ml FLT3L, 5 ng/ml IL-7 and 10 ng/ml SCF (all from PeproTech) as described previously[26]. For B cell differentiation, sorted DLL4$^+$ and DLL4$^-$ HE cells were cocultured on OP9 for 4 weeks in αMEM medium containing 20% FBS, FLT3L (5 ng/ml, PerproTech) and IL7 (5 ng/ml, PerproTech). Cultures were fed with complete media changes weekly. Presence of B cells was confirmed via staining with CD19 APC (Miltenyl Biotech) and CD10 PE (BD Biosciences) antibodies.

Limiting Dilution Assay to Determine Frequency of T Cell Progenitors

Limiting Dilution Assays were conducted with the floating cells (CD43$^+$) collected from day 5+5 cultures (DLL4$^+$ and DLL4$^-$ HE or CXCR$^+$ and CXCR$^-$DLL4$^+$ HE) on OP9$^-$DLL4. Row A of a 96-well plate received 500 cells/well, and each subsequent row afterwards received half the previous row (e.g. Row B contained 250, Row C contained 125, etc, until eventually Row H contained 3-4 cells). Wells were assessed 2 weeks later under microscope for presence of floating blood cells and by flow-cytometry for CD5$^+$CD7$^+$ expressing cells. Extreme limiting dilution analysis was conducted using a previously established algorithm[56].

RBC Differentiation

Floating CD43− cells at day 9 of differentiation were collected and cultured in RBC differentiated medium consisting of SFEM (serum free expansion medium, Stem Cell Technologies) supplemented with 0.3% Ex-Cyte (Millipore), 1 mg/ml HoloTransferrin (Sigma), 10 µM dexamethasone, 20 ng/ml insulin (Sigma), 2U/ml EPO, 50 ng/ml SCF, 50 ng/ml TPO, 5 ng/ml IL-3 and 10 ng/ml IL-6 on ultra-low attachment 6 well plate (Corning). After 2 days, cells were cultured on OP9 cells using the same medium without TPO, IL-3 and IL-6 for 20 days with weekly passage. Media changes were performed every 2 days as described previously[57].

Flow Cytometry

Cells were analyzed using MACSQuant Analyzer (Miltenyi Biotec) and FlowJo software (Tree star). Cell surface staining utilized the antibodies listed in FIG. 12.

DAPT and DLL4 Antibody Treatment

Notch signaling was blocked by DAPT (γ-secretase inhibitor/GSI, 10 µM, Cayman Chemicals) or DLL4 blocking antibody (10 µg/ml, Creative BioLabs)

LY294002 and U0126 Treatment

MAPK/ERK pathway was activated using LY294002 (2 µM, Cayman Chemicals) and was inhibited using U0126 (1 µM, Cayman Chemicals)

Quantitative Real Time PCR

Total RNA was isolated using the RNeasy® Plus Micro Kit (Qiagen). RNA was reverse transcribed into cDNA using Oligo(dT) with ImProm-II Reverse Transcriptase (Promega). Real time quantitative PCR was performed in triplicates using SYBR Advantage qPCR Premix (Clontech) on Mastercycler® ep realplex (Eppendorf). Gene expression was evaluated as DeltaCt relative to the RPL13A gene. Primer sequences are listed in FIG. 13.

Western Blot

Cells were suspended in lysis buffer containing 17 mM Tris pH 8.0, 50 mM NaCl, 0.3% Triton X-100, 0.3% NP-40 and a protease inhibitor cocktail tablet (Roche, Switzerland). ETS1 and GAPDH were detected with anti-ETS1 (Santa Cruz Biotechnology, sc-55581) and anti-GAPDH (Santa Cruz Biotechnology) antibodies, respectively.

Low Level RNAseq Data Processing.

Day 4 KDR$^+$CD144$^+$ or day 5 DLL4$^+$ and DLL4$^-$ HE cells were isolated from DOX treated and untreated cultures as described above. Total RNA was prepared with RNeasy Plus Micro Kit (Qian). RNA purity and integrity was evaluated by capillary electrophoresis on the Bioanalyzer 2100 (Agilent Technologies, Santa Clara, Calif.). Samples were then prepared for sequencing using the Ligation Mediated Sequencing (LM-Seq) protocol, according to the published guidelines[58]. Final sample libraries were quantitated with the Life Technologies Qubit fluorometer and sequenced on the Illumina HiSeq 3000 (SY-401-1003-PRE). Base-calling and demultiplexing were completed with the Illumina Genome Analyzer Casava Software, version 1.8.2. Following quality assessment and filtering for adapter molecules and other sequencing artifacts, the remaining sequence reads were aligned to transcript sequences corresponding to hg19 human genome annotation. Bowtie v 1.1.2 was used, allowing two mismatches in a 25 bp seed, and excluding reads with more than 200 alignments[66]. RSEM v 1.3.0 was used to estimate isoform or gene relative expression levels in units of "transcripts per million" (tpm), as well as posterior mean estimate of the "expected counts" (the non-normalized absolute number of reads assigned by RSEM to each isoform/gene)[10,67]. R statistical environment (R core team, 2014) was used throughout all of the stages of downstream data analysis.

Downstream RNAseq Boinformatics Analysis: Testing for Differential Expression

R statistical environment (R core team, 2014) was used for all stages of downstream data analysis. The entire set of libraries were pre-normalized as a pool to equilibrate 65th percentile of the counts distribution, using the quantile scaling routine from EBSeq package[59]. For each gene, maximal counts across all the samples were plotted and the genes representing the lower mode of the distribution were filtered out (only genes that have at least 40 counts in at least 1 sample were retained), restricting the set of genomic features to 12,898. Additional median scaling was applied to the pre-filtered set of genes. Differential expression was called using EBSeq with 10 iterations. The EBSeq's default procedure of filtering low-expressed genes was suppressed by setting the QtrmCut parameter to zero. Genes with an assigned value of Posterior Probability of Differential Expression above 0.95 were preliminarily selected. Genes that passed two additional filters were selected for downstream analysis: 1) fold change cutoff of 1.5 and 2) expression level should exceed $20^{th}$ percentile of genome-wide distribution of expression values in libraries representing the condition with a larger mean expression of that gene.

Visualization of Transcriptional Network

Using the known transcription-target relationships obtained by combining largely complementary data from HTRIdb[60] and CellNet[61], we generated combined sets of targets for 950 transcriptional regulators that involve 130,855 individual transcription factor (TF)-target interactions, for regulon analysis. To visualize the cascades of transcriptional regulation that involve influence of active TFs on TF-encoding genes, we restricted the overall regulatory network to TF-target relationships that involve TF-encoding target genes. The resulting "transcriptional backbone" network has 837 regulators and reduced by over an order of magnitude (12,372) individual TF-target relationships. To isolate the relevant part of this network, we selected 8 transcription factors that demonstrated their activation in response to Dox according to our regulon analysis, and restricted the network to edges that have either outgoing or incoming connections related to the 8 selected factors. The resulting subnetwork had 59 nodes and 175 edges. Accession codes: The RNAseq data has been deposited in Gene Expression Omnibus under accession number GSE96815. Access code while in private status: ktwzakaohxsbryv.

Example 2

NOTCH Activation at the Definitive Mesoderm Stage Facilitates Efficient Generation of T Cells with High Proliferation Potential from Human Pluripotent Stem Cells Adoptive T cell therapies show promise in the treatment of several types of blood cancers. Developing off-the-shelf T cell products will further advance immunotherapies to the clinic and broaden their application. Human pluripotent stem cells (hPSCs) offer the potential to serve as a versatile and scalable source of T cells for immunotherapies, which could be coupled with genetic engineering technologies to meet specific clinical needs. However, production and expansion of T cells from hPSCs remains inefficient. In order to improve T cell production from hPSCs it is essential to identify cell subsets that are highly enriched in T cell progenitors, and those stages of development at which NOTCH activation induces the most potent T cells. Previously, we have developed both OP9-based and chemically defined systems for hematopoietic differentiation from iPSCs (Vodyanik et al., 2006 and Uenishi et. al, 2014). In these differentiation systems, hPSCs undergo stepwise progression towards APLNR+PDGFRa+ mesoderm with hemangioblast colony forming cells (HB-CFCs) that reflect primitive hematopoiesis (day 3 of differentiation), KDR$^{hi}$tPDGFRa$^{low/-}$ hematovascular mesodermal progenitors (HVMP) with definitive hematopoietic potential, VE-cadherin (VEC)+CD43−CD73−HE with definitive hematopoietic potential (day 4-5 of differentiation) and CD43+ hematopoietic progenitors, including CD235+CD41+ erythromegakaryocytic progenitors (E-MkP) and CD235a/41a−

CD45+/– multipotent hematopoietic progenitors (MHP) that have lin-CD34+CD90+CD38–CD45RA– hematopoietic stem progenitor cells (HSPC) phenotype (days 6-8 of differentiation) (FIG. 14).

To assess the stage at which NOTCH activation induces the most potent T cells, we isolated the aforementioned blood forming populations and cultured them in T cell conditions on OP9–DLL4. This example shows that Day 3 APLNR+PDGFRa+ primitive posterior mesodermal cells did not produce T cells, while all downstream subsets except CD235a+CD41a+CD45– cells do produce T cells when cultured on OP9–DLL4. As determined by limiting dilution assay, the highest frequency of T cell precursors was detected from day 4 HVMP (1 in 14 HVMP). The frequency of T cell precursors in day 5 HE and day 8 HPs was 1 in 16 HEs and 1 in 20 MHPs, respectively (FIG. 15).

In addition, this example demonstrates that T cells generated from HVMPs have the capacity to proliferate for 8 weeks, in comparison to HEs and MHPs subsets, which could only be expanded for 4-5 weeks (FIG. 16). T cell differentiation from hPSCs proceeds through a CD5+CD7+ progenitor stage that eventually transitions into CD8+CD4+ double positive cells (~90%), CD3+TCRa/b+ and CD3+ TCRg/d+ cells. To confirm T cell development, the genomic DNA of the hematopoietic cells from OP9–DLL4 cultures was analyzed for the presence of T cell receptor (TCR) rearrangements. This analysis demonstrated the presence of multiple PCR products of random V-J and D-J rearrangements at the β locus and V-J rearrangements at the γ locus, indicative of a polyclonal T lineage repertoire. In vitro generated T-cells were functionally active and proliferated upon stimulation with PMA and IL-2 (FIG. 17). Upon activation, the cells express CD25+CD69+ (~73%) markers, cytokines (IFN-γ~87%, TNFa~22%, IL2~34.5%) and cytolytic proteins (Perforin~37%). This Example also demonstrated that CD5+CD7+ T cell progenitors can be genetically modified to express CD19 CARs and eventually differentiate into CAR T cells with significant cytotoxic effect on Raji cells (FIG. 18). The methods may be used for protocols for the efficient off-the shelf production and expansion of PSC-derived CAR T cells for treating hematologic malignancies or solid tumors.

Each publication, patent, and patent publication cited in this disclosure is incorporated by reference herein in its entirety. The present invention is not intended to be limited to the foregoing examples, but encompasses all such modifications and variations as come within the scope of the appended claims.

REFERENCES

1. Sugimura, R. et al. Haematopoietic stem and progenitor cells from human pluripotent stem cells. *Nature* 545, 432-438 (2017).
2. Rahman, N. et al. Engineering the haemogenic niche mitigates endogenous inhibitory signals and controls pluripotent stem cell-derived blood emergence. *Nat Commun* 8, 15380 (2017).
3. Ledran, M. H. et al. Efficient hematopoietic differentiation of human embryonic stem cells on stromal cells derived from hematopoietic niches. *Cell Stem Cell* 3, 85-98. (2008).
4. Wang, L. et al. Generation of hematopoietic repopulating cells from human embryonic stem cells independent of ectopic HOXB4 expression. *J Exp Med* 201, 1603-1614. Epub 2005 May 1609. (2005).
5. Vizcardo, R. et al. Regeneration of human tumor antigen-specific T cells from iPSCs derived from mature CD8(+) T cells. *Cell Stem Cell* 12, 31-36 (2013).
6. Lin, Y., Yoder, M. C. & Yoshimoto, M. Lymphoid progenitor emergence in the murine embryo and yolk sac precedes stem cell detection. *Stem Cells Dev* 23, 1168-1177 (2014).
7. Medvinsky, A., Rybtsov, S. & Taoudi, S. Embryonic origin of the adult hematopoietic system: advances and questions. *Development* 138, 1017-1031 (2011).
8. Tober, J., Maijenburg, M. W. & Speck, N. A. Taking the Leap: Runx1 in the Formation of Blood from Endothelium. *Curr Top Dev Biol* 118, 113-162 (2016).
9. Goldie, L. C., Lucitti, J. L., Dickinson, M. E. & Hirschi, K. K. Cell signaling directing the formation and function of hemogenic endothelium during murine embryogenesis. *Blood* 112, 3194-3204 (2008).
10. Li, W., Ferkowicz, M. J., Johnson, S. A., Shelley, W. C. & Yoder, M. C. Endothelial cells in the early murine yolk sac give rise to CD41-expressing hematopoietic cells. *Stem Cells Dev* 14, 44-54. (2005).
11. Frame, J. M., Fegan, K. H., Conway, S. J., McGrath, K. E. & Palis, J. Definitive Hematopoiesis in the Yolk Sac Emerges from Wnt-Responsive Hemogenic Endothelium Independently of Circulation and Arterial Identity. *Stem Cells* 34, 431-444 (2016).
12. Rybtsov, S., Ivanovs, A., Zhao, S. & Medvinsky, A. Concealed expansion of immature precursors underpins acute burst of adult HSC activity in foetal liver. *Development* 143, 1284-1289 (2016).
13. de Bruijn, M. F., Speck, N. A., Peeters, M. C. & Dzierzak, E. Definitive hematopoietic stem cells first develop within the major arterial regions of the mouse embryo. *The EMBO journal* 19, 2465-2474 (2000).
14. North, T. et al. Cbfa2 is required for the formation of intra-aortic hematopoietic clusters. *Development* 126, 2563-2575 (1999).
15. Yzaguirre, A. D. & Speck, N. A. Insights into blood cell formation from hemogenic endothelium in lesser-known anatomic sites. *Dev Dyn* (2016).
16. Gordon-Keylock, S., Sobiesiak, M., Rybtsov, S., Moore, K. & Medvinsky, A. Mouse extraembryonic arterial vessels harbor precursors capable of maturing into definitive HSCs. *Blood* 122, 2338-2345 (2013).
17. Lawson, N. D., Vogel, A. M. & Weinstein, B. M. sonic hedgehog and vascular endothelial growth factor act upstream of the Notch pathway during arterial endothelial differentiation. *Dev Cell* 3, 127-136 (2002).
18. Lawson, N. D. et al. Notch signaling is required for arterial-venous differentiation during embryonic vascular development. *Development* 128, 3675-3683 (2001).
19. Gering, M. & Patient, R. Hedgehog signaling is required for adult blood stem cell formation in zebrafish embryos. *Dev Cell* 8, 389-400 (2005).
20. Kim, P. G. et al. Signaling axis involving Hedgehog, Notch, and Scl promotes the embryonic endothelial-to-hematopoietic transition. *Proc Natl Acad Sci USA* 110, E141-150 (2013).
21. Burns, C. E. et al. A genetic screen in zebrafish defines a hierarchical network of pathways required for hematopoietic stem cell emergence. *Blood* 113, 5776-5782 (2009).
22. Ditadi, A. et al. Human definitive haemogenic endothelium and arterial vascular endothelium represent distinct lineages. *Nat Cell Biol* 17, 580-591 (2015).

23. Chong, D. C., Koo, Y., Xu, K., Fu, S. & Cleaver, O. Stepwise arteriovenous fate acquisition during mammalian vasculogenesis. *Dev Dyn* 240, 2153-2165 (2011).
24. Sacilotto, N. et al. Analysis of Dll4 regulation reveals a combinatorial role for Sox and Notch in arterial development. *Proc Natl Acad Sci USA* 110, 11893-11898 (2013).
25. Wythe, J. D. et al. ETS factors regulate Vegf-dependent arterial specification. *Dev Cell* 26, 45-58 (2013).
26. Uenishi, G. et al. Tenascin C promotes hematoendothelial development and T lymphoid commitment from human pluripotent stem cells in chemically defined conditions. *Stem cell reports* 3, 1073-1084 (2014).
27. Yamamizu, K. et al. Convergence of Notch and beta-catenin signaling induces arterial fate in vascular progenitors. *J Cell Biol* 189, 325-338 (2010).
28. Bertrand, J. Y. et al. Characterization of purified intra-embryonic hematopoietic stem cells as a tool to define their site of origin. *Proc Natl Acad Sci USA* 102, 134-139. Epub 2004 December 2027. (2005).
29. Gale, N. W. et al. Haploinsufficiency of delta-like 4 ligand results in embryonic lethality due to major defects in arterial and vascular development. *Proc Natl Acad Sci USA* 101, 15949-15954 (2004).
30. Duarte, A. et al. Dosage-sensitive requirement for mouse Dll4 in artery development. *Genes Dev* 18, 2474-2478 (2004).
31. Kim, I., Saunders, T. L. & Morrison, S. J. Sox17 dependence distinguishes the transcriptional regulation of fetal from adult hematopoietic stem cells. *Cell* 130, 470-483. Epub 2007 July 2026. (2007).
32. Yurugi-Kobayashi, T. et al. Adrenomedullin/cyclic AMP pathway induces Notch activation and differentiation of arterial endothelial cells from vascular progenitors. *Arterioscler Thromb Vasc Biol* 26, 1977-1984 (2006).
33. Corada, M. et al. Sox17 is indispensable for acquisition and maintenance of arterial identity. *Nat Commun* 4, 2609 (2013).
34. Villa, N. et al. Vascular expression of Notch pathway receptors and ligands is restricted to arterial vessels. *Mech Dev* 108, 161-164 (2001).
35. Choi, K. et al. Hematopoietic and endothelial differentiation of human induced pluripotent stem cells. *Stem Cells* 27, 559-567 (2009).
36. Vodyanik, M. A., Thomson, J. A. & Slukvin, II Leukosialin (CD43) defines hematopoietic progenitors in human embryonic stem cell differentiation cultures. *Blood* 108, 2095-2105 (2006).
37. Choi, K.-D. et al. Identification of the Hemogenic Endothelial Progenitor and Its Direct Precursor in Human Pluripotent Stem Cell Differentiation Cultures. *Cell Rep* 2, 553-567 (2012).
38. Kennedy, M., D'Souza, S. L., Lynch-Kattman, M., Schwantz, S. & Keller, G. Development of the hemangioblast defines the onset of hematopoiesis in human ES cell differentiation cultures. *Blood* 109, 2679-2687. (2007).
39. Kennedy, M. et al. T lymphocyte potential marks the emergence of definitive hematopoietic progenitors in human pluripotent stem cell differentiation cultures. *Cell Rep* 2, 1722-1735 (2012).
40. Sankaran, V. G. et al. Human fetal hemoglobin expression is regulated by the developmental stage-specific repressor BCL11A. *Science* 322, 1839-1842 (2008).
41. Ayllon, V. et al. The Notch ligand DLL4 specifically marks human hematoendothelial progenitors and regulates their hematopoietic fate. *Leukemia* 29, 1741-1753 (2015).
42. Salvagiotto, G. et al. Molecular profiling reveals similarities and differences between primitive subsets of hematopoietic cells generated in vitro from human embryonic stem cells and in vivo during embryogenesis. *Experimental Hematology* 36, 1377-1389 (2008).
43. Hong, C. C., Peterson, Q. P., Hong, J. Y. & Peterson, R. T. Artery/vein specification is governed by opposing phosphatidylinositol-3 kinase and MAP kinase/ERK signaling. *Curr Biol* 16, 1366-1372 (2006).
44. Herbert, S. P. et al. Arterial-venous segregation by selective cell sprouting: an alternative mode of blood vessel formation. *Science* 326, 294-298 (2009).
45. Espin-Palazon, R. et al. Proinflammatory signaling regulates hematopoietic stem cell emergence. *Cell* 159, 1070-1085 (2014).
46. Li, Y. et al. Inflammatory signaling regulates embryonic hematopoietic stem and progenitor cell production. *Genes Dev* 28, 2597-2612 (2014).
47. Richard, C. et al. Endothelio-mesenchymal interaction controls runx1 expression and modulates the notch pathway to initiate aortic hematopoiesis. *Dev Cell* 24, 600-611 (2013).
48. Hadland, B. K. et al. A Common Origin for B-1a and B-2 Lymphocytes in Clonal Pre-Hematopoietic Stem Cells. *Stem cell reports* 8, 1563-1572 (2017).
49. Ng, E. S. et al. Differentiation of human embryonic stem cells to HOXA+ hemogenic vasculature that resembles the aorta-gonad-mesonephros. *Nat Biotechnol* (2016).
50. Dou, D. R. et al. Medial HOXA genes demarcate haematopoietic stem cell fate during human development. *Nat Cell Biol* 18, 595-606 (2016).
51. McKinney-Freeman, S. et al. The transcriptional landscape of hematopoietic stem cell ontogeny. *Cell Stem Cell* 11, 701-714 (2012).
52. Monteiro, R. et al. Transforming Growth Factor beta Drives Hemogenic Endothelium Programming and the Transition to Hematopoietic Stem Cells. *Dev Cell* (2016).
53. Robert-Moreno, A. et al. Impaired embryonic haematopoiesis yet normal arterial development in the absence of the Notch ligand Jagged1. *EMBO J* 27, 1886-1895 (2008).
54. Vodyanik, M. A. et al. A mesoderm-derived precursor for mesenchymal stem and endothelial cells. *Cell Stem Cell* 7, 718-729 (2010).
55. Choi, K. D. et al. Identification of the hemogenic endothelial progenitor and its direct precursor in human pluripotent stem cell differentiation cultures. *Cell Rep* 2, 553-567 (2012).
56. Hu, Y. & Smyth, G. K. ELDA: extreme limiting dilution analysis for comparing depleted and enriched populations in stem cell and other assays. *J Immunol Methods* 347, 70-78 (2009).
57. Dias, J. et al. Generation of red blood cells from human induced pluripotent stem cells. *Stem Cells Dev* 20, 1639-1647 (2011).
58. Hou, Z. et al. A cost-effective RNA sequencing protocol for large-scale gene expression studies. *Sci Rep* 5, 9570 (2015).
59. Leng, N. et al. EBSeq: an empirical Bayes hierarchical model for inference in RNA-seq experiments. *Bioinformatics* 29, 1035-1043 (2013).
60. Bovolenta, L. A., Acencio, M. L. & Lemke, N. HTRIdb: an open-access database for experimentally verified human transcriptional regulation interactions. *BMC Genomics* 13, 405 (2012).
61. Cahan, P. et al. CellNet: network biology applied to stem cell engineering. *Cell* 158, 903-915 (2014).

62. Shannon, P. et al. Cytoscape: a software environment for integrated models of biomolecular interaction networks. *Genome Res* 13, 2498-2504 (2003).
63. Slukvin, II (2013). Hematopoietic specification from human pluripotent stem cells: current advances and challenges toward de novo generation of hematopoietic stem cells. *Blood* 122, 4035-4046.
64. Slukvin, II (2016). Generating human hematopoietic stem cells in vitro-exploring endothelial to hematopoietic transition as a portal for stemness acquisition. FEBS Lett.
65. Vo, L. T., and Daley, G. Q. (2015). De novo generation of HSCs from somatic and pluripotent stem cell sources. *Blood* 125, 2641-2648.
66. Langmead B, Trapnell C, Pop M, Salzberg S L. Ultrafast and memory-efficient alignment of short DNA sequences to the human genome. Genome Biology. 2009; 10(3):R25. doi:10.1186/gb-2009-10-3-r25.
67. Li B, Dewey C N. RSEM: accurate transcript quantification from RNA-Seq data with or without a reference genome. BMC Bioinformatics. 2011; 12:323. doi: 10.1186/1471-2105-12-323.

We claim:

1. A method of enhancing arterial specification of hemogenic endothelium, the method comprising:
   (a) introducing an ETS transcription factor transgene into a mesoderm cell population, wherein the ETS transcription factor is ETS1; and
   (b) culturing the mesoderm cells under conditions sufficient to express the ETS transcription factor transgene within the mesoderm population and differentiate the mesoderm cells to arterial hemogenic endothelium (AHE) cells.

2. The method of claim 1, wherein step (a) comprises introducing a vector comprising the ETS transcription factor transgene into the mesoderm cell population.

3. The method of claim 2, wherein the vector comprises an inducible promoter operably linked to the ETS transcription factor transgene.

4. The method of claim 1, wherein the mesoderm cell population is differentiated from human pluripotent stem cells (hPSCs).

5. The method of claim 1, wherein the mesoderm cells population expresses the ETS transcription factor for at least 2 days to differentiate to AHE cells.

6. A method of enhancing arterial specification of hemogenic endothelium in differentiating hPSC, comprising the steps of
   (a) introducing an ETS transcription factor transgene into a hPSC population, wherein the ETS transcription factor is ETS1,
   (b) culturing the hPSC cells under conditions to differentiate the hPSC into mesoderm cells at two days of differentiation, and
   (c) inducing expression of the transgene at day two of differentiation, such that arterial hemogenic endothelium cells (AHE) are obtained by day four of differentiation.

7. The method of claim 6, wherein the expression is under inducible control.

8. The method of claim 6, wherein the cells are further differentiated into lympho-myeloid and erythroid cell lines.

9. The method of claim 6, wherein a population of hemogenic endothelium cells that are CCD144+CD43−CD73−DLL4+CXCR4$^{+/-}$HE and express one or more arterial markers selected from the group consisting of EFNB2, NOTCH1, NOTCH 4 and SOX17 is obtained.

* * * * *